(12) United States Patent
Thompson et al.

(10) Patent No.: US 7,732,378 B2
(45) Date of Patent: *Jun. 8, 2010

(54) MASS LABELS

(75) Inventors: Andrew Hugin Thompson, Cambridge (GB); Christian Hamon, Frankfurt am Main (DE); Jurgen Schafer, Lauterbach (DE); Karsten Kuhn, Dortmund (DE); Joseph Schwarz, Frankfurt (DE); Thomas Neumann, Frankfurt am Main (DE)

(73) Assignee: Electrophoretics Limited, Cobham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/489,341

(22) PCT Filed: Sep. 16, 2002

(86) PCT No.: PCT/GB02/04240

§ 371 (c)(1), (2), (4) Date: Oct. 28, 2004

(87) PCT Pub. No.: WO03/025576

PCT Pub. Date: Mar. 27, 2003

(65) Prior Publication Data

US 2005/0048489 A1    Mar. 3, 2005

(30) Foreign Application Priority Data

Sep. 14, 2001 (EP) .................................. 01307830

(51) Int. Cl.
*C40B 40/00* (2006.01)

(52) U.S. Cl. .................................. 506/13; 506/7; 435/4

(58) Field of Classification Search .................. 435/7.1, 435/7.92; 530/388.9, 402, 412; 436/545, 436/546, 161, 824, 173
See application file for complete search history.

(56) References Cited

U.S. PATENT DOCUMENTS

| 5,482,858 | A  | * | 1/1996  | Huston et al. ............... 435/69.1 |
| 5,770,367 | A  |   | 6/1998  | Southern et al. |
| 6,027,890 | A  | * | 2/2000  | Ness et al. ..................... 435/6 |
| 6,635,452 | B1 | * | 10/2003 | Monforte et al. ........... 435/91.1 |
| 6,824,981 | B2 |   | 11/2004 | Chait et al. |
| 2003/0194717 | A1 | * | 10/2003 | Schmidt et al. ................. 435/6 |

FOREIGN PATENT DOCUMENTS

| AT | 364841 T | * | 7/2007 |
| WO | 97/27331 | | 7/1997 |
| WO | WO 97/37953 | | 10/1997 |
| WO | 98/26095 | | 6/1998 |
| WO | 98/31830 | | 7/1998 |
| WO | 99/02728 | | 1/1999 |
| WO | WO 99/14362 | | 3/1999 |
| WO | WO 99/32501 | | 7/1999 |
| WO | 01/68664 | | 9/2001 |

OTHER PUBLICATIONS

S. P. Gygi, et al.; Quantitative Analysis of Complex Protein Mixtures Using Isotope-Coded Affinity Tags; Research Paper; Nature Biotechnology; Oct. 17, 1999; pp. 994-999; vol. 17; Nature Publishing; USA.

Dunayevskiy. Yuriy et al., "Application of capillary electrophoresis-electrospray ionization mass spectrometry in the determination of molecular diversity" Proc. Natl. Acad. Sci. USA, vol. 93, pp. 6152-6157, Jun. 1996.

* cited by examiner

*Primary Examiner*—Jeffrey S Lundgren
(74) *Attorney, Agent, or Firm*—Crowell & Moring LLP

(57) ABSTRACT

Provided is a set of two or more mass labels, each label in the set comprising a mass marker moiety attached via a cleavable linker having at least one amide bond to a mass normalization moiety, wherein the aggregate mass of each label in the set may be the same or different and the mass of the mass marker moiety of each label in the set may be the same or different, and wherein in any group of labels within the set having a mass marker moiety of a common mass each label has an aggregate mass different from all other labels in that group, and wherein in any group of labels within the set having a common aggregate mass each label has a mass marker moiety having a mass different from that of all other mass marker moieties in that group, such that all of the mass labels in the set are distinguishable from each other by mass spectrometry, and wherein the mass marker moiety comprises an amino acid and the mass normalization moiety comprises an amino acid.

22 Claims, 26 Drawing Sheets

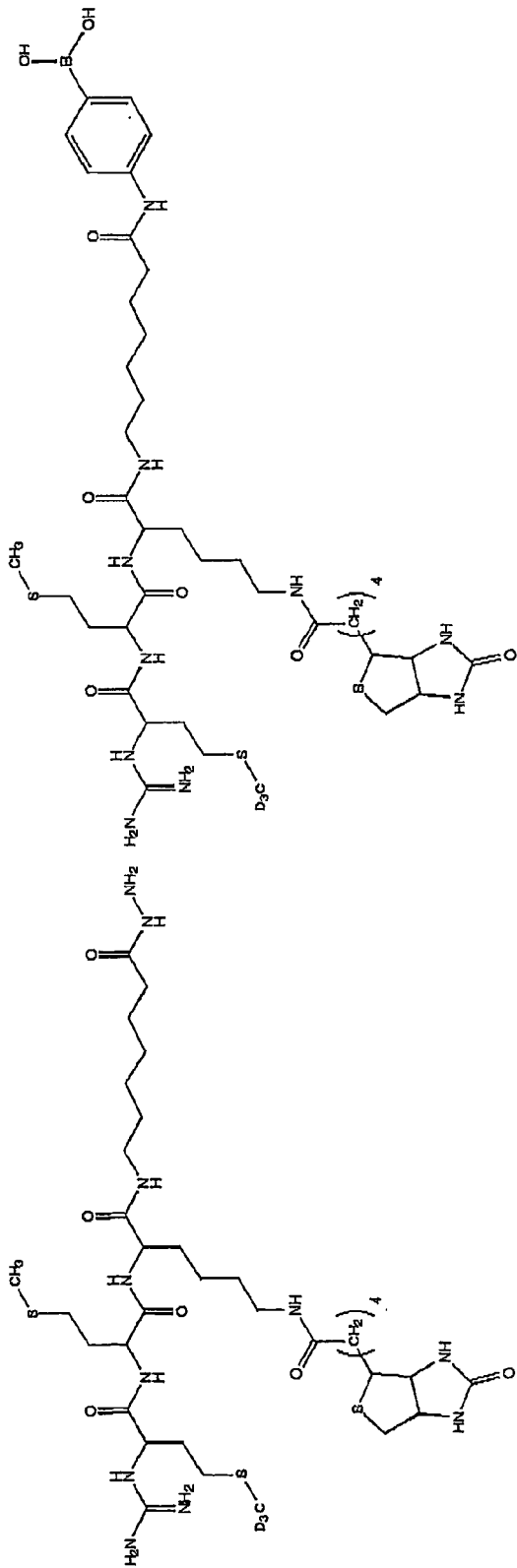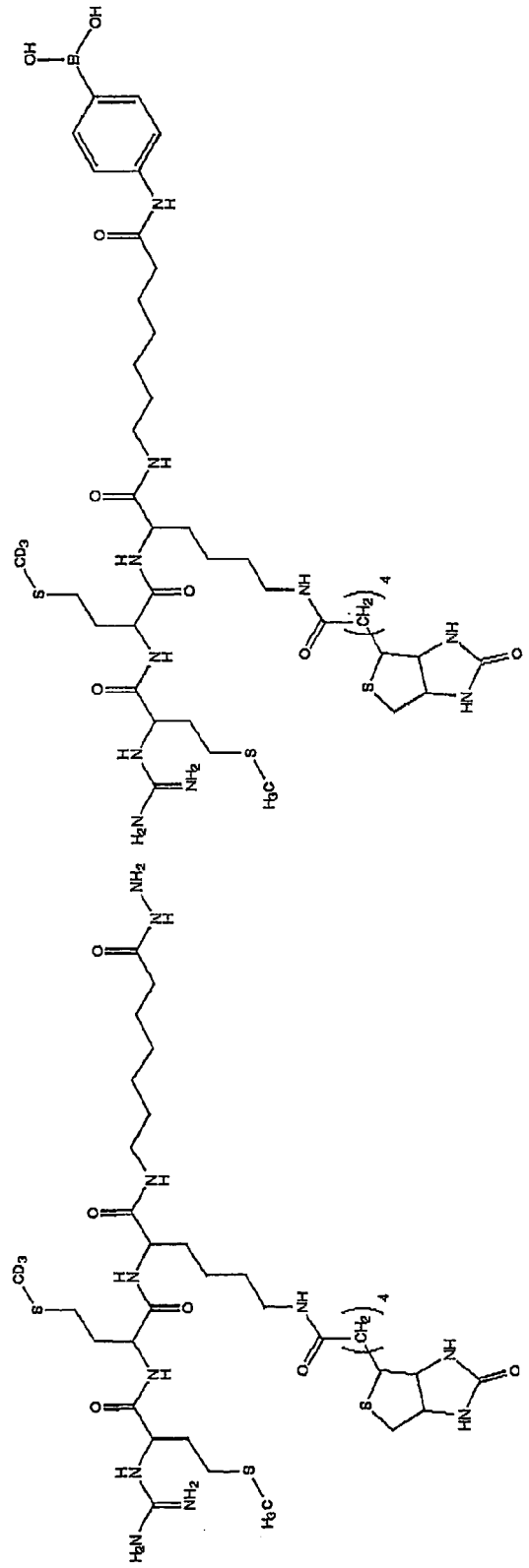
Figure 6a
Figure 6b

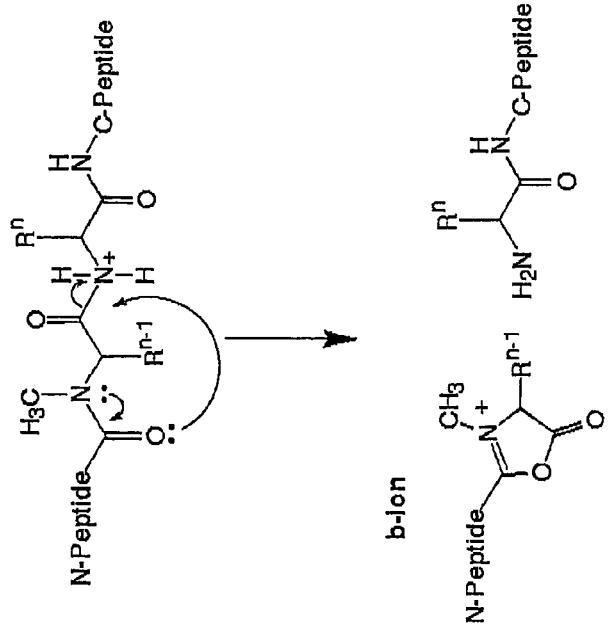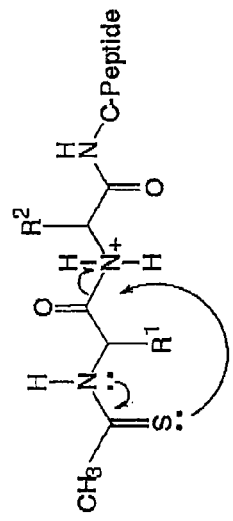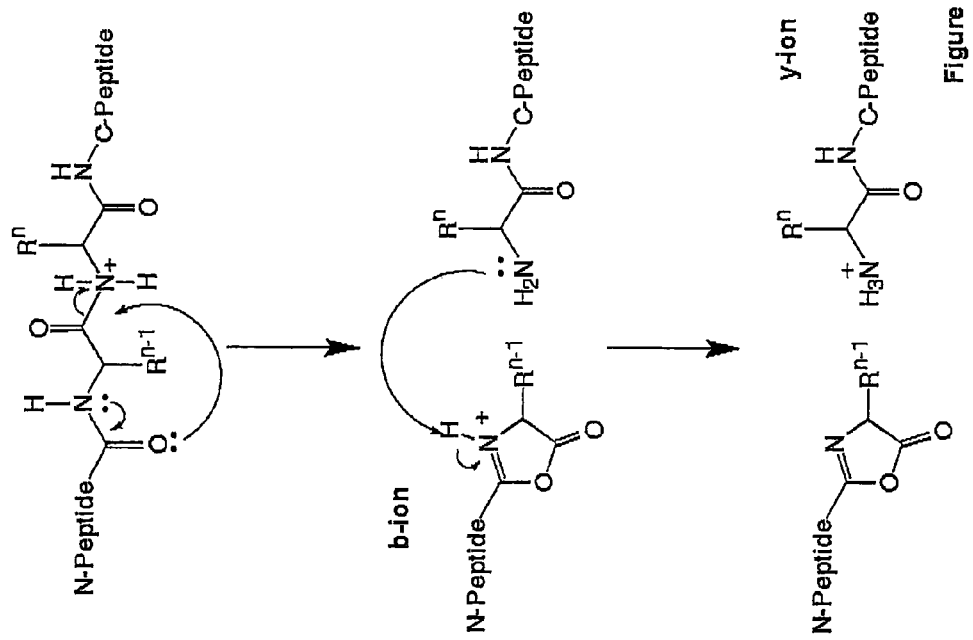
Figure 16b
Figure 16c
Figure 16a

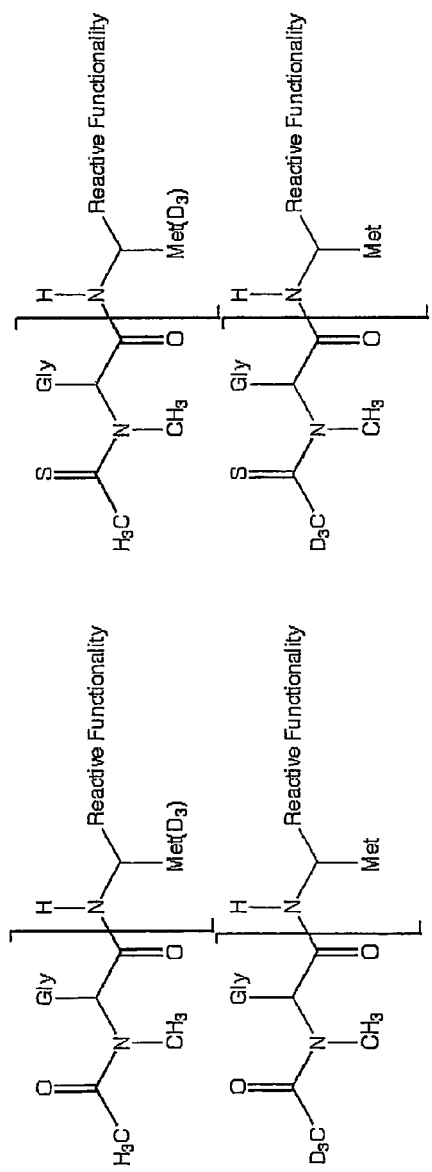
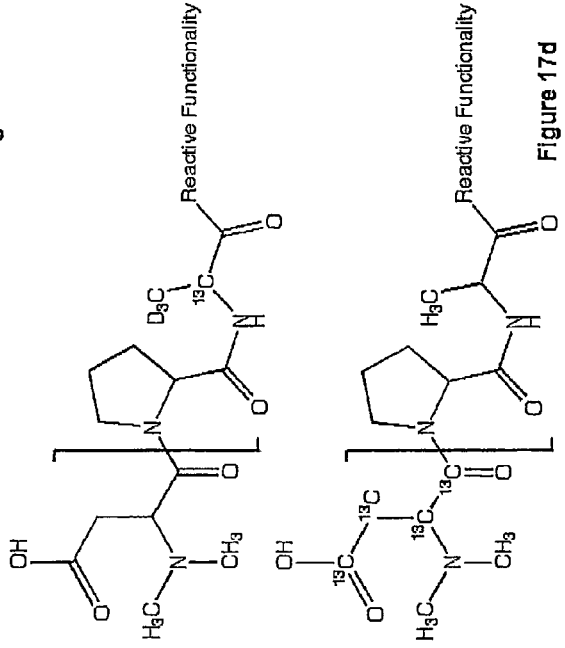
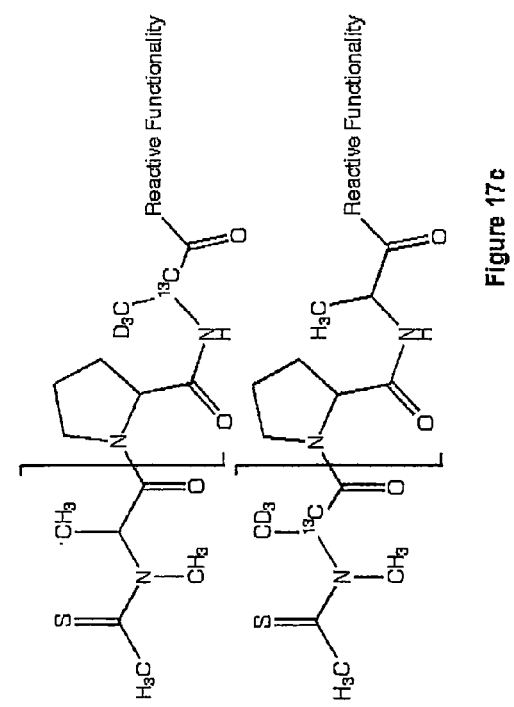
Figure 17a, Figure 17b, Figure 17c, Figure 17d

MS-mode analysis of the TMT1 and TMT2 peptide mixture:

CID MS/MS-mode:

Zoom:

Peptide 1:

Peptide 2:

Peptide 3:

MASS LABELS

This invention relates to useful compounds for labeling molecules of interest, particularly biomolecules such as peptides and proteins. Specifically this invention relates to labeling of analytes for detection by mass spectrometry and associated methods of analysing mass labeled analytes by mass spectrometry.

Various methods of labeling molecules of interest are known in the art, including radioactive atoms, fluorescent dyes, luminescent reagents, electron capture reagents and light absorbing dyes. Each of these labeling systems has features which make it suitable for certain applications and not others. For reasons of safety, interest in non-radioactive labeling systems lead to the widespread commercial development of fluorescent labeling schemes particularly for genetic analysis. Fluorescent labeling schemes permit the labeling of a relatively small number of molecules simultaneously, typically 4 labels can be used simultaneously and possibly up to eight. However the costs of the detection apparatus and the difficulties of analysing the resultant signals limit the number of labels that can be used simultaneously in a fluorescence detection scheme.

More recently there has been development in the area of mass spectrometry as a method of detecting labels that are cleavably attached to their associated molecule of interest. In many molecular biology applications one needs to be able to perform separations of the molecules of interest prior to analysis. These are generally liquid phase separations. Mass spectrometry in recent years has developed a number of interfaces for liquid phase separations which make mass spectrometry particularly effective as a detection system for these kinds of applications. Until recently Liquid Chromatography Mass Spectrometry was used to detect analyte ions or their fragment ions directly, however for many applications such as nucleic acid analysis, the structure of the analyte can be determined from indirect labeling. This is advantageous particularly with respect to the use of mass spectrometry because complex biomolecules such as DNA have complex mass spectra and are detected with relatively poor sensitivity. Indirect detection means that an associated label molecule can be used to identify the original analyte, where the label is designed for sensitive detection and a simple mass spectrum. Simple mass spectra mean that multiple labels can be used to analyse multiple analytes simultaneously.

PCT/GB98/00127 describes arrays of nucleic acid probes covalently attached to cleavable labels that are detectable by mass spectrometry which identify the sequence of the covalently linked nucleic acid probe. The labeled probes of this application have the structure Nu—L—M where Nu is a nucleic acid covalently linked to L, a cleavable linker, covalently linked to M, a mass label. Preferred cleavable linkers in this application cleave within the ion source of the mass spectrometer. Preferred mass labels are substituted poly-aryl ethers. These application discloses a variety of ionisation methods and analysis by quadrupole mass analysers, TOF analysers and magnetic sector instruments as specific methods of analysing mass labels by mass spectrometry.

PCT/GB94/01675 disclose ligands, and specifically nucleic acids, cleavably linked to mass tag molecules. Preferred cleavable linkers are photo-cleavable. These application discloses Matrix Assisted Laser Desorption Ionisation (MALDI) Time of Flight (TOF) mass spectrometry as a specific method of analysing mass labels by mass spectrometry.

PCT/US97/22639 discloses releasable non-volatile mass-label molecules. In preferred embodiments these labels comprise polymers, typically biopolymers which are cleavably attached to a reactive group or ligand, i.e. a probe. Preferred cleavable linkers appear to be chemically or enzymatically cleavable. This application discloses MALDI TOF mass spectrometry as a specific method of analysing mass labels by mass spectrometry.

PCT/US97/01070, PCT/US97/01046, and PCT/US97/01304 disclose ligands, and specifically nucleic acids, cleavably linked to mass tag molecules. Preferred cleavable linkers appear to be chemically or photo-cleavable. These application discloses a variety of ionisation methods and analysis by quadrupole mass analysers, TOF analysers and magnetic sector instruments as specific methods of analysing mass labels by mass spectrometry.

None of these prior art applications mention the use of tandem or serial mass analysis for use in analysing mass labels.

Gygi et al. (Nature Biotechnology 17: 994-999, "Quantitative analysis of complex protein mixtures using isotope-coded affinity tags" 1999) disclose the use of 'isotope encoded affinity tags' for the capture of peptides from proteins, to allow protein expression analysis. In this article, the authors describe the use of a biotin linker, which is reactive to thiols, for the capture peptides with cysteine in them. A sample of protein from one source is reacted with the biotin linker and cleaved with an endopeptidase. The biotinylated cysteine-containing peptides can then be isolated on avidinated beads for subsequent analysis by mass spectrometry. Two samples can be compared quantitatively by labeling one sample with the biotin linker and labeling the second sample with a deuterated form of the biotin linker. Each peptide in the samples is then represented as a pair of peaks in the mass spectrum. Integration of the peaks in the mass spectrum corresponding to each tag indicate the relative expression levels of the peptide linked to the tags.

This 'isotope encoding' method has a number of limitations. A first is the reliance on the presence of thiols in a protein—many proteins do not have thiols while others have several. In a variation on this method, linkers may be designed to react with other side chains, such as amines. However, since many proteins contain more than one lysine residue, multiple peptides per protein would generally be isolated in this approach. It is likely that this would not reduce the complexity of the sample sufficiently for analysis by mass spectrometry. A sample that contains too many species is likely to suffer from 'ion suppression', in which certain species ionise preferentially over other species which would normally appear in the mass spectrum in a less complex sample. In general, capturing proteins by their side chains is likely to give either too many peptides per protein or certain proteins will be missed altogether.

The second limitation of this approach is the method used to compare the expression levels of proteins from different samples. Labeling each sample with a different isotope variant of the affinity tag results in an additional peak in the mass spectrum for each peptide in each sample. This means that if two samples are analysed together there will be twice as many peaks in the spectrum. Similarly, if three samples are analysed together, the spectrum will be three times more complex than for one sample alone. It is clear that this approach will be limited, since the ever increasing numbers of peaks will increase the likelihood that two different peptides will have overlapping peaks in the mass spectrum.

A further limitation, which is reported by the authors of the above paper, is the mobility change caused by the tags. The authors report that peptides labeled with the deuterated biotin tag elute slightly after the same peptide labeled with the undeuterated tag.

The mass spectra generated for analyte material are very sensitive to contaminants. Essentially, any material introduced into the mass spectrometer that can ionise will appear in the mass spectrum. This means that for many analyses it is necessary to carefully purify the analyte before introducing it into the mass spectrometer. For the purposes of high throughput systems for indirect analysis of analytes through mass labels it would be desirable to avoid any unnecessary sample preparation steps. That is to say it would be desirable to be able to detect labels in a background of contaminating material and be certain that the peak that is detected does in fact correspond to a label. The prior art does not disclose methods or compositions that can improve the signal to noise ratio achievable in mass spectrometry based detection systems or that can provide confirmation that a mass peak in a spectrum was caused by the presence of a mass label.

For the purposes of detection of analytes after liquid chromatography or electrophoretic separations it is desirable that the labels used, minimally interfere with the separation process. If an array of such labels are used, it is desirable that the effect of each member of the array on its associated analyte is the same as every other label. This conflicts to some extent with the intention of mass marking which is to generate arrays of labels that are resolvable in the mass spectrometer on the basis of their mass. It is disclosed in the prior art above that mass labels should preferably be resolved by 4 Daltons to prevent interference of isotope peaks from one label with those of another label. This means that to generate 250 distinct mass labels would require labels spread over a range of about 1000 Daltons and probably more, since it is not trivial to generate large arrays of labels separated by exactly 4 Daltons. This range of mass will almost certainly result in mass labels that will have a distinct effect on any separation process that precedes detection by mass spectrometry. It also has implications for instrument design, in that as the mass range over which a mass spectrometer can detect ions increases, the cost of the instrument increases.

It is thus an object of this invention to solve the problems associated with the above prior art, and to provide mass labels which can be detected in a background of contamination and whose identity as mass labels can be confirmed. Furthermore it is an object of this invention to provide arrays of labels which can be resolved in a compressed mass range so that the labels do not interfere as much with separation processes and which can be detected easily in a mass spectrometer that detects ions over a limited range of mass to charge ratios.

It is also an object of this invention to provide methods of analysing biomolecules which exploit the labels of this invention to maximise throughput, signal to noise ratios and sensitivity of such assays, particularly for the analysis of peptides.

In a first aspect the invention provides a set of two or more mass labels, each label in the set comprising a mass marker moiety attached via at least one amide bond to a mass normalisation moiety, wherein the aggregate mass of each label in the set may be the same or different and the mass of the mass marker moiety of each label in the set may be the same or different, and wherein in any group of labels within the set having a mass marker moiety of a common mass each label has an aggregate mass different from all other labels in that group, and wherein in any group of labels within the set having a common aggregate mass each label has a mass marker moiety having a mass different from that of all other mass marker moieties in that group, such that all of the mass labels in the set are distinguishable from each other by mass spectrometry, and wherein the mass marker moiety comprises an amino acid and the mass normalisation moiety comprises an amino acid.

The term mass marker moiety used in the present context is intended to refer to a moiety that is to be detected by mass spectrometry, whilst the term mass normalisation moiety used in the present context is intended to refer to a moiety that is not necessarily to be detected by mass spectrometry, but is present to ensure that a mass label has a desired aggregate mass. The number of labels in the set is not especially limited, provided that the set comprises a plurality of labels. However, it is preferred if the set comprises two or more, three or more, four or more, or five or more labels.

The present invention also provides an array of mass labels, comprising two or more sets of mass labels as defined above, wherein the aggregate mass of each of the mass labels in any one set is different from the aggregate mass of each of the mass labels in every other set in the array. The mass marker moiety and the mass normalisation moiety both comprise at least one amino acid. However, the moieties may comprises further groups, if desired, such as more amino acid groups, and/or aryl ether groups. Thus the moieties may be modified amino acids, or may be peptides. The masses of the different sets in the array may be distinguished by adding further amino acid groups to either or both of the moieties as required.

Further provided by the invention is a method of analysis, which method comprises detecting an analyte by identifying by mass spectrometry a mass label or a combination of mass labels unique to the analyte, wherein the mass label is a mass label from a set or an array of mass labels as defined above.

In certain embodiments of this invention the mass tags may comprise reactive functionalities which facilitate the attachment of the mass tags to analyte molecules. The tags in this embodiment are preferably of the following form:

amino acid 1-amide bond-amino acid 2-reactive functionality where the mass marker moiety and the mass nornalisation moiety may each be either amino acid 1 or amino acid 2.

In preferred embodiments of the invention, the array of tags are preferably all chemically identical and the masses of the mass normalisation and mass marker moieties (e.g. amino acid 1 and acid 2 above) are altered by isotope substitutions.

In further preferred embodiments of this invention, the tags may comprise a sensitivity enhancing group. The tags are preferably of the form:

sensitivity enhancing group-amino acid 1-amide bond-amino acid 2-reactive Functionality In this example the sensitivity enhancing group is usually attached to the mass marker moiety, since it is intended to increase the sensitivity of the detection of this moiety in the mass spectrometer. The reactive functionality is shown as being present and attached to a different moiety than the sensitivity enhancing group. However, the tags need not be limited in this way and in some cases comprise the sensitivity enhancing group without the reactive functionality. In other embodiments the sensitivity enhancing group may be attached to the same moiety as the reactive functionality.

In certain embodiments of the invention the mass tags comprise an affinity capture reagent. Preferably, the affinity capture ligand is biotin. The affinity capture ligand allows labeled analytes to be separated from unlabeled analytes by capturing them, e.g. on an avidinated solid phase.

In a further aspect the invention provides a method of analysing a biomolecule or a mixture of biomolecules. This method preferably comprises the steps of:

1. Reacting the biomolecule or mixture of biomolecules with a mass marker according to this invention;
2. Optionally separating the labeled biomolecule electrophoretically or chromatographically;
3. Ionising the labeled biomolecule;
4. Selecting ions of a predetermined mass to charge ratio corresponding to the mass to charge ratio of the preferred ions of the labeled biomolecule in a mass analyser;
5. Inducing dissociation of these selected ions by collision;
6. Detecting the collision products to identify collision product ions that are indicative of the mass labels.

In this embodiment, where the mass tags comprise an affinity tag, the affinity tagged biomolecules may be captured by a counter-ligand to allow labeled biomolecules to be separated from unlabeled biomolecules. This step preferably takes place prior to the optional second step above.

In certain embodiments the step of selecting the ions of a predetermined mass to charge ratio is performed in the first mass analyser of a serial instrument. The selected ions are then channeled into a separate collision cell where they are collided with a gas or a solid surface according to the fourth step of the first aspect of the invention. The collision products are then channeled into a further mass analyser of a serial instrument to detect collision products according to the fifth step of the first aspect of this invention. Typical serial instruments include triple quadrupole mass spectrometers, tandem sector instruments and quadrupole time of flight mass spectrometers.

In other embodiments, the step of selecting the ions of a predetermined mass to charge ratio, the step of colliding the selected ions with a gas and the step of detecting the collision products are performed in the same zone of the mass spectrometer. This may effected in ion trap mass analysers and Fourier Transform Ion Cyclotron Resonance mass spectrometers, for example.

In another aspect, this invention provides sets or arrays of mass labeled molecules of the form:

analyte-linker-label where label is a mass marker from a set or array according to this invention, the linker is a linker as described below and analyte may be any analyte of interest such as a biomolecule. One preferred aspect of this embodiment is where the analytes (one, more than one or even all the analytes) in the set or array are standard analytes with a known mass or with predetermined chromatographic properties. Such standards can be employed in the methods of the present invention for comparison with unknown analytes, for example when analysing the results of a chromatographic separation step.

This invention describes mass markers that may be readily produced in a peptide synthesiser. Indeed, the compounds used in this invention comprises peptides and modified peptides. Peptide synthesis provides chemical diversity allowing for a wide range of markers with chosen properties to be produced in an automated fashion.

The term 'MS/MS' in the context of mass spectrometers refers to mass spectrometers capable of selecting ions, subjecting selected ions to Collision Induced Dissociation (CID) and subjecting the fragment ions to further analysis.

The term 'serial instrument' refers to mass spectrometers capable of MS/MS in which mass analysers are organised in series and each step of the MS/MS process is performed one after the other in linked mass analysers. Typical serial instruments include triple quadrupole mass spectrometers, tandem sector instruments and quadrupole time of flight mass spectrometers.

The invention will now be described in further detail by way of example only, with reference to the accompanying drawings, in which:

FIG. 6a shows a set of 2 affinity ligand mass tags derived from methionine with a hydrazide functionality for labeling carbohydrates;

FIG. 6b shows a set of 2 affinity ligand mass tags derived from methionine with a boronic acid functionality for labeling carbohydrates;

FIGS. 16a-16c depict proposed fragmentation mechanisms;

FIGS. 17a-17d illustrate tags which exploit enhancing cleavage at the cleavable amide bond;

Figure 20A:
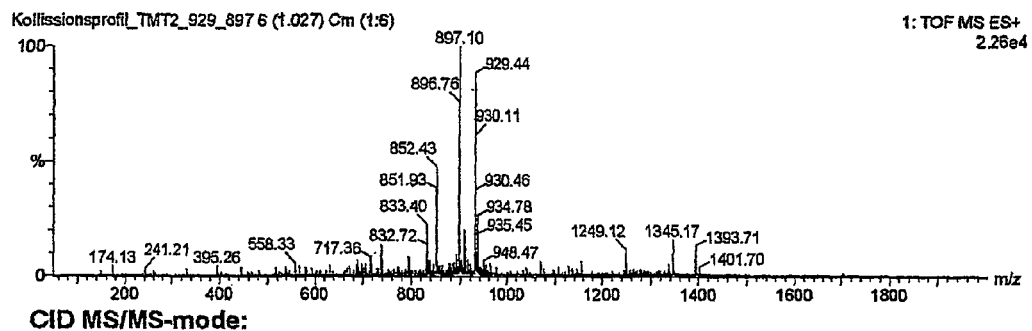
Figure 20B:
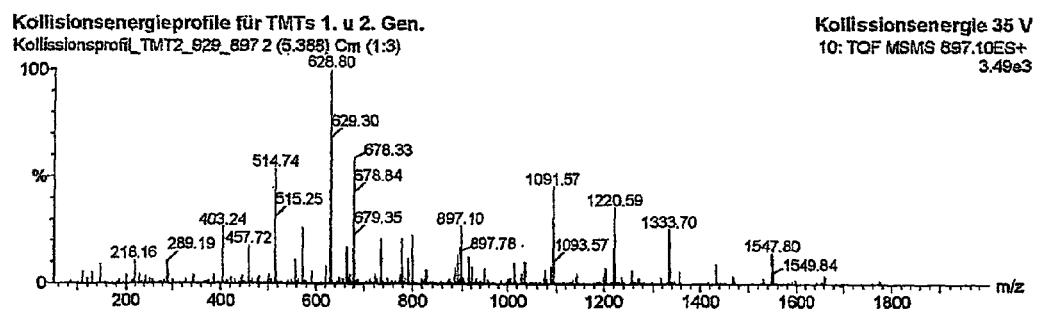
Figure 20B:
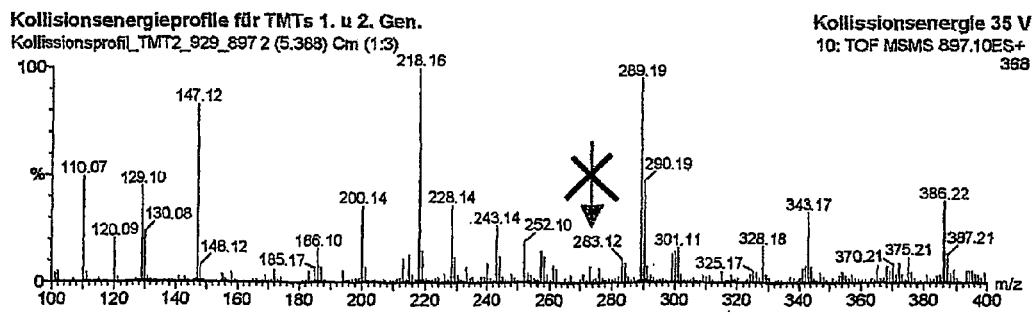
Figure 20C:
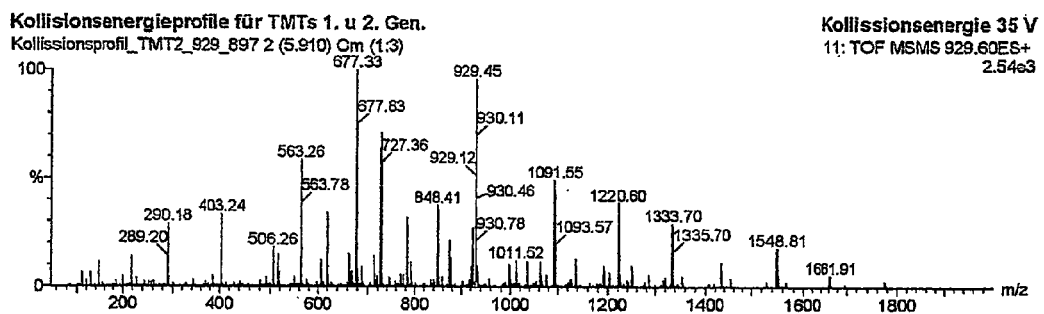
Figure 20C:
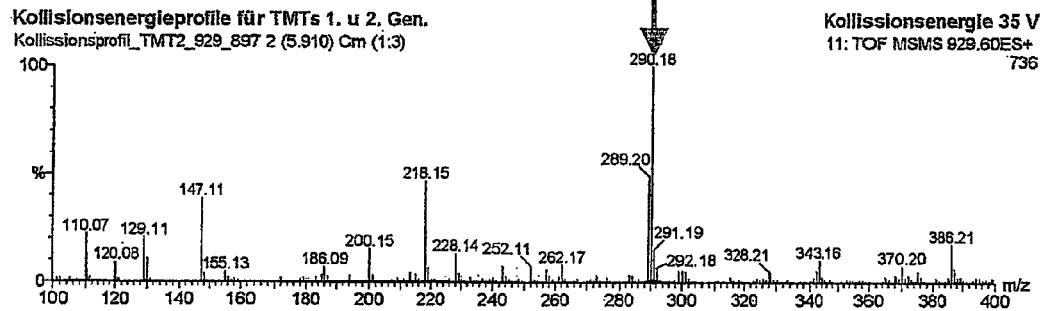
Figure 21:
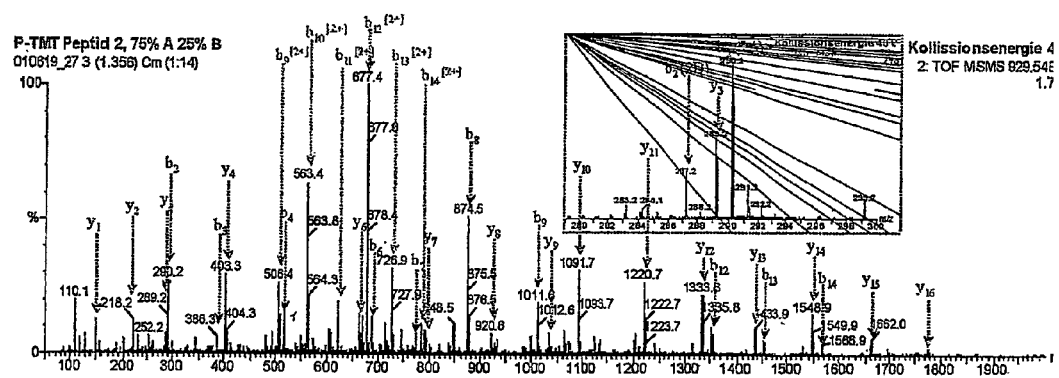
Figure 22:
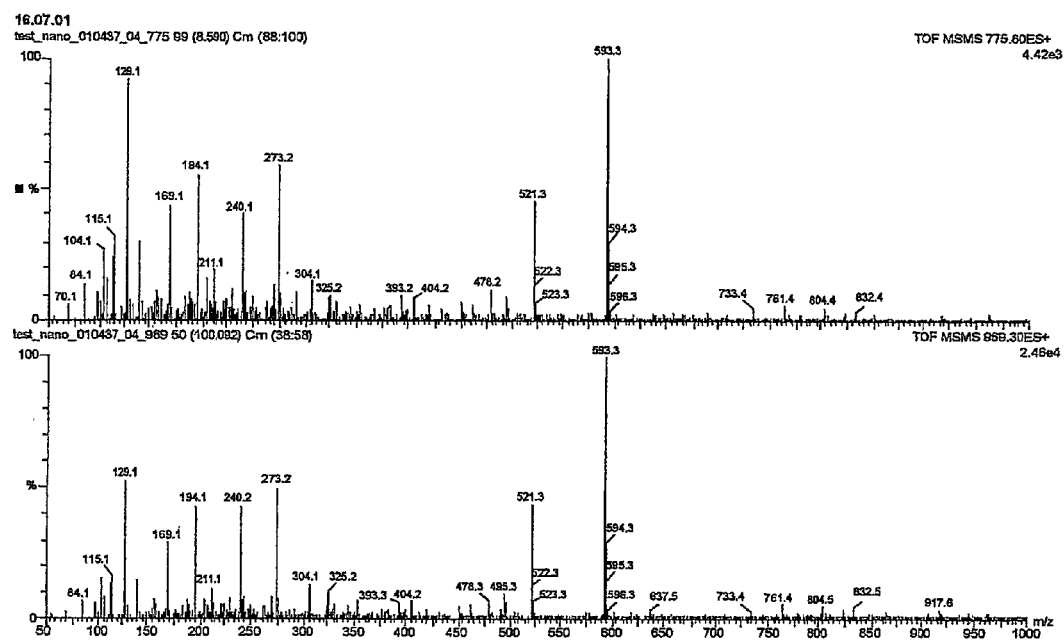
Figure 23:
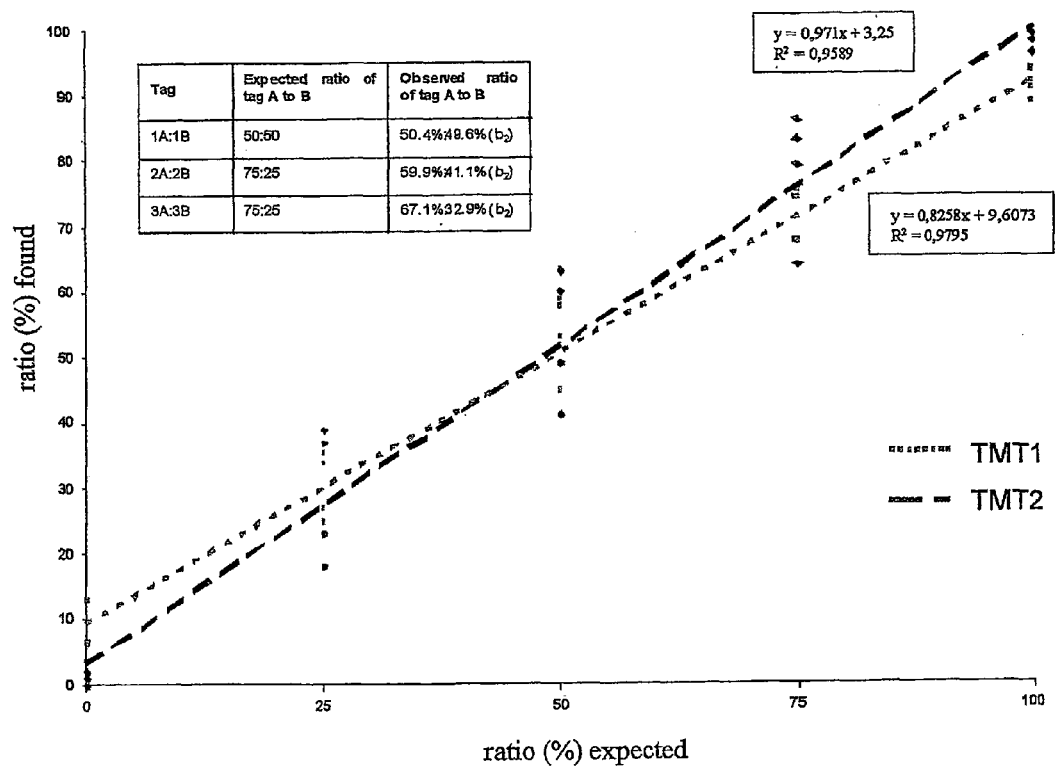
Figure 24:
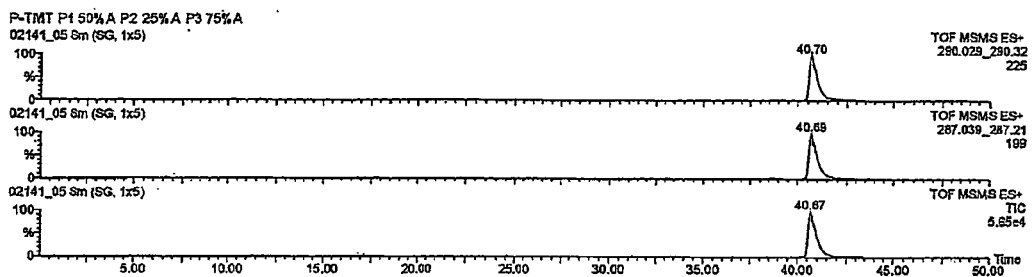
Figure 24:
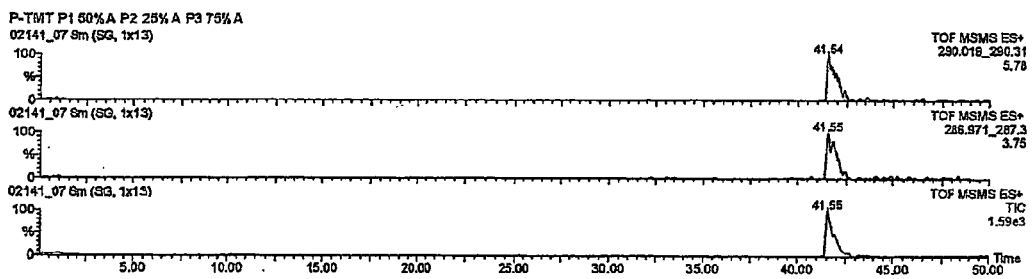
Figure 24:
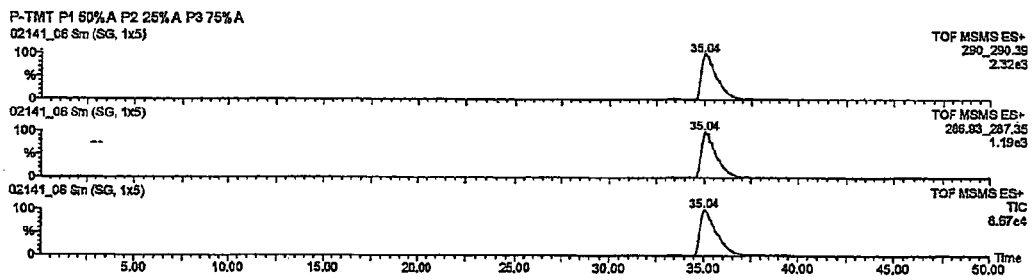
Figure 25:
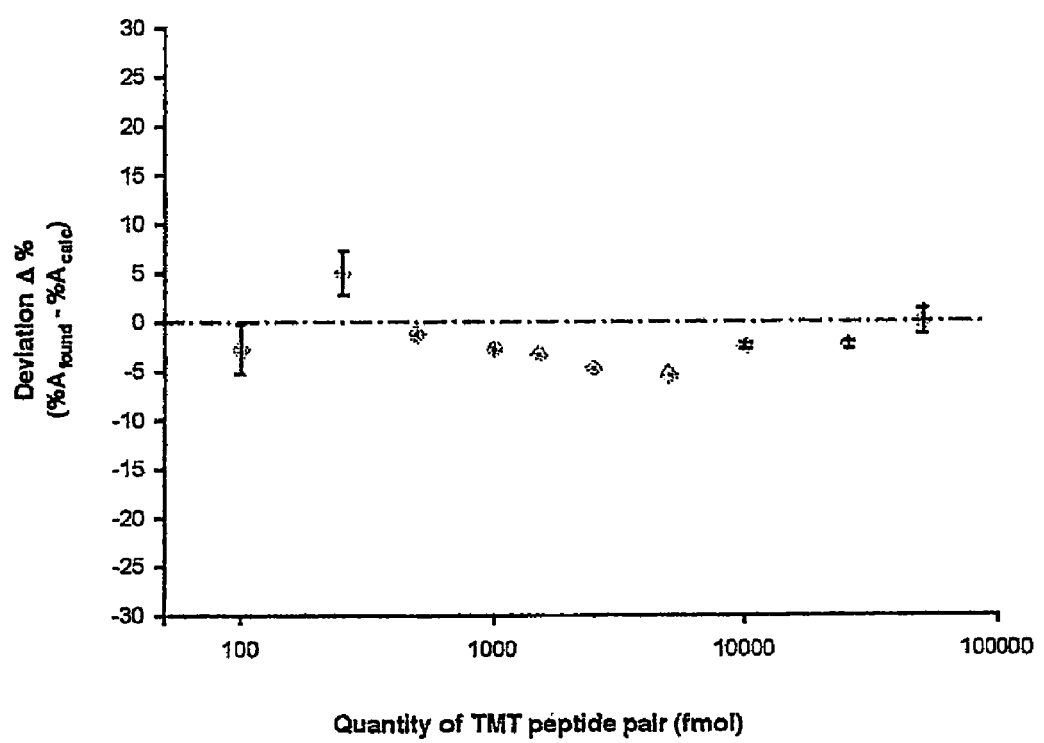
Figure 26A:
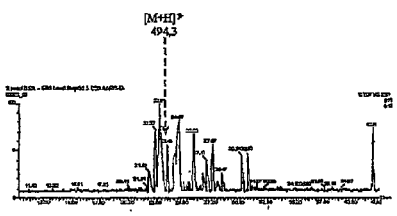
Figure 26B:
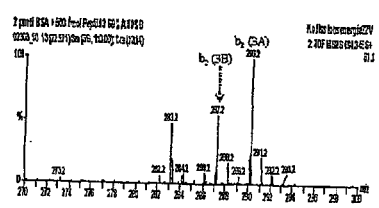
Figure 26C:
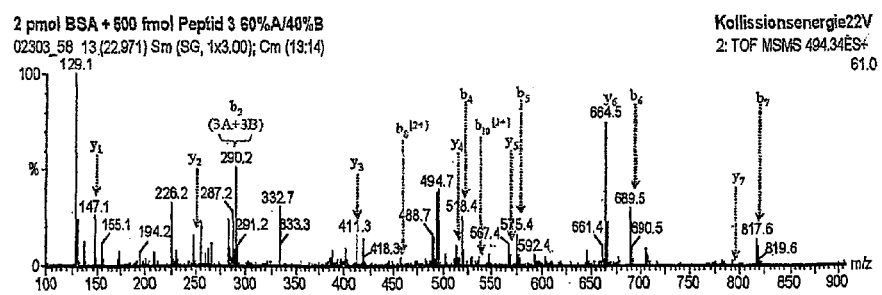

FIGS. 20a 20b and 20c show MS and MS/MS spectra for triply charged ions of the peptide 2 (see Table 7) labeled with the first and second generation TMTs;

FIG. 21 shows a typical CID spectra for a peptide (peptide 2 in Table 7) labeled with a second generation TMT;

FIG. 22 shows that the charge state of the TMT tagged peptide does not affect the appearance of the tag fragments in the CID spectra of the labeled peptides;

FIG. 23 shows peptide mixtures with the expected and measured abundance ratios for both the first and second generation tags;

FIG. 24 shows the co-elution of each peptide pair, peptides A and B for each peptide from Table 7;

FIG. 25 shows a dynamic range study of TMT peptide pairs 3A/3B, which are present in a ratio of 40:60 and have been analysed at dilutions in the range from 100 fmole to 100 pmole; and FIGS. 26a 26b and 26c show the results of a spiking experiment in which peptides pairs 3A and 3B (500 fmol in total, in a ratio of 40:60 respectively) bearing a second generation TMT was mixed with a tryptic digest of Bovine Serum Albumin (2 pmol).

Figure 1:
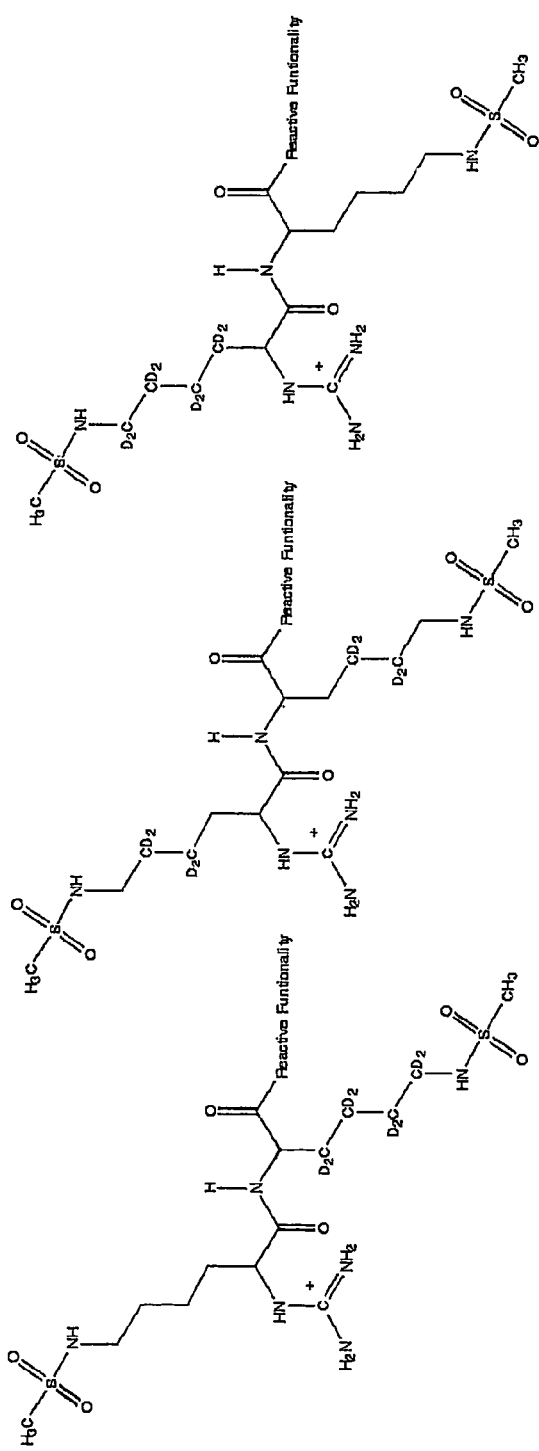
FIG. 1 shows a set of 3 mass tags derived from lysine.
Figure 2:
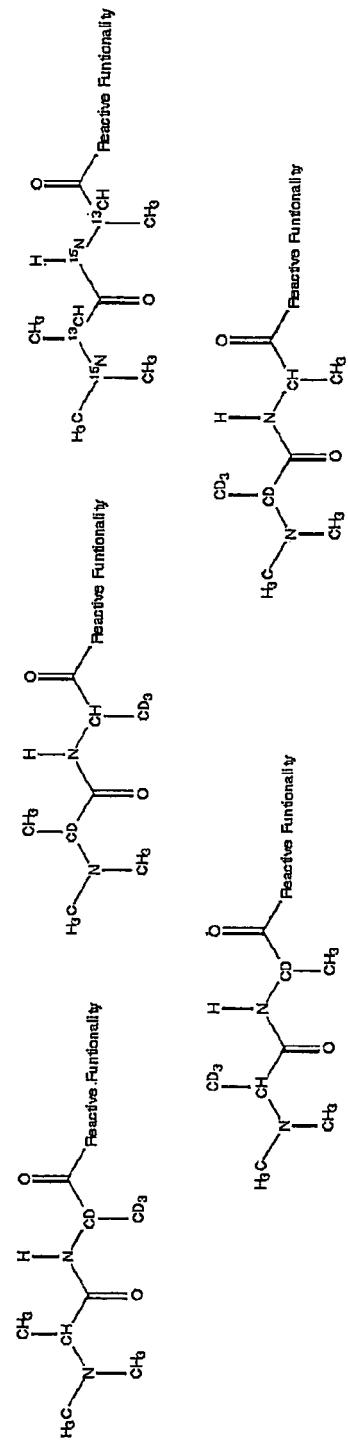
FIG. 2 shows a set of 5 mass tags derived from alanine.
Figure 3:
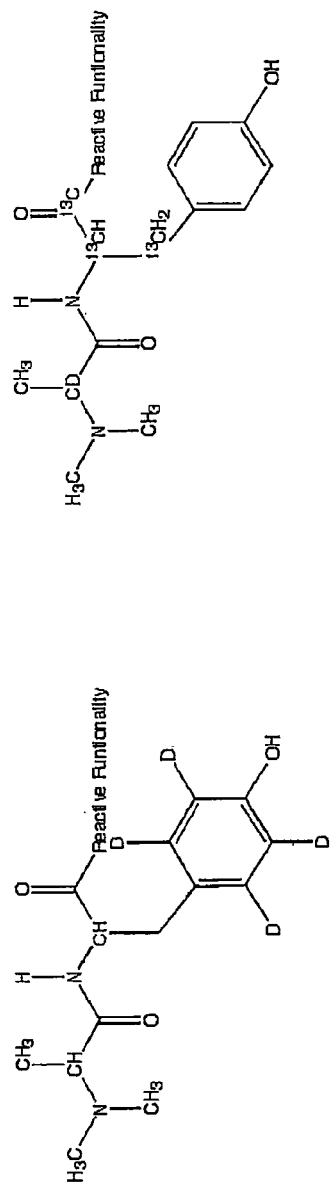
FIG. 3 shows a set of 5 mass tags derived from alanine and tyrosine.
Figure 3:
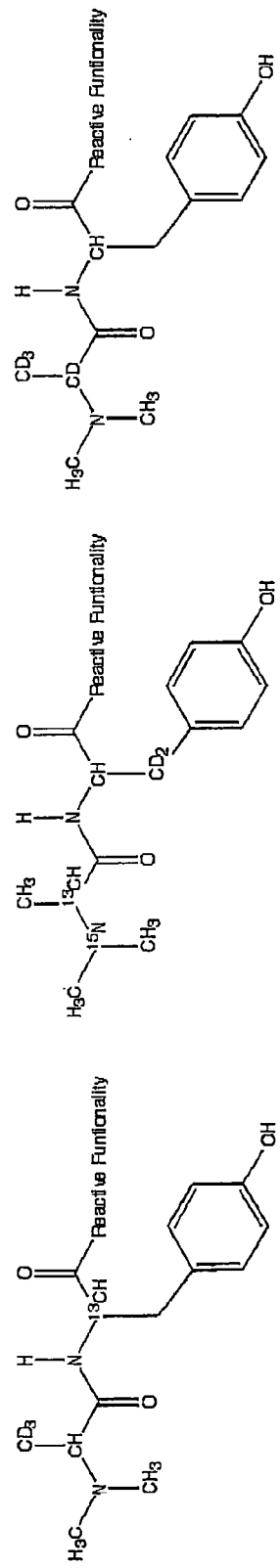
Figure 4:
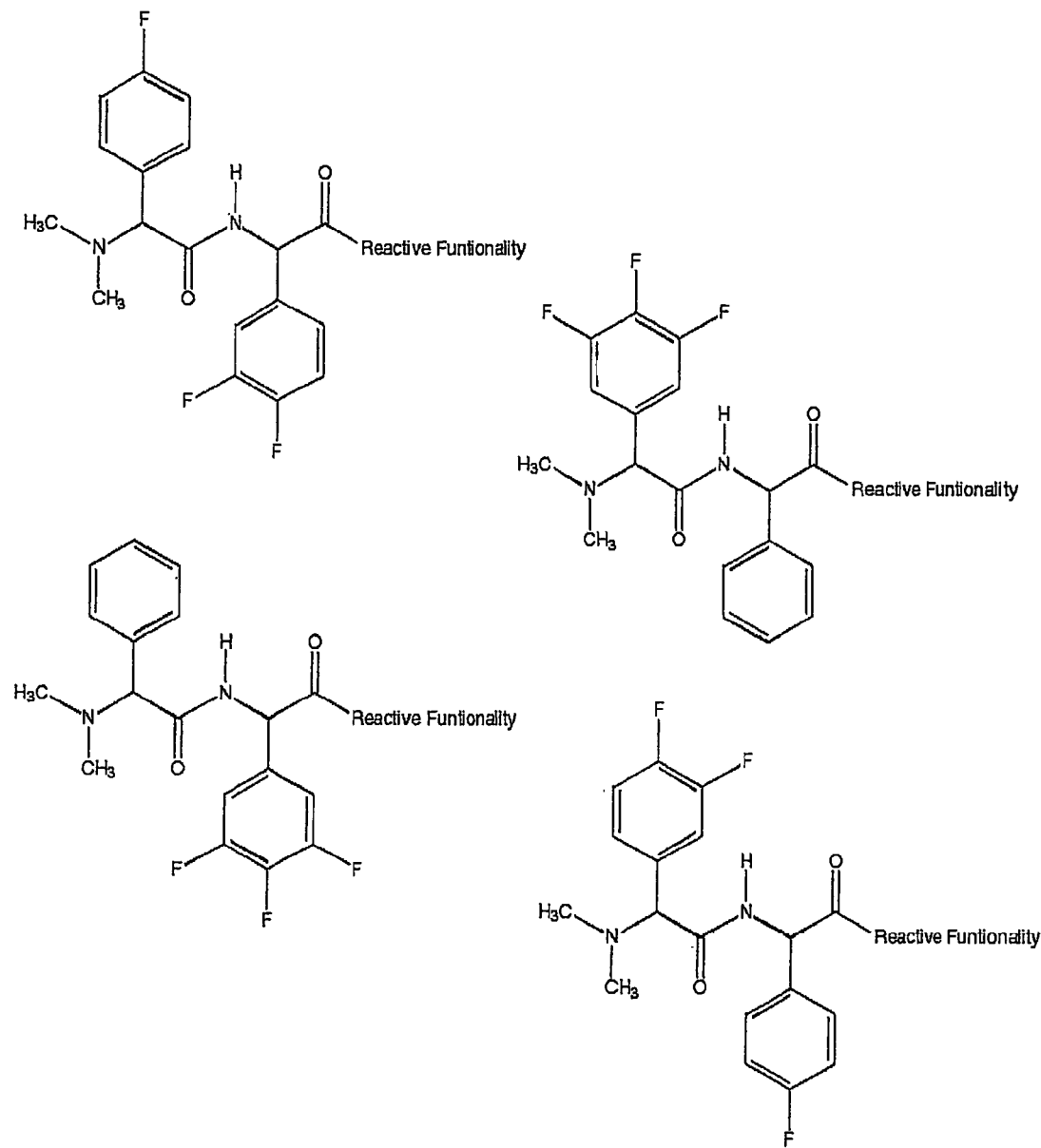
FIG. 4 shows a set of 4 mass tags derived from fluorinated forms of phenylglycine.
Figure 5:
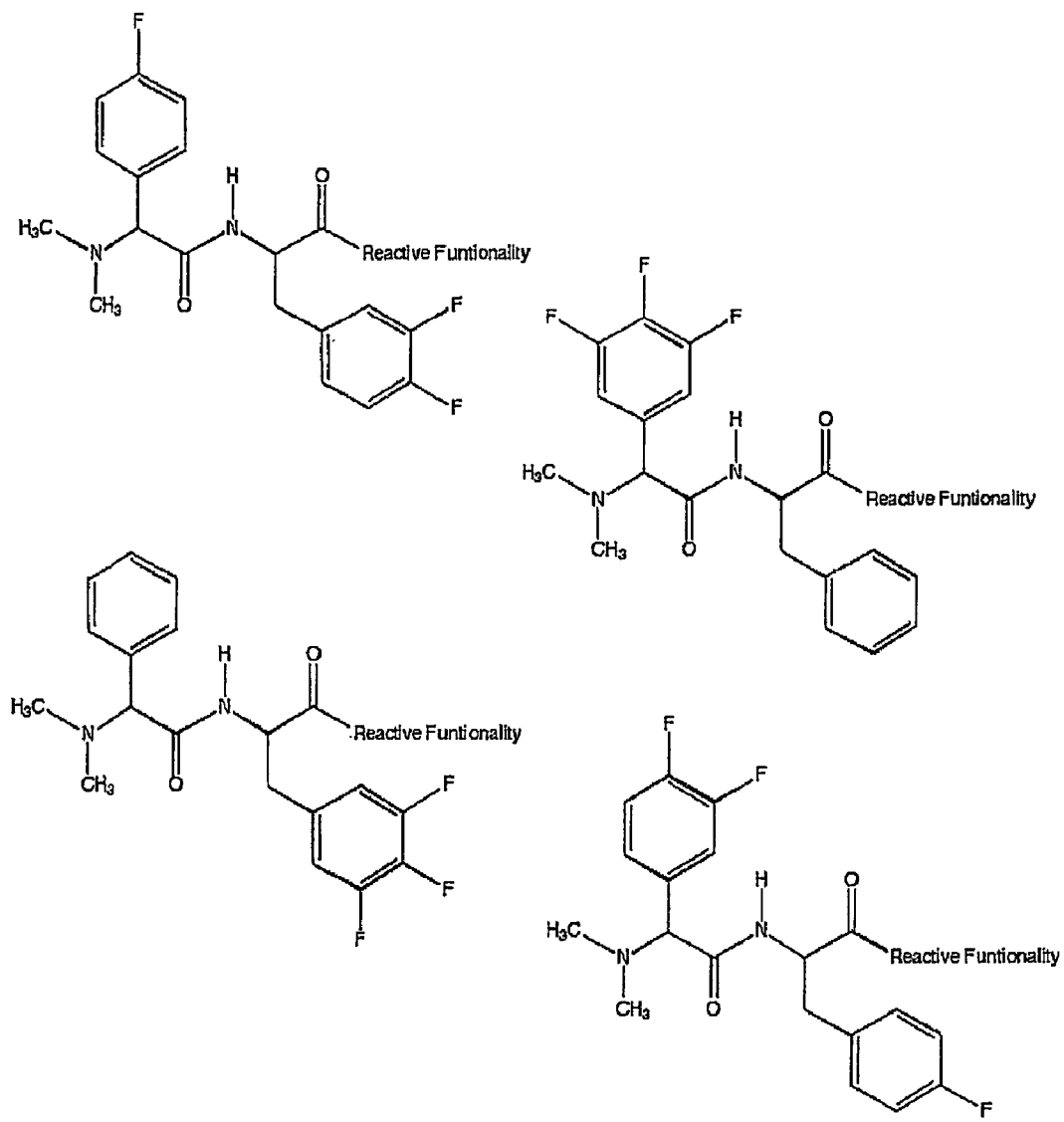
FIG. 5 shows a set of 4 mass tags derived from fluorinated forms of phenylglycine and phenylalanine.

FIGS. 1 to 5 illustrate a number of important features of the tags of this invention. The tags in all of FIGS. 1 to 5 are shown linked to a 'reactive functionality', which could be a linker to an N-hydroxysuccinimide ester for example or any of a number other possibilities some of which are discussed below. FIGS. 1, 2 and 4 show that a number of tags can be generated by combining different mass modified forms of the same amino acid into a series of dipeptides. FIGS. 3 and 5 show sets of tags, which are created by combining different amino acids in heterodimers. FIGS. 1 to 3 illustrate tags, which all have the same total mass and which are chemically identical. These tags differ in the distribution of isotopes in the molecules, while FIGS. 4 and 5 which all have the same total mass but which are not chemically identical, these tags differ in the distribution of fluorine substituents in the tags.

FIG. 1 will now be discussed in more detail. FIG. 1 shows 3 homodimers of lysine. The lysine has been blocked at the epsilon amino groups with methylsulphonyl chloride. The sulphonamide linkage is more resistant to fragmentation than a conventional amide linkage, so that the capping group will not be lost when the tag is fragmented in a mass spectrometer using collision induced dissociation at energies sufficient to cleave the conventional backbone amide bond between the pair of modified lysine residues. The capping group is used to inhibit protonation at the epsilon position during ionisation of the tags in a mass spectrometer. The capped lysine can be prepared prior to synthesis of the mass tags. The epsilon amino group can be selectively modified by coupling the amino acid with methylsulphonyl chloride in the presence of copper ions, for example. Amine and acid functionalities at the alpha position can form chelates with various divalent cations making the alpha amino group unreactive. The alpha-amino group of the dipeptide has been converted to a guanidino-group to promote protonation at this position in the tag during ionisation in a mass spectrometer and to differentiate the mass of the fragmentation product from the second alanine residue and natural alanine residues in protein. The guanidination of the alpha-position can be performed as the last step of a conventional peptide synthesis before deprotection of the peptide and cleavage from the resin (Z. Tian and R. W. Roeske, Int. J. Peptide Protein Res. 37: 425-429, "Guanidination of a peptide side chain amino group on a solid support", 1991). Different deuterated forms of lysine would be used to prepare the three different tags. The total mass of each of the three tags is the same but the N-terminal lysine in each tag differs from the other two by at least four Daltons. This mass difference is usually sufficient to prevent natural isotope peaks from fragmented portions of each tag from overlapping in the mass spectrum with the isotope peaks of the fragmented portions of other tags.

FIG. 2 will now be discussed in more detail. FIG. 2 shows 5 homodimers of alanine. Different isotopically substituted forms of alanine would be used to prepare the five different tags. The total mass of each of the five tags is the same but the N-terminal alanine in each tag differs from the other four by at least one Dalton. The alpha amino group of the dipeptide tag has been methylated to differentiate the fragmentation product of this amino acid from the fragmentation product of the second alanine residue and the natural alanine residues in the protein and to promote protonation at this position in the tag during ionisation in a mass spectrometer.

FIG. 3 will now be discussed in more detail. FIG. 3 shows 5 heterodimers of alanine and tyrosine. Different isotopically substituted forms of alanine and tyrosine would be used to prepare the five different tags. The total mass of each of the five tags is the same but the N-terminal alanine in each tag differs from the other four by at least one dalton. The alpha amino group of the dipeptide tag has been methylated to differentiate the fragmentation product of this amino acid from the fragmentation products of natural alanine residues in the protein and to promote protonation at this position in the tag during ionisation in a mass spectrometer.

FIG. 4 will now be discussed in more detail. FIG. 4 shows 4 dimers of phenylglycine. Different fluorine substituted forms of phenylglycine would be used to prepare the 4 different tags. The total mass of each of the 4 tags is the same but the N-terminal phenylglycine in each tag differs from the other 3 tags by the mass of at least one fluorine atom. The alpha amino group of the dipeptide tag has been methylated to differentiate the fragmentation product of this amino acid from the fragmentation product of the second phenylglycine residue and to promote protonation at this position in the tag during ionisation in a mass spectrometer.

FIG. 5 will now be discussed in more detail. FIG. 5 shows 4 dimers comprising phenylglycine and phenylalanine. Different fluorine substituted forms of phenylglycine and phenylalanine would be used to prepare the 4 different tags. The total mass of each of the 4 tags is the same but the N-terminal alanine in each tag differs from the other 3 tags by the mass of at least one fluorine atom. The alpha amino group of the dipeptide tag has been methylated, although this serves only to protect the amino group from side reactions and to increase protonation as it is not necessary to differentiate the first amino acid as the fragmentation product without methylation would be different from the second amino acid residue of the tag peptide. The alpha amino group could be modified to promote protonation at this position in the tag during ionisation in a mass spectrometer by methylation or guanidination if this is desirable.

The present invention will now be described in more detail. In one preferred embodiment, the present invention provides a set of mass labels as defined above, in which each label in the set has a mass marker moiety having a common mass and each label in the set has a unique aggregate mass.

In an alternative, more preferred embodiment, each label in the set has a common aggregate mass and each label in the set has a mass marker moiety of a unique mass.

The set of labels need not be limited to the two preferred embodiments described above, and may for example comprise labels of both types, provided that all labels are distinguishable by mass spectrometry, as outlined above.

It is preferred that, in a set of labels of the second type, each mass marker moiety in the set has a common basic structure and each mass normalisation moiety in the set has a common basic structure, and each mass label in the set comprises one or more mass adjuster moieties, the mass adjuster moieties being attached to or situated within the basic structure of the mass marker moiety and/or the basic structure of the mass normalisation moiety. In this embodiment, every mass marker moiety in the set comprises a different number of mass adjuster moieties and every mass label in the set has the same number of mass adjuster moieties.

Throughout this description, by common basic structure, it is meant that two or-more moieties share a structure which has substantially the same structural skeleton, backbone or core. This skeleton or backbone may be for example comprise one or more amino acids. Preferably the skeleton comprises a number of amino acids linked by amide bonds. However, other units such as aryl ether units may also be present. The skeleton or backbone may comprise substituents pendent from it, or atomic or isotopic replacements within it, without changing the common basic structure.

Typically, a set of mass labels of the second type referred to above comprises mass labels with the formula:

$$M(A)_y\text{-}L\text{-}X(A)_z$$

wherein M is the mass normalisation moiety, X is the mass marker moiety, A is a mass adjuster moiety, L is the cleavable linker comprising the amide bond, y and z are integers of 0 or greater, and y+z is an integer of 1 or greater. Preferably M is a fragmentation resistant group, L is a linker that is susceptible to fragmentation on collision with another molecule or atom and X is preferably a pre-ionised, fragmentation resistant group. The sum of the masses of M and X is the same for all members of the set. Preferably M and X have the same basic structure or core structure, this structure being modified by the mass adjuster moieties. The mass adjuster moiety ensures that the sum of the masses of M and X in is the same for all mass labels in a set, but ensures that each X has a distinct (unique) mass.

The present invention also encompasses arrays of a plurality of sets of mass labels. The arrays of mass labels of the present invention are not particularly limited, provided that they contain a plurality of sets of mass labels according to the present invention. It is preferred that the arrays comprise two or more, three or more, four or more, or five or more sets of mass labels. Preferably each mass label in the array has either of the following structures:

$$(S)_x\text{-}M(A)_y\text{-}L\text{-}X(A)_z$$

$$M(A)_y\text{-}(S)_x\text{-}L\text{-}X(A)_z$$

wherein S is a mass series modifying group, M is the mass normalisation moiety, X is the mass marker moiety, A is the mass adjuster moiety, L is the cleavable linker comprising the amide bond, x is an integer of 0 or greater, y and z are integers of 0 or greater, and y+z is an integer of 1 or greater. The mass series modifying group separates the masses of the sets from each other. This group may be any type of group, but is preferably an amino acid, or aryl ether group. Sets may be separated in mass by comprising a different number of amino acids in their moieties than other tags from different sets.

Linker Groups

In the discussion above and below reference is made to linker groups which may be used to connect molecules of interest to the mass label compounds of this invention. A variety of linkers is known in the art which may be introduced between the mass labels of this invention and their covalently attached analyte. Some of these linkers may be cleavable. Oligo- or poly-ethylene glycols or their derivatives may be used as linkers, such as those disclosed in Maskos, U. & Southern, E.M. Nucleic Acids Research 20: 1679-1684, 1992. Succinic acid based linkers are also widely used, although these are less preferred for applications involving the labeling of oligonucleotides as they are generally base labile and are thus incompatible with the base mediated de-protection steps used in a number of oligonucleotide synthesisers.

Propargylic alcohol is a bifunctional linker that provides a linkage that is stable under the conditions of oligonucleotide synthesis and is a preferred linker for use with this invention in relation to oligonucleotide applications. Similarly 6-aminohexanol is a useful bifunctional reagent to link appropriately functionalised molecules and is also a preferred linker.

A variety of known cleavable linker groups may be used in conjunction with the compounds of this invention, such as photocleavable linkers. Ortho-nitrobenzyl groups are known as photocleavable linkers, particularly 2-nitrobenzyl esters and 2-nitrobenzylamines, which cleave at the benzylamine bond. For a review on cleavable linkers see Lloyd-Williams et al., Tetrahedron 49, 11065-11133, 1993, which covers a variety of photocleavable and chemically cleavable linkers.

WO 00/02895 discloses the vinyl sulphone compounds as cleavable linkers, which are also applicable for use with this invention, particularly in applications involving the labeling of polypeptides, peptides and amino acids. The content of this application is incorporated by reference.

WO 00/02895 discloses the use of silicon compounds as linkers that are cleavable by base in the gas phase. These linkers are also applicable for use with this invention, particularly in applications involving the labeling of oligonucleotides. The content of this application is incorporated by reference.

It has been mentioned above that the mass labels of the present invention may comprise reactive functionalities, Re, to help attach them to analytes. In preferred embodiments of the present invention, Re is a reactive functionality or group which allows the mass label to be reacted covalently to an appropriate functional group in an analyte molecule, such as, but not limited to, a nucleotide oligonucleotide, polynucleotide, amino acid, peptide or polypeptide. Re may be attached to the mass labels via a linker which may or may not be cleavable. A variety of reactive functionalities may be introduced into the mass labels of this invention.

Table 1 below lists some reactive functionalities that may be reacted with nucleophilic functionalities which are found in biomolecules to generate a covalent linkage between the two entities. For applications involving synthetic oligonucleotides, primary amines or thiols are often introduced at the termini of the molecules to permit labeling. Any of the functionalities listed below could be introduced into the compounds of this invention to permit the mass markers to be attached to a molecule of interest. A reactive functionality can be used to introduce a further linker groups with a further reactive functionality if that is desired. Table 1 is not intended to be exhaustive and the present invention is not limited to the use of only the listed functionalities.

TABLE 1

| Nucleophilic Functionality | Reactive Functionality | Resultant Linking Group |
|---|---|---|
| —SH | —SO$_2$—CH═CR$_2$ | —S—CR$_2$—CH$_2$—SO$_2$— |
| —NH$_2$ | —SO$_2$—CH═CR$_2$ | —N(CR$_2$—CH$_2$—SO$_2$—)$_2$ or —NH—CR$_2$—CH$_2$—SO$_2$— |
| —NH$_2$ | 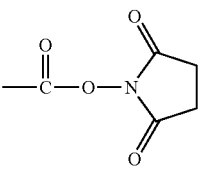 | —CO—NH— |

TABLE 1-continued

| Nucleophilic Functionality | Reactive Functionality | Resultant Linking Group |
|---|---|---|
| $-NH_2$ |  | $-CO-NH-$ |
| $-NH_2$ | $-NCO$ | $-NH-CO-NH-$ |
| $-NH_2$ | $-NCS$ | $-NH-CS-NH-$ |
| $-NH_2$ | $-CHO$ | $-CH_2-NH-$ |
| $-NH_2$ | $-SO_2Cl$ | $-SO_2-NH-$ |
| $-NH_2$ | $-CH=CH-$ | $-NH-CH_2-CH_2-$ |
| $-OH$ | $-OP(NCH(CH_3)_2)_2$ | $-OP(=O)(O)O-$ |

It should be noted that in applications involving labeling oligonucleotides with the mass markers of this invention, some of the reactive functionalities above or their resultant linking groups might have to be protected prior to introduction into an oligonucleotide synthesiser. Preferably unprotected ester, thioether and thioesters, amine and amide bonds are to be avoided, as these are not usually stable in an oligonucleotide synthesiser. A wide variety of protective groups is known in the art which can be used to protect linkages from unwanted side reactions.

In the discussion below reference is made to "charge carrying functionalities" and solubilising groups. These groups may be introduced into the mass labels such as in the mass markers of the invention to promote ionisation and solubility. The choice of markers is dependent on whether positive or negative ion detection is to be used. Table 2 below lists some functionalities that may be introduced into mass markers to promote either positive or negative ionisation. The table is not intended as an exhaustive list, and the present invention is not limited to the use of only the listed functionalities.

TABLE 2

| Positive Ion Mode | Negative Ion Mode |
|---|---|
| $-NH_2$ | $-SO_3^-$ |
| $-NR_2$ | $-PO_4^-$ |
| $-NR_3^+$ | $-PO_3^-$ |
| 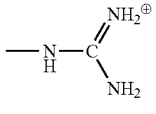 | $-CO_2^-$ |
| 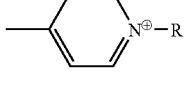 | |
| $-SR_2^+$ | |

WO 00/02893 discloses the use of metal-ion binding moieties such as crown-ethers or porphyrins for the purpose of improving the ionisation of mass markers. These moieties are also be applicable for use with the mass markers of this invention.

The components of the mass markers of this invention are preferably fragmentation resistant so that the site of fragmentation of the markers can be controlled by the introduction of a linkage that is easily broken by Collision Induced Dissociation (CID). Aryl ethers are an example of a class of fragmentation resistant compounds that may be used in this invention. These compounds are also chemically inert and thermally stable. WO 99/32501 discusses the use of poly-ethers in mass spectrometry in greater detail and the content of this application is incorporated by reference.

In the past, the general method for the synthesis of aryl ethers was based on the Ullmann coupling of arylbromides with phenols in the presence of copper powder at about 200° C. (representative reference: H. Stetter, G. Duve, Chemische Berichte 87 (1954) 1699).

Milder methods for the synthesis of aryl ethers have been developed using a different metal catalyst but the reaction temperature is still between 100 and 120° C. (M. Iyoda, M. Sakaitani, H. Otsuka, M. Oda, Tetrahedron Letters 26 (1985) 477). This is a preferred route for the production of poly-ether mass labels. See synthesis of FT77 given in the examples below. A recently published method provides a most preferred route for the generation of poly-ether mass labels as it is carried out under much milder conditions than the earlier methods (D. E. Evans, J. L. Katz, T. R. West, Tetrahedron Lett. 39 (1998) 2937).

The present invention also provides a set of two or more probes, each probe in the set being different and being attached to a unique mass label or a unique combination of mass labels, from a set or an array of mass labels as defined as defined above.

Further provided is an array of probes comprising two or more sets of probes, wherein each probe in any one set is attached to a unique mass label, or a unique combination of mass labels, from a set of mass labels as defined above, and wherein the probes in any one set are attached to mass labels from the same set of mass labels, and each set of probes is attached to mass labels from unique sets of mass labels from an array of mass labels as defined above.

In one embodiment, each probe is preferably attached to a unique combination of mass labels, each combination being distinguished by the presence or absence of each mass label in the set of mass labels and/or the quantity of each mass label attached to the probe. This is termed the "mixing mode" of the present invention, since the probes may be attached to a mixture of mass labels.

In the above aspects, the nature of the probe is not particularly limited. However, preferably each probe comprises a biomolecule. Any biomolecule can be employed, but the biomolecule is preferably selected from a DNA, an RNA, an oligonucleotide, a nucleic acid base, a peptide, a polypeptide, a protein and an amino acid.

In one preferred embodiment, this invention provides sets and arrays of mass labeled analytes, such as nucleotides, oligonucleotides and polynucleotides, of the form:

analyte-linker-label

Wherein the linker is a linker as defined above, and label is a mass label from any of the sets and arrays defined above.

In the above aspect, the nature of the analyte is not particularly limited. However, preferably each analyte comprises a biomolecule. Any biomolecule can be employed, but the biomolecule is preferably selected from a DNA, an RNA, an oligonucleotide, a nucleic acid base, a peptide, a polypeptide, a protein and an amino acid.

In one embodiment, each analyte is preferably attached to a unique combination of mass labels, each combination being distinguished by the presence or absence of each mass label in the set of mass labels and/or the quantity of each mass label attached to the probe. As mentioned above, this is termed the "mixing mode" of the present invention, since the probes may be attached to a mixture of mass labels.

As mentioned above, the present invention provides a method of analysis, which method comprises detecting an analyte by identifying by mass spectrometry a mass label or a combination of mass labels unique to the analyte, wherein the mass label is a mass label from a set or an array of mass labels as defined above. The type of method is not particularly limited, provided that the method benefits from the use of the mass labels of the present invention to identify an analyte. The method may be, for example, a method of sequencing nucleic acid or a method of profiling the expression of one or more genes by detecting quantities of protein in a sample. The method is especially advantageous, since it can be used to readily analyse a plurality of analytes simultaneously. However, the method also has advantages for analysing single analytes individually, since using the present mass labels, mass spectra which are cleaner than conventional spectra are produced, making the method accurate and sensitive.

In a further preferred embodiment, the present invention provides a method which method comprises:

(a) contacting one or more analytes with a set of probes, or an array of probes, each probe in the set or array being specific to at least one analyte, wherein the probes are as defined above, (b) identifying an analyte, by detecting the probe specific to that analyte.

In this embodiment it is preferred that the mass label is cleaved from the probe prior to detecting the mass label by mass spectrometry.

The nature of the methods of this particular embodiment is not especially limited. However, it is preferred that the method comprises contacting one or more nucleic acids with a set of hybridisation probes. The set of hybridisation probes typically comprises a set of up to 256 4-mers, each probe in the set having a different combination of nucleic acid bases. This method may be suitable for identifying the presence of target nucleic acids, or alternatively can be used in a stepwise method of primer extension sequencing of one or more nucleic acid templates.

The mass labels of the present invention are particularly suitable for use in methods of 2-dimensional analysis, primarily due to the large number of labels that can be simultaneously distinguished. The labels may thus be used in a method of 2-dimensional gel electrophoresis, or in a method of 2-dimensional mass spectrometry.

Peptide Synthesis

The synthesis of many examples of the peptide mass tags of this invention will be possible using conventional peptide synthesis methods and commercially available reagents. Modified amino acids that are not commercially available are also contemplated for the synthesis of further peptide mass tags.

Modern peptide synthesis is typically carried out on solid phase supports in automated synthesiser instruments, which deliver all the necessary reagents for each step of a peptide synthesis to the solid support and remove spent reagents and unreacted excess reagents at the end of each step in the cycle. Solid phase peptide synthesis is, however, often performed manually, particularly when specialist reagents are being tested for the first time. In essence peptide synthesis involves the addition of N-protected amino acids to the solid support. The peptide is normally synthesised with the C-terminal carboxyl group of the peptide attached to the support, and the sequence of the peptide is built from the C-terminal amino acid to the N-terminal amino acid. The C-terminal amino acid is coupled to the support by a cleavable linkage. The N-protected alpha amino group of each amino acid is deprotected to allow coupling of the carboxyl group of the next amino acid to the growing peptide on the solid support. For most purposes, peptide synthesis is performed by one of two different synthetic procedures, which are distinguished by the conditions needed to remove the N-protecting group. The tert-butyloxycarbonyl (t-BOC) group is cleaved by mildly acidic conditions, e.g. trifluoroacetic acid in dichloromethane, while the fluorenylmethoxycarbonyl (FMOC) group is cleaved by mildly basic conditions, e.g. 20% piperidine in dimethylformamide. Reactive side chains in amino acids also need protection during cycles of amide bond formation. These side chains include the epsilon amino group of lysine, the guanidino side-chain of arginine, the thiol functionality of cysteine, the hydroxyl functionalities of serine, threonine and tyrosine, the indole ring of tryptophan and the imidazole ring of histidine. The choice of protective groups used for side-chain protection is determined by the cleavage conditions of the alpha-amino protection groups, as the side-chain protection groups must be resistant to the deprotection conditions used to remove the alpha-amino protection groups. A first protective group is said to be 'orthogonal' to a second protective group if the first protective group is resistant to deprotection under the conditions used for the deprotection of the second protective group and if the deprotection conditions of the first protecting group do not cause deprotection of the second protecting group.

Examples of side-chain protection groups compatible with FMOC syntheses are shown in Table 3.

TABLE 3

| Side Chain | Protective Group |
| --- | --- |
| Epsilon amino group of lysine | t-BOC group |
| Guanidino-functionality of arginine | Nitro group or 2,2,5,7,8-pentamethylchroman-6-sulphonyl group |
| Imidazole ring of histidine | τ-Trityl group, π-benzyloxymethyl (Bom) group. |
| Hydroxyl functionalities of serine, threonine and tyrosine | Tert-butyl group |
| Indole ring of tryptophan | t-BOC |
| Thiol functionality of cysteine | trityl or benzyl group |
| Amide functionalities of glutamine and asparagine | Not usually necessary but Trityl group can be used for example. |
| Carboxylic acid functionalities of glutamic acid and aspartic acid. | Tert-butyl group |
| Thioether of methionine | Sometimes protected as sulphoxide |

Other side-chain protective groups that are orthogonal to FMOC protection will be known to one of ordinary skill in the art and may be applied with this invention (see for example Fields G. B. & Noble R. L., Int J Pept Protein Res 35(3): 161-214, "Solid phase peptide synthesis utilizing 9-fluorenylmethoxycarbonyl amino acids." 1990).

Protection groups for reactive side-chain functionalities compatible with t-BOC synthesis are shown below in Table 4.

TABLE 4

| Side Chain | Protective Group |
| --- | --- |
| Epsilon amino group of lysine | Benzyloxycarbonyl (Z) group |
| Guanidino-functionality of arginine | Not usually necessary but nitration can be used |
| Imidazole ring of histidine | π-benzyloxymethyl (Bom) group. |
| Hydroxyl functionalities of serine, threonine and tyrosine | Benzyl group |

TABLE 4-continued

| Side Chain | Protective Group |
|---|---|
| Hydroxyl functionality of tyrosine | 2-Bromobenzyloxycarbonyl group |
| Indole ring of tryptophan | Not usually necessary |
| Thiol functionality of cysteine | Benzyl group |
| Amide functionalities of glutamine and asparagine | Not usually necessary |
| Carboxylic acid functionalities of glutamic acid and aspartic acid. | Benzyl ester group |
| Thioether of methionine | Sometimes protected as sulphoxide |

Again, the practitioner of ordinary skill in the art will be aware of other protective groups for use with reactive side chains that are orthogonal to t-BOC alpha amino protection. Various different solid supports and resins are commercially available for peptide synthesis using either the FMOC or t-BOC procedures (for a review of solid supports see Meldal. M., Methods Enzymol 289: 83-104, "Properties of solid supports." 1997).

Mass Modified Amino Acids

A variety of amino acids can be used in the mass marker moiety and the mass normalisation moiety. Neutral amino acids are preferred in the mass normalisation moiety and charged amino acids are preferred in the mass marker moieties (since this facilitates ionisation and increases sensitivity) e.g. in the position marked amino acid 1 and amino acid 2 in the first and fourth embodiments of this invention. A number of commercially available isotopically mass modified amino acids are shown in Table 5 below. Any combination of 1, 2, 3, or 4 or more amino acids from this list are preferred in each of the moieties according to the present invention.

TABLE 5

| Amino acid | Isotope Forms |
|---|---|
| Alanine | $CH_3CH(NH_2)^{13}CO_2H$, $CH_3CD(NH_2)CO_2H$, $CH_3{}^{13}CH(^{15}NH_2)CO_2H$, $CD_3CH(NH_2)CO_2H$, $CD_3CD(NH_2)CO_2H$, $CD_3CH(NH_2)^{13}CO_2H$, $CD_3{}^{13}CH(NH_2)CO_2H$, $^{13}CH_3{}^{13}CH(^{15}NH_2)^{13}CO_2H$ |
| Arginine | $[(^{15}NH_2)_2CNHCH_2CH_2CH(NH_2)CO_2H]^+$ |
| Asparagine | $H_2N^{13}COCH_2CH(NH_2)CO_2H$, $H_2N^{13}CO^{13}CH_2{}^{13}CH(NH_2)^{13}CO_2H$, $H_2{}^{15}NCOCH_2CH(NH_2)CO_2H$, $H_2{}^{15}NCOCH_2CH(^{15}NH_2)CO_2H$, |
| Aspartic Acid | $HO_2{}^{13}CCH_2CH(NH_2)CO_2H$, $HO_2C^{13}CH_2CH(NH_2)CO_2H$, $HO_2CCH_2CH(NH_2)^{13}CO_2H$, $HO_2{}^{13}CCH_2CH(NH_2)^{13}CO_2H$, $HO_2CCH_2{}^{13}CH(NH_2)^{13}CO_2H$, $HO_2{}^{13}C^{13}CH_2CH(NH_2)CO_2H$, $HO_2{}^{13}C^{13}CH_2{}^{13}CH(NH_2)^{13}CO_2H$, $HO_2CCD_2CD(NH_2)CO_2H$, $HO_2CCH_2CH(^{15}NH_2)CO_2H$, $HO_2CCH_2CH(^{15}NH_2)^{13}CO_2H$ |
| Cysteine | Not available |
| Gluatamic Acid | $HO_2CCH_2CH_2CH(NH_2)^{13}CO_2H$, $HO_2CCH_2CH_2{}^{13}CH(NH_2)CO_2H$, $HO_2CCH_2{}^{13}CH_2CH(NH_2)CO_2H$, $HO_2C^{13}CH_2CH_2CH(NH_2)CO_2H$, $HO_2{}^{13}CCH_2CH_2CH(NH_2)CO_2H$, $HO_2{}^{13}C^{13}CH_2{}^{13}CH_2{}^{13}CH(NH_2)^{13}CO_2H$, $HO_2CCD_2CH_2CH(NH_2)CO_2H$, $HO_2CCD_2CD_2CD(NH_2)CO_2H$, $HO_2{}^{13}C^{13}CH_2{}^{13}CH_2{}^{13}CH(^{15}NH_2)^{13}CO_2H$ |
| Glutamine | $H_2NCOCH_2CH_2CH(NH_2)^{13}CO_2H$, $H_2N^{13}COCH_2CH_2CH(NH_2)CO_2H$, $H_2NCOCD_2CD_2CD(NH_2)CO_2H$, $H_2{}^{15}NCOCH_2CH_2CH(NH_2)CO_2H$, $H_2NCOCH_2CH_2CH(^{15}NH_2)CO_2H$, $H_2{}^{15}NCOCH_2CH_2CH(^{15}NH_2)CO_2H$, $H_2{}^{15}N^{13}CO^{13}CH_2{}^{13}CH_2{}^{13}CH(^{15}NH_2)^{13}CO_2H$ |
| Glycine | $H_2NCH_2{}^{13}CO_2H$, $H_2N^{13}CH_2CO_2H$, $H_2N^{13}CH_2{}^{13}CO_2H$, $H_2NCD_2CO_2H$, $H_2{}^{15}NCH_2CO_2H$, $H_2{}^{15}N^{13}CH_2CO_2H$, $H_2{}^{15}NCH_2{}^{13}CO_2H$, $H_2{}^{15}N^{13}CH_2{}^{13}CO_2H$ |
| Histidine | $(CH)_2N_2CCH_2CH(NH_2)^{13}CO_2H$, $(CH)_2N_2CCH_2CH(^{15}NH_2)CO_2H$, $(CH)_2{}^{15}N_2CCH_2CH(NH_2)CO_2H$ |
| Isoleucine | Not available |
| Leucine | $(CH_3)_2CHCH_2CH(NH_2)^{13}CO_2H$, $(CH_3)_2CHCH_2{}^{13}CH(NH_2)CO_2H$, $(CH_3)_2CHCH_2{}^{13}CH(NH_2)^{13}CO_2H$, $(CH_3)_2CHCH_2CD(NH_2)CO_2H$, $(CH_3)_2CHCD_2CD(NH_2)CO_2H$, $(CD_3)(CH_3)CHCH_2CH(NH_2)CO_2H$, $(CD_3)_2CDCH_2CH(NH_2)CO_2H$, $(CD_3)_2CDCD_2CD(NH_2)CO_2H$, $(CH_3)_2CHCH_2CH(^{15}NH_2)CO_2H$, $(CH_3)_2CHCH_2CH(^{15}NH_2)^{13}CO_2H$ |
| Lysine | $H_2NCH_2CH_2CH_2CH_2CH(NH_2)^{13}CO_2H$, $H_2NCH_2CH_2CH_2CH_2{}^{13}CH(NH_2)CO_2H$, $H_2N^{13}CH_2CH_2CH_2CH_2CH(NH_2)CO_2H$, $H_2NCH_2CH_2CH_2CH_2{}^{13}CH(NH_2)^{13}CO_2H$, $H_2NCH_2CD_2CD_2CH_2CH(NH_2)CO_2H$, $H_2NCD_2CD_2CD_2CD_2CH(NH_2)CO_2H$, $H_2NCH_2CH_2CH_2CH_2CH(^{15}NH_2)CO_2H$, $H_2{}^{15}NCH_2CH_2CH_2CH_2CH(NH_2)CO_2H$, $H_2{}^{15}N^{13}CH_2CH_2CH_2CH_2CH(NH_2)CO_2H$ |
| Methionine | $CH_3SCH_2CH_2CH(NH_2)^{13}CO_2H$, $CH_3SCH_2CH_2{}^{13}CH(NH_2)CO_2H$, $^{13}CH_3SCH_2CH_2CH(NH_2)CO_2H$, $CH_3SCH_2CH_2CD(NH_2)CO_2H$, $CD_3SCH_2CH_2CH(NH_2)CO_2H$, $CH_3SCH_2CH_2CH(^{15}NH_2)CO_2H$, $^{13}CD_3SCH_2CH_2CH(NH_2)CO_2H$, $CH_3SCH_2CH_2{}^{13}CH(^{15}NH_2)CO_2H$ |
| Phenyl-alanine | $C_6H_5CH_2CH(NH_2)^{13}CO_2H$, $C_6H_5CH_2{}^{13}CH(NH_2)CO_2H$, $^{13}C_6H_5CH_2CH(NH_2)CO_2H$, $C_6H_5CH_2CD(NH_2)CO_2H$, $C_6H_5CD_2CH(NH_2)CO_2H$, $C_6D_5CH_2CH(NH_2)CO_2H$, $C_6D_5CD_2CD(NH_2)CO_2H$, $C_6H_5CH_2CH(^{15}NH_2)CO_2H$ |
| Proline | 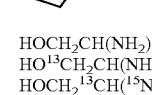 |
| Serine | $HOCH_2CH(NH_2)^{13}CO_2H$, $HOCH_2{}^{13}CH(NH_2)CO_2H$, $HO^{13}CH_2CH(NH_2)CO_2H$, $HOCH_2CH(^{15}NH_2)CO_2H$, $HOCH_2{}^{13}CH(^{15}NH_2)CO_2H$ |
| Threonine | $CH_3CH(OH)CH(NH_2)^{13}CO_2H$ |
| Tryptophan | 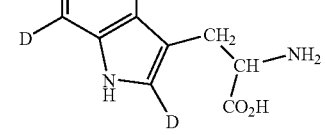 |

TABLE 5-continued

| Amino acid | Isotope Forms |
|---|---|
| Tyrosine | $HO(C_6H_4)CH_2CH(NH_2)^{13}CO_2H$, |
| | $HO(C_6H_4)CH_2{}^{13}CH(NH_2)CO_2H$, |
| | $HO(C_6H_4)^{13}CH_2CH(NH_2)CO_2H$, |
| | $HO(C_6H_4)^{13}CH_2{}^{13}CH(NH_2)^{13}CO_2H$, |
| | $HO(^{13}C_6H_4)CH_2CH(NH_2)CO_2H$, |
| | $HO(^{13}C_6H_4)^{13}CH_2{}^{13}CH(NH_2)^{13}CO_2H$, |
| | $HO(C_6H_4)CD_2CH(NH_2)CO_2H$, |
| | $HO(C_6D_2H_2)CH_2CH(NH_2)CO_2H$, |
| | $HO(C_6D_4)CH_2CH(NH_2)CO_2H$, |
| | $HO(C_6H_4)CH_2CH(^{15}NH_2)CO_2H$, |
| | $H^{17}O(C_6H_4)CH_2CH(NH_2)CO_2H$, |
| | $H^{18}O(C_6H_4)CH_2CH(NH_2)CO_2H$, |
| | $HO(C_6H_4)CH_2{}^{13}CH(^{15}NH_2)CO_2H$, |
| | $HO(^{13}C_6H_4)^{13}CH_2{}^{13}CH(^{15}NH_2)^{13}CO_2H$ |
| Valine | $(CH_3)_2CHCH(NH_2)^{13}CO_2H$, $(CH_3)_2CH^{13}CH(NH_2)CO_2H$, |
| | $(CH_3)_2CHCD(NH_2)CO_2H$, $(CD_3)_2CDCD(NH_2)CO_2H$, |
| | $(CH_3)_2CHCH(^{15}NH_2)CO_2H$ |

For many of the above amino acids, both the D- and L-forms are available (from ISOTEC Inc., Miamisburg, Ohio for example), either of which may be used in the preparation of the tags of this invention. Mixtures of D and L forms are also available but are less preferred if the tags of this invention are to be used in chromatographic separations. For some, FMOC or t-BOC protected derivatives are also available. Mass modified amino acids based on substitution of deuterium for hydrogen and on substitution of $^{13}C$ and $^{15}N$ isotopes for $^{12}C$ and $^{13}N$ isotopes are also available and are equally applicable for the synthesis of the tags of this invention. Various amino acids that are not typically found in peptides may also be used in the tags of this invention, for example deuterated forms of amino-butyric acid are commercially available. For the purposes of this invention non-radioactive, stable isotopes are preferred for safety reasons but there is no necessary limitation to stable isotopes.

Fluorinated derivatives of a number of amino acids are also available. Some of the commercially available fluorinated amino acids are shown in Table 6 below.

TABLE 6

| Amino acid | Fluorinated Forms |
|---|---|
| Glutamic Acid | $HO_2CCFHCH_2CH(NH_2)CO_2H$ |
| Leucine | $(CH_3)(CF_3)CHCH_2CH(NH_2)CO_2H$ |
| Phenylalanine | $C_6FH_4CH_2CH(NH_2)CO_2H$, $C_6F_2H_3CH_2CH(NH_2)CO_2H$, |
| | $C_6F_3H_2CH_2CH(NH_2)CO_2H$ |
| Phenylglycine | $C_6FH_4CH(NH_2)CO_2H$, $C_6F_2H_3CH(NH_2)CO_2H$, |
| | $C_6F_3H_2CH(NH_2)CO_2H$ |
| Valine | $(CH_3)_2CFCH(NH_2)CO_2H$ |

For most of the above fluorinated amino acids, the reagents are available as mixtures of D and L forms. In general, fluorinated variants of amino acids are less preferred than isotope substituted variants. The fluorinated compounds can be used to generate a range of mass tags with the same mass but each tag will be chemically different, which means that their behaviour in the mass spectrometer will vary more than isotope substituted tags. Moreover, the tags will not have identical chromatographic properties if the tags are to be used in chromatographic separations.

Reactive Functionalities

In some aspects of this invention, as already explained, the mass tags of the invention comprise a reactive functionality. In the simplest embodiments this may be an N-hydroxysuccinimide ester introduced by activation of the C-terminus of the tag peptides of this invention. In conventional peptide synthesis, this activation step would have to take place after the peptide mass tag has been cleaved from the solid support used for its synthesis. An N-hydroxysuccinimide activated peptide mass tag could also be reacted with hydrazine to give a hydrazide reactive functionality, which can be used to label periodate oxidised sugar moieties, for example. Aminogroups or thiols can be used as reactive functionalities in some applications and these may be introduced by adding lysine or cysteine after amino acid 2 of the tag peptide. Lysine can be used to couple tags to free carboxyl functionalities using a carbodiimide as a coupling reagent. Lysine can also be used as the starting point for the introduction of other reactive functionalities into the tag peptides of this invention. The thiol-reactive maleimide functionality can be introduced by reaction of the lysine epsilon amino group with maleic anhydride. The cysteine thiol group can be used as the starting point for the synthesis of a variety of alkenyl sulphone compounds, which are useful protein labeling reagents that react with thiols and amines. Compounds such as aminohexanoic acid can be used to provide a spacer between the mass modified amino acids and the reactive functionality.

Affinity Capture Ligands

In certain embodiments of the first aspect of this invention the mass markers comprise an affinity capture ligand. Affinity capture ligands are ligands, which have highly specific binding partners. These binding partners allow molecules tagged with the ligand to be selectively captured by the binding partner. Preferably a solid support is derivitised with the binding partner so that affinity ligand tagged molecules can be selectively captured onto the solid phase support. A preferred affinity capture ligand is biotin, which can be introduced into the peptide mass tags of this invention by standard methods known in the art. In particular a lysine residue may be incorporated after amino acid 2 through which an amine-reactive biotin can be linked to the peptide mass tags ( see for example Geahlen R. L. et al., Anal Biochem 202(1): 68-67, "A general method for preparation of peptides biotinylated at the carboxy terminus." 1992; Sawutz D. G. et al., Peptides 12(5): 1019-1012, "Synthesis and molecular characterization of a biotinylated analog of [Lys]bradykinin." 1991; Natarajan S. et al., Int J Pept Protein Res 40(6): 567-567, "Site-specific biotinylation. A novel approach and its application to endothelin-1 analogs and PTH-analog.", 1992). Iminobiotin is also applicable. A variety of avidin counter-ligands for biotin are available, which include monomeric and tetrameric avidin and streptavidin, all of which are available on a number of solid supports.

Other affinity capture ligands include digoxigenin, fluorescein, nitrophenyl moieties and a number of peptide epitopes, such as the c-myc epitope, for which selective monoclonal antibodies exist as counter-ligands. Metal ion binding ligands such as hexahistidine, which readily binds $Ni^{2+}$ ions, are also applicable. Chromatographic resins, which present iminodiacetic acid chelated $Ni^{2+}$ ions are commercially available, for example. These immobilised nickel columns may be used to capture peptide mass tags, which comprise oligomeric histidine. As a further alternative, an affinity capture functionality may be selectively reactive with an appropriately derivitised solid phase support. Boronic acid, for example, is known to selectively react with vicinal cis-diols and chemically similar ligands, such as salicylhydroxamic acid. Reagents comprising boronic acid have been developed for protein capture onto solid supports derivitised with salicylhydroxamic acid (Stolowitz M. L. et al., Bioconjug Chem 12(2): 229-239, "Phenylboronic Acid-Salicylhydroxamic Acid Bioconjugates. 1. A Novel Boronic Acid Complex for Protein Immobilization." 2001; Wiley J. P. et al., Bioconjug Chem 12(2): 240-250, "Phenylboronic Acid-Salicylhydroxamic Acid Bioconjugates. 2. Polyvalent Immobilization of Protein Ligands for Affinity Chromatography." 2001, Prolinx, Inc, Washington State, USA). It is anticipated that it should be relatively simple to link a phenylboronic acid functionality to a peptide mass tag according to this invention to generate capture reagents that can be captured by selective chemical reactions. The use of this sort of chemistry would not be directly compatible with biomolecules bearing vicinal cis-diol-containing sugars, however these sorts of sugars could be blocked with phenylboronic acid or related reagents prior to reaction with boronic acid derivitised peptide mass tag reagents.

Mass Spec Sensitivity Enhancing Groups and Mass Differentiation

In preferred embodiments of the first and fourth aspects of this invention the peptide mass tags comprise Sensitivity Enhancing Groups. FIGS. 1 to 5 illustrate the use of methylation and guanidination as methods of improving sensitivity. In addition, these Sensitivity Enhancing Groups can differentiate the fragmentation products of the N-terminal amino acid from the fragmentation products of the second amino acid in the peptide tag and natural amino acid residues in the protein, if this is the same as the first amino acid. The sensitivity enhancing group can also distinguish the fragmentation products of the N-terminal amino acid of the peptide mass tag from the fragmentation products of natural amino acids when the tags of this invention are used to label peptides and proteins. The guanidino group and the tertiary amino group are both useful Sensitivity Enhancing Groups for electrospray mass spectrometry.

Various other methods for derivatising peptides have been also been developed. These include the use of quaternary ammonium derivatives, quaternary phosphonium derivatives and pyridyl derivatives for positive ion mass spectrometry. Halogenated compounds, particularly halogenated aromatic compounds are well known electrophores, i.e. they pick up thermal electrons very easily. A variety of derivatisation reagents based on fluorinated aromatic compounds (Bian N. et al., Rapid Commun Mass Spectrom 11(16): 1781-1784, "Detection via laser desorption and mass spectrometry of multiplex electrophore-labeled albumin." 1997) have been developed for electron capture detection, which is a highly sensitive ionisation and detection process that can be used with negative ion mass spectrometry (Abdel-Baky S. & Giese R. W., Anal Chem 63(24):2986-2989, "Gas chromatography/electron capture negative-ion mass spectrometry at the zeptomole level." 1991). A fluorinated aromatic group could also be used as a sensitivity enhancing group. Aromatic sulphonic acids have also been used for improving sensitivity in negative ion mass spectrometry.

Each type of Sensitivity Enhancing Group has different benefits, which depend on the method of ionisation used and on the methods of mass analysis used. The mechanism by which sensitivity is enhanced may also be different for each type of group. Some derivitisation methods increase basicity and thus promote protonation and charge localisation, while other methods increase surface activity of the tagged peptides, which improves sensitivity in surface desorption techniques like Matrix Assisted Laser Desorption Ionisation (MALDI) and Fast Atom Bombardment (FAB). Negative ion mass spectrometry is often more sensitive because there is less background noise. Charge derivitisation can also change the fragmentation products of derivatised peptides, when collision induced dissociation is used. In particular some derivatisation techniques simplify fragmentation patterns, which is highly advantageous. The choice of Sensitivity Enhancing Group is determined by the mass spectrometric techniques that will be employed (for a review see Roth et al., Mass Spectrometry Reviews 17:255-274, "Charge derivatisation of peptides for analysis by mass spectrometry", 1998). For the purposes of this invention all of the known derivatisation techniques could be used with the peptide mass tags of this invention. The published protocols could be used without modification to derivitise the peptide mass tags of this invention after solid phase peptide synthesis or the protocols could be readily adapted for use during solid phase synthesis if desired.

Analysis of Peptides by Mass Spectrometry

The essential features of a mass spectrometer are as follows:

Inlet System->Ion Source->Mass Analyser->Ion Detector->Data Capture System

There are preferred inlet systems, ion sources and mass analysers for the purposes of analysing peptides.

Inlet Systems

In the second aspect of this invention a chromatographic or electrophoretic separation is preferred to reduce the complexity of the sample prior to analysis by mass spectrometry. A variety of mass spectrometry techniques are compatible with separation technologies particularly capillary zone electrophoresis and High Performance Liquid Chromatography (HPLC). The choice of ionisation source is limited to some extent if a separation is required as ionisation techniques such as MALDI and FAB (discussed below) which ablate material from a solid surface are less suited to chromatographic separations. For most purposes, it has been very costly to link a chromatographic separation in-line with mass spectrometric analysis by one of these techniques. Dynamic FAB and ionisation techniques based on spraying such as electrospray, thermospray and APCI are all readily compatible with in-line chromatographic separations and equipment to perform such liquid chromatography mass spectrometry analysis is commercially available.

Ionisation Techniques

For many biological mass spectrometry applications so called 'soft' ionisation techniques are used. These allow large molecules such as proteins and nucleic acids to be ionised essentially intact. The liquid phase techniques allow large biomolecules to enter the mass spectrometer in solutions with mild pH and at low concentrations. A number of techniques are appropriate for use with this invention including but not limited to Electrospray Ionisation Mass Spectrometry (ESI-MS), Fast Atom Bombardment (FAB), Matrix Assisted Laser Desorption Ionisation Mass Spectrometry (MALDI MS) and Atmospheric Pressure Chemical Ionisation Mass Spectrometry (APCI-MS).

Electrospray Ionisation

Electrospray ionisation requires that the dilute solution of the analyte molecule is 'atomised' into the spectrometer, i.e. injected as a fine spray. The solution is, for example, sprayed from the tip of a charged needle in a stream of dry nitrogen and an electrostatic field. The mechanism of ionisation is not fully understood but is thought to work broadly as follows. In a stream of nitrogen the solvent is evapourated. With a small droplet, this results in concentration of the analyte molecule. Given that most biomolecules have a net charge this increases the electrostatic repulsion of the dissolved molecule. As evapouration continues this repulsion ultimately becomes greater than the surface tension of the droplet and the droplet disintegrates into smaller droplets. This process is sometimes referred to as a 'Coulombic explosion'. The electrostatic field helps to further overcome the surface tension of the droplets and assists in the spraying process. The evapouration continues from the smaller droplets which, in turn, explode iteratively until essentially the biomolecules are in the vapour phase, as is all the solvent. This technique is of particular importance in the use of mass labels in that the technique imparts a relatively small amount of energy to ions in the ionisation process and the energy distribution within a population tends to fall in a narrower range when compared with other techniques. The ions are accelerated out of the ionisation chamber by the use of electric fields that are set up by appropriately positioned electrodes. The polarity of the fields may be altered to extract either negative or positive ions. The potential difference between these electrodes determines whether positive or negative ions pass into the mass analyser and also the kinetic energy with which these ions enter the mass spectrometer. This is of significance when considering fragmentation of ions in the mass spectrometer. The more energy imparted to a population of ions the more likely it is that fragmentation will occur through collision of analyte molecules with the bath gas present in the source. By adjusting the electric field used to accelerate ions from the ionisation chamber it is possible to control the fragmentation of ions. This is advantageous when fragmentation of ions is to be used as a means of removing tags from a labeled biomolecule. Electrospray ionisation is particularly advantageous as it can be used in-line with liquid chromatography, referred to as Liquid Chromatography Mass Spectrometry (LC-MS).

Matrix Assisted Laser Desorption Ionisation (MALDI)

MALDI requires that the biomolecule solution be embedded in a large molar excess of a photo-excitable 'matrix'. The application of laser light of the appropriate frequency results in the excitation of the matrix which in turn leads to rapid evapouration of the matrix along with its entrapped biomolecule. Proton transfer from the acidic matrix to the biomolecule gives rise to protonated forms of the biomolecule which can be detected by positive ion mass spectrometry, particularly by Time-Of-Flight (TOF) mass spectrometry. Negative ion mass spectrometry is also possible by MALDI TOF. This technique imparts a significant quantity of translational energy to ions, but tends not to induce excessive fragmentation despite this. Accelerating voltages can again be used to control fragmentation with this technique though.

Fast Atom Bombardment

Fast Atom Bombardment (FAB) has come to describe a number of techniques for vapourising and ionising relatively involatile molecules. In these techniques a sample is desorbed from a surface by collision of the sample with a high energy beam of xenon atoms or caesium ions. The sample is coated onto a surface with a simple matrix, typically a non volatile material, e.g. m-nitrobenzyl alcohol (NBA) or glycerol. FAB techniques are also compatible with liquid phase inlet systems—the liquid eluting from a capillary electrophoresis inlet or a high pressure liquid chromatography system pass through a frit, essentially coating the surface of the frit with analyte solution which can be ionised from the frit surface by atom bombardment.

Mass Analysers

Fragmentation of peptides by collision induced dissociation is used in this invention to identify tags on proteins. Various mass analyser geometries may be used to fragment peptides and to determine the mass of the fragments.

MS/MS and MS$^n$ Analysis of Peptides

Tandem mass spectrometers allow ions with a pre-determined mass-to-charge ratio to be selected and fragmented by collision induced dissociation (CID). The fragments can then be detected providing structural information about the selected ion. When peptides are analysed by CID in a tandem mass spectrometer, characteristic cleavage patterns are observed, which allow the sequence of the peptide to be determined. Natural peptides typically fragment randomly at the amide bonds of the peptide backbone to give series of ions that are characteristic of the peptide. CLD fragment series are denoted $a_n$, $b_n$, $c_n$, etc. for cleavage at the $n^{th}$ peptide bond where the charge of the ion is retained on the N-terminal fragment of the ion. Similarly, fragment series are denoted $x_n$, $y_n$, $z_n$, etc. where the charge is retained on the C-terminal fragment of the ion.

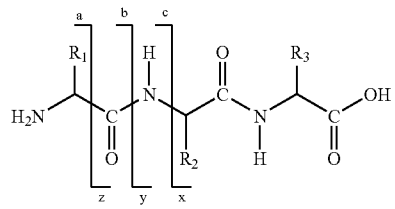

Trypsin and thrombin are favoured cleavage agents for tandem mass spectrometry as they produce peptides with basic groups at both ends of the molecule, i.e. the alpha-amino group at the N-terminus and lysine or arginine side-chains at the C-terminus. This favours the formation of doubly charged ions, in which the charged centres are at opposite termini of the molecule. These doubly charged ions produce both C-terminal and N-terminal ion series after CID. This assists in determining the sequence of the peptide. Generally speaking only one or two of the possible ion series are observed in the CID spectra of a given peptide. In low-energy collisions typical of quadrupole based instruments the b-series of N-terminal fragments or the y-series of C-terminal fragments predominate. If doubly charged ions are analysed then both series are often detected. In general, the y-series ions predominate over the b-series.

In general peptides fragment via a mechanism that involves protonation of the amide backbone follow by intramolecular nucleophilic attack leading to the formation of a 5-membered oxazolone structure and cleavage of the amide linkage that was protonated (Schlosser A. and Lehmann W. D. J. Mass Spectrom. 35: 1382-1390, "Five-membered ring formation in unimolecular reactions of peptides: a key structural element controlling low-energy collision induced dissociation", 2000). FIG. 16a shows one proposed mechanism by which this sort of fragmentation takes place. This mechanism requires a carbonyl group from an amide bond adjacent to a protonated amide on the N-terminal side of the protonated amide to carry out the nucleophilic attack. A charged oxazolonium ion gives rise to b-series ions, while proton transfer from the N-terminal fragment to the C-terminal fragment gives rise to y-series ions as shown in FIG. 16a. This requirement for an appropriately located carbonyl group does not account for cleavage at amide bonds adjacent to the N-terminal amino acid, when the N-terminus is not protected and, in general, b-series ions are not seen for the amide between the N-terminal and second amino acid in a peptide. However, peptides with acetylated N-termini do meet the structural requirements of this mechanism and fragmentation can take place at the amide bond immediately after the first amino acid by this mechanism. Peptides with thioacetylated N-termini, as shown in FIG. 16c, will cleave particularly easily by the oxazolone mechanism as the sulphur atom is more nucleophilic than an oxygen atom in the same position. Fragmentation of the amide backbone of a peptide can also be modulated by methylation of the backbone. Methylation of an amide nitrogen in a peptide can promote fragmentation of the next amide bond C-terminal to the methylated amide and also favours the formation of b-ions. The enhanced fragmentation may be partly due to the electron donating effect of the methyl group increasing the nucleophilicity of the carbonyl group of the methylated amide, while the enhanced formation of b-ions may be a result of the inability of the oxazolonium ion that forms to transfer protons to the C-terminal fragment as shown in FIG. 16b. In the context of this invention thioacetylation of the N-terminus of a tag dipeptide can be used to enhance cleavage of the tag peptide at the next amide bond. Similarly, methylation of the nitrogen atom of an N-terminal acetyl or thioacetyl group will also enhance cleavage of the adjacent amide bond. FIGS. 17a and 17b illustrate pairs of tags that exploit these methods of enhancing cleavage at the marked amide linkage.

The ease of fragmentation of the amide backbone of a polypeptide or peptide is also significantly modulated by the side chain functionalities of the peptide. Thus the sequence of a peptide determines where it will fragment most easily. In general it is difficult to predict which amide bonds will fragment easily in a peptide sequence. This has important consequences for the design of the peptide mass tags of this invention. However, certain observations have been made that allow peptide mass tags that fragment at the desired amide bond to be designed. Proline, for example, is known to promote fragmentation at its N-terminal amide bond (Schwartz B. L., Bursey M. M., Biol. Mass Spectrom. 21:92, 1997) as fragmentation at the C-terminal amide gives rise to an energetically unfavourable strained bicyclic oxazolone structure. Aspartic acid also promotes fragmentation at its N-terminal amide bond. Asp-Pro linkages, however, are particularly labile in low energy CID analysis (Wysocki V. H. et al., J Mass Spectrom. 35(12): 1399-1406, "Mobile and localized protons: a framework for understanding peptide dissociation." 2000) and in this situation aspartic acid seems to promote the cleavage of the amide bond on its C-terminal side. Thus proline, and asp-pro linkages can also be used in the tag peptides of this invention to promote fragmentation at specified locations within a peptide. FIGS. 17c and 17d illustrate pairs of tags that exploit these methods of enhancing cleavage at the marked amide linkage. FIG. 17c illustrates a pair of tripeptide tags with the sequence alanine-proline-alanine. The proline linkage promotes cleavage at its N-terminal amide. This is enhanced by the presence of a thioacetyl protecting group at the N-terminus of the tripeptide and the cleavability is further enhanced by methylation of the N-terminal nitrogen. The tags have the same mass but in the first tag there is an alanine residue with heavy isotopes in the third position of the tripeptide while in the second tag there is an alanine residue with heavy isotopes in the first position of the tripeptide. FIG. 17d illustrates a pair of tripeptide tags with the sequence aspartic acid-proline-alanine. The proline linkage promotes cleavage at its N-terminal amide. This is enhanced by the presence of the aspartic acid residue. The N-terminus of the tripeptide is methylated to promote localised protonation here. The tags have the same mass but in the first tag there is an alanine residue with heavy isotopes in the third position of the tripeptide while in the second tag there is an aspartic acid residue with heavy isotopes in the first position of the tripeptide.

A typical tandem mass spectrometer geometry is a triple quadrupole which comprises two quadrupole mass analysers separated by a collision chamber, also a quadrupole. This collision quadrupole acts as an ion guide between the two mass analyser quadrupoles. A gas can be introduced into the collision quadrupole to allow collision with the ion stream from the first mass analyser. The first mass analyser selects ions on the basis of their mass/charge ration which pass through the collision cell where they fragment. The fragment ions are separated and detected in the third quadrupole. Induced cleavage can be performed in geometries other than tandem analysers. Ion trap mass spectrometers can promote fragmentation through introduction of a gas into the trap itself with which trapped ions will collide. Ion traps generally contain a bath gas, such as helium but addition of neon for example, promotes fragmentation. Similarly photon induced fragmentation could be applied to trapped ions. Another favourable geometry is a Quadrupole/Orthogonal Time of Flight tandem instrument where the high scanning rate of a quadrupole is coupled to the greater sensitivity of a reflectron TOF mass analyser to identify the products of fragmentation.

Conventional 'sector' instruments are another common geometry used in tandem mass spectrometry. A sector mass analyser comprises two separate 'sectors', an electric sector which focuses an ion beam leaving a source into a stream of ions with the same kinetic energy using electric fields. The magnetic sector separates the ions on the basis of their mass to generate a spectrum at a detector. For tandem mass spectrometry a two sector mass analyser of this kind can be used where the electric sector provide the first mass analyser stage, the magnetic sector provides the second mass analyser, with a collision cell placed between the two sectors. Two complete sector mass analysers separated by a collision cell can also be used for analysis of mass tagged peptides.

Ion Traps

Ion Trap mass analysers are related to the quadrupole mass analysers. The ion trap generally has a 3 electrode construction—a cylindrical electrode with 'cap' electrodes at each end forming a cavity. A sinusoidal radio frequency potential is applied to the cylindrical electrode while the cap electrodes are biased with DC or AC potentials. Ions injected into the cavity are constrained to a stable circular trajectory by the oscillating electric field of the cylindrical electrode. However, for a given amplitude of the oscillating potential, certain ions will have an unstable trajectory and will be ejected from the trap. A sample of ions injected into the trap can be sequentially ejected from the trap according to their mass/charge ratio by altering the oscillating radio frequency potential. The ejected ions can then be detected allowing a mass spectrum to be produced.

Ion traps are generally operated with a small quantity of a 'bath gas', such as helium, present in the ion trap cavity. This increases both the resolution and the sensitivity of the device as the ions entering the trap are essentially cooled to the ambient temperature of the bath gas through collision with the bath gas. Collisions both increase ionisation when a sample is introduced into the trap and dampen the amplitude and velocity of ion trajectories keeping them nearer the centre of the trap. This means that when the oscillating potential is changed, ions whose trajectories become unstable gain energy more rapidly, relative to the damped circulating ions and exit the trap in a tighter bunch giving a narrower larger peaks.

Ion traps can mimic tandem mass spectrometer geometries, in fact they can mimic multiple mass spectrometer geometries allowing complex analyses of trapped ions. A single mass species from a sample can be retained in a trap, i.e. all other species can be ejected and then the retained species can be carefully excited by super-imposing a second oscillating frequency on the first. The excited ions will then collide with the bath gas and will fragment if sufficiently excited. The fragments can then be analysed further. It is possible to retain a fragment ion for further analysis by ejecting other ions and then exciting the fragment ion to fragment. This process can be repeated for as long as sufficient sample exists to permit further analysis. It should be noted that these instruments generally retain a high proportion of fragment ions after induced fragmentation. These instruments and FTICR mass spectrometers (discussed below) represent a form of temporally resolved tandem mass spectrometry rather than spatially resolved tandem mass spectrometry which is found in linear mass spectrometers.

Fourier Transform Ion Cyclotron Resonance Mass Spectrometry (FTICR MS)

FTICR mass spectrometry has similar features to ion traps in that a sample of ions is retained within a cavity but in FTICR MS the ions are trapped in a high vacuum chamber by crossed electric and magnetic fields. The electric field is generated by a pair of plate electrodes that form two sides of a box. The box is contained in the field of a superconducting magnet which in conjunction with the two plates, the trapping plates, constrain injected ions to a circular trajectory between the trapping plates, perpendicular to the applied magnetic field. The ions are excited to larger orbits by applying a radio-frequency pulse to two 'transmitter plates' which form two further opposing sides of the box. The cycloidal motion of the ions generate corresponding electric fields in the remaining two opposing sides of the box which comprise the 'receiver plates'. The excitation pulses excite ions to larger orbits which decay as the coherent motions of the ions is lost through collisions. The corresponding signals detected by the receiver plates are converted to a mass spectrum by Fourier Transform (FT) analysis.

For induced fragmentation experiments these instruments can perform in a similar manner to an ion trap—all ions except a single species of interest can be ejected from the trap. A collision gas can be introduced into the trap and fragmentation can be induced. The fragment ions can be subsequently analysed. Generally fragmentation products and bath gas combine to give poor resolution if analysed by FT analysis of signals detected by the 'receiver plates', however the fragment ions can be ejected from the cavity and analysed in a tandem configuration with a quadrupole, for example.

Separation of Labeled Peptides by Chromatography or Electrophoresis

In the optional second step of the second aspect of this invention, labeled biomolecules are subjected to a chromatographic separation prior to analysis by mass spectrometry. This is preferably High Performance Liquid Chromatography (HPLC) which can be coupled directly to a mass spectrometer for in-line analysis of the peptides as they elute from the chromatographic column. A variety of separation techniques may be performed by HPLC but reverse phase chromatography is a popular method for the separation of peptides prior to mass spectrometry. Capillary zone electrophoresis is another separation method that may be coupled directly to a mass spectrometer for automatic analysis of eluting samples. These and other fractionation techniques may be applied to reduce the complexity of a mixture of biomolecules prior to analysis by mass spectrometry.

Applications of the Invention

Labeling Peptides and Polypeptides and Analysis by LC-MS-MS

In preferred embodiments of the second aspect of this invention, the tags are used for the analysis of mixtures of peptides by liquid chromatography tandem mass spectrometry (LC-MS-MS). The use of the mass labels of this invention according to the second aspects will now be discussed in the context of the analysis of peptides. Peptide mass tags such as those in FIGS. 1 and 2 may be used to label peptides. If the reactive functionality on these compounds is an N-hydroxysuccinimide ester then the tags will be reactive with free amino groups such as alpha-amino groups and epsilon amino groups in lysine.

After attachment of the tags, the labeled peptides will have a mass that is shifted by the mass of the tag. The mass of the peptide may be sufficient to identify the source protein. In this case only the tag needs to be detected which can be achieved by selected reaction monitoring with a triple quadrupole, discussed in more detail below. Briefly, the first quadrupole of the triple quadrupole is set to let through ions whose mass-to-charge ratio corresponds to that of the peptide of interest, adjusted for the mass of the marker. The selected ions are then subjected to collision induced dissociation (CID) in the second quadrupole. Under the sort of conditions used in the analysis of peptides the ions will fragment mostly at the amide bonds in the molecule. The markers in FIGS. 1 and 2 have an amide bond, which releases the N-terminal portion of the tag on cleavage. Although the tags all have the same mass, the terminal portion is different because of differences in the substituents on either side of the amide bond. Thus the markers can be distinguished from each other. The presence of the marker fragment associated with an ion of a specific mass should confirm that the ion was a peptide and the relative peak heights of the tags from different samples will give information about the relative quantities of the peptides in their samples. If the mass is not sufficient to identify a peptide, either because a number of terminal peptides in the sample have the same terminal mass or because the peptide is not known, then sequence information may be determined by analysis of the complete CID spectrum. The peptide fragmentation peaks can be used to identify the peptides while the mass tag peaks give information about the relative quantities of the peptides.

The analysis of proteins by tandem mass spectrometry, particularly mixtures of peptides, is complicated by the 'noisiness' of the spectra obtained. Peptides isolated from biological samples are often contaminated with buffering reagents, denaturants and detergents, all of which introduce peaks into the mass spectrum. As a result, there are often more contamination peaks in the spectrum than peptide peaks and identifying peaks that correspond to peptides is major problem, especially with small samples of proteins that are difficult to isolate. As a result various methods are used to determine which peaks correspond to peptides before detailed CID analysis is performed. Triple quadrupole based instruments permit 'precursor ion scanning' (see Wilm M. et al., Anal Chem 68(3):527-33, "Parent ion scans of unseparated peptide mixtures." (1996)). The triple quadrupole is operated in 'single reaction monitoring' mode, in which the first quadrupole scans over the full mass range and each gated ion is subjected to CID in the second quadrupole. The third quadrupole is set to detect only one specific fragment ion, which is usually a characteristic fragment ion from a peptide such as immonium ions. The presence of phosphate groups can also be detected using this sort of technique. An alternative method used with quadrupole/time-of-flight mass spectrometers scans for doubly charged ions by identifying ions which when subjected to CID produce daughter ions with higher mass-to-charge ratios than the parent ion. A further method of identifying doubly charged ions is to look for sets of peaks in the spectrum which are only 0.5 daltons apart with appropriate intensity ratios which would indicate that the ions are the same differing only by the proportion of $^{13}C$ present in the molecule.

By labeling peptides with the mass labels of this invention, a novel form of precursor ion scanning may be envisaged in which peptide peaks are identified by the presence of fragments corresponding to the mass labels of this invention after subjecting the labeled peptides to CID. In particular, the peptides isolated from each sample by the methods of this invention may be labeled with more than one tag. An equimolar mixture of a 'precursor ion scanning' tag which is used in all samples and a sample specific tag may be used to label the peptides in each sample. In this way changes in the level of peptides in different samples will not have an adverse effect on the identification of peptide peaks in a precursor ion scan.

Having identified and selected a peptide ion, it is subjected to CID. The CED spectra are often quite complex and determining which peaks in the CED spectrum correspond to meaningful peptide fragment series is a further problem in determining the sequence of a peptide by mass spectrometry. Shevchenko et al., Rapid Commun. Mass Spec. 11: 1015-1024 (1997) describe a further method, which involves treating proteins for analysis with trypsin in 1:1 $^{16}O/^{18}O$ water. The hydrolysis reaction results in two populations of peptides, the first whose terminal carboxyl contains $^{16}O$ and the second whose terminal carboxyl contains $^{18}O$. Thus for each peptide in the sample there should be a double peak of equal intensity for each peptide where the double peak is 2 Daltons apart. This is complicated slightly by intrinsic peptide isotope peaks but allows for automated scanning of the CID spectrum for doublets. The differences in mass between doublets can be determined to identify the amino acid by the two fragments differ. This method may be applicable with the methods of this invention if N-terminal peptides are isolated.

Protein Expression Profiling

To understand the changes in a cancerous tissue, for example, requires an understanding of all of the molecular changes in that tissue, ideally relating these changes to normal tissue. To determine all of the molecular changes requires the ability to measure changes in gene expression, protein expression and ultimately metabolite changes. It is possible to compare the expression, between different tissue samples, of large numbers of genes simultaneously at the level of messenger RNA (mRNA) using microarray technology (see for example Iyer V. R. et al., Science 283(5398):83-87, "The transcriptional program in the response of human fibroblasts to serum." 1999), however mRNA levels do not correlate directly to the levels of protein in a tissue. To determine a protein expression profile for a tissue, 2-dimensional gel electrophoresis is widely used. Unfortunately, this technique is extremely laborious and it is difficult to compare two or more samples simultaneously on a 2-D gel due to the difficulty of achieving reproducibility. As discussed above peptides may be analysed effectively using the methods of this invention.

The tags of this invention allow the same peptide from different samples to be identified using LC-MS-MS. In addition, the relative quantities of the same peptide in different samples may be determined. The ability to rapidly and sensitively determine the identity and relative quantities of peptides in a number of samples allows for expression profiling. Therefore it is an object of this invention to provide improved methods for comparative analysis of complex protein samples based on the selective isolation and labeling of peptides. Two published approaches for the global analysis of protein expression are discussed and various methods for the analysis of particular protein states, such as phosphorylation and carbohydrate modification are also described below.

Terminal Peptide Isolation for Global Protein Expression Profiling

Isolation of N- or C-terminal peptides has been described as a method to determine a global expression profile of a protein sample. Isolation of terminal peptides ensures that at least one and only one peptide per protein is isolated thus ensuring that the complexity of the sample that is analysed does not have more components than the original sample. Reducing large polypeptides to shorter peptides makes the sample more amenable to analysis by mass spectrometry. Methods for isolating peptides from the termini of polypeptides are discussed in PCT/GB98/00201, PCT/GB99/03258.

Isolation of Peptides Containing Cysteine

As discussed earlier, Gygi et al. (Nature Biotechnology 17: 994 -999 1999) disclose the use of 'isotope encoded affinity tags' for the capture of peptides from proteins, to allow protein expression analysis. The authors report that a large proportion of proteins (>90%) in yeast have at least one cysteine residue (on average there are ~5 cysteine residues per protein). Reduction of disulphide bonds in a protein sample and capping of free thiols with iodoacetamidylbiotin results in the labeling of all cysteine residues. The labeled proteins are then digested, with trypsin for example, and the cysteine-labeled peptides may be isolated using avidinated beads. These captured peptides can then be analysed by liquid chromatography tandem mass spectrometry (LC-MS/MS) to determine an expression profile for the protein sample. Two protein samples can be compared by labeling the cysteine residues with a different isotopically modified biotin tag. This approach is slightly more redundant than an approach based on isolating terminal peptides as, on average, more than one peptide per protein is isolated so there are more peptide species in the sample than protein species. This increase in complexity is made worse by the nature of the tags used by Gygi et al.

As discussed above the affinity tags described by Gygi et al. have some disadvantages. Labeling each sample with a different isotope variant of the affinity tag results in an additional peak in the mass spectrum for each peptide in each sample. This means that if two samples are analysed together there will be twice as many peaks in the spectrum. Similarly, if three samples are analysed together, the spectrum will be three times more complex than for one sample alone. A further limitation, which is reported by the authors of the above paper, is the mobility change caused by the tags. The authors report that peptides labeled with a deuterated biotin tag elute slightly after the same peptide labeled with an undeuterated tag. This means that comparative analysis of multiple samples will be very difficult using the methods of Gygi et al. because of the complexity of the mass spectra and the complexity of the chromatographic steps if more than 2 samples were analysed.

Figure 8:
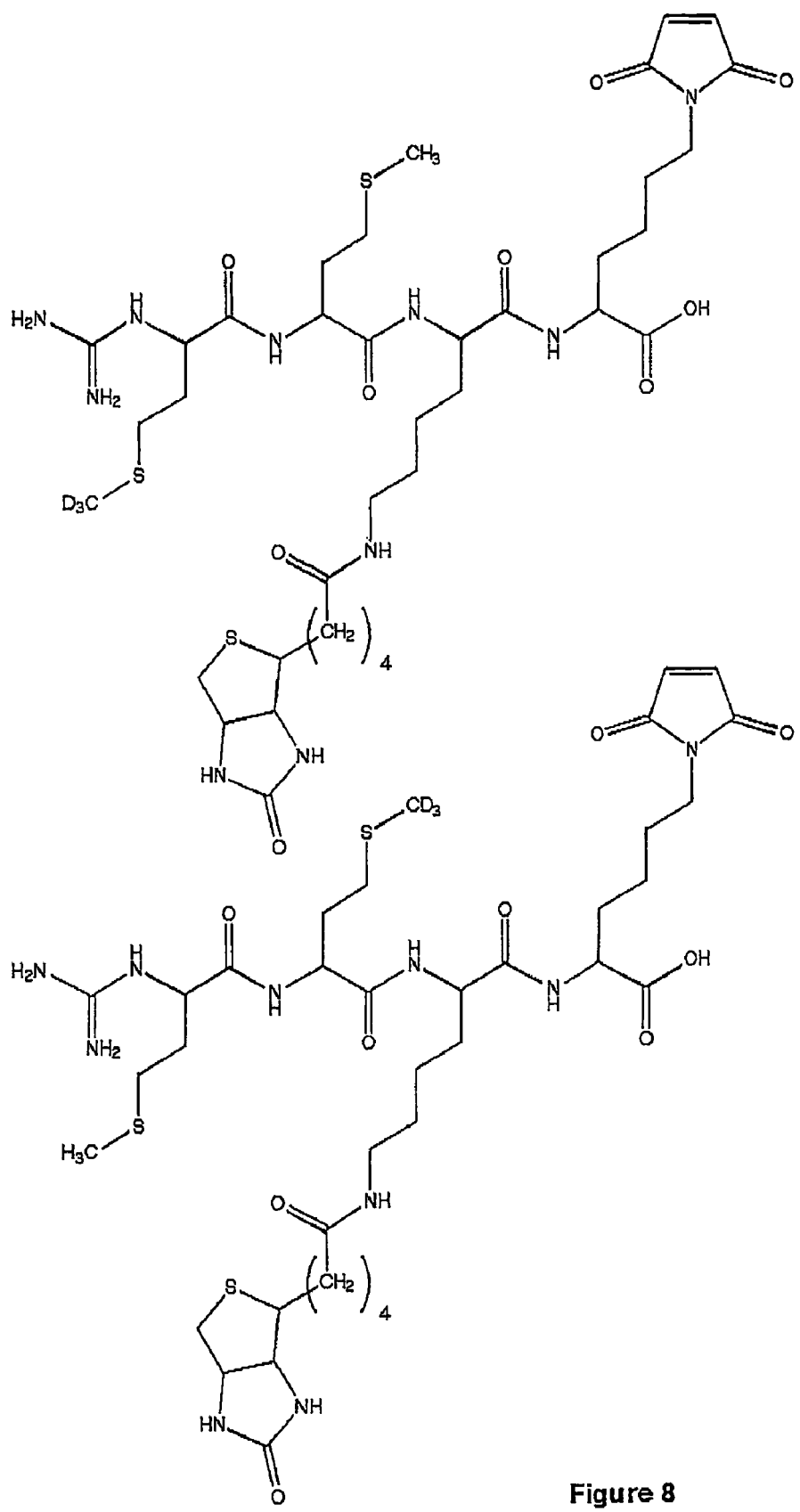
FIG. 8 shows a set of 2 affinity ligand mass tags derived from methionine with a maleimide functionality for labeling free thiols.

An improved method for analysing protein samples by labeling cysteine residues is envisaged using tags of the form shown in FIG. 8. This Figure illustrates a pair of improved affinity tags derived from methionine. Different isotopically substituted forms of methionine would be used to prepare the two different tags. The total mass of each of the two tags is the same but the N-terminal methionine in each tag differs from the other tag by three Daltons. The alpha amino group of the dipeptide tag has been guanidinated to differentiate the fragmentation product of this amino acid from the fragmentation product of the second methionine residue and the natural methionine residues in protein and to promote protonation at this position in the tag during ionisation in a mass spectrometer. In addition these tags comprise a thiol reactive maleimide functionality.

In an embodiment of the second aspect of this invention, a protocol for the analysis of a protein sample containing polypeptides with cysteine residues comprises the steps of:
1. Reducing and reacting all cysteine residues in at least one protein sample with a maleimide affinity ligand mass tag;
2. Cleaving the polypeptides with a sequence specific endoprotease;
3. Capturing tagged peptides onto an avidin derivitised solid support; and
4 Analysing the captured tagged peptides by LC-MS-MS.

The protein samples may be digested with the sequence specific endoprotease before or after reaction of the sample with the affinity ligand mass tag.

Isolation of Carbohydrate Modified Proteins

Carbohydrates are often present as a post-translational modification of proteins. Various affinity chromatography techniques for the isolation of these sorts of proteins are known (For a review see Gerard C., Methods Enzymol. 182: 529-539, "Purification of glycoproteins." 1990). A variety of natural protein receptors for carbohydrates are known. The members of this class of receptors, known as lectins, are highly selective for particular carbohydrate functionalities. Affinity columns derivatised with specific lectins can be used to isolate proteins with particular carbohydrate modifications, whilst affinity columns comprising a variety of different lectins could be used to isolate populations of proteins with a variety of different carbohydrate modifications. In one embodiment of the second aspect of this invention, a protocol for the analysis of a sample of proteins, which contains carbohydrate modified proteins, comprises the steps of:
1. Treating the sample with a sequence specific cleavage reagent such as Trypsin or Lys-C;
2. Passing the protein sample through affinity columns contain lectins or boronic acid derivatives to isolate only carbohydrate modified peptides;
3. Labeling the captured sugar modified peptides at the free alpha amino group generated by the sequence specific cleavage, using the peptide mass tags of this invention; and
4. Analysing the tagged peptides by LC-MS-MS.

An N-hydroxysuccinimide activated tag could be used to label the free alpha-amino groups. If Lys-C is used then each carbohydrate modified peptide will have a free epsilon-amino group as well as a free alpha amino group, both of which can be tagged.

Many carbohydrates have vicinal-diol groups present, i.e. hydroxyl groups present on adjacent carbon atoms. Diol containing carbohydrates that contain vicinal diols in a 1,2-cis-diol configuration will react with boronic acid derivatives to form cyclic esters. This reaction is favoured at basic pH but is easily reversed at acid pH. Resin immobilised derivatives of phenyl boronic acid have been used as ligands for affinity capture of proteins with cis-diol containing carbohydrates. In one embodiment of the fourth aspect of this invention a set of affinity ligand peptide mass tags comprising biotin linked to a phenylboronic acid entity could be synthesised, as shown in FIG. 6b. These boronic acid tags could used to label two separate samples comprising peptides or proteins with carbohydrate modifications that contain vicinal cis-diols. In another embodiment of the second aspect of this invention, a protocol for the analysis of a protein sample containing carbohydrate modified polypeptides comprises the steps of:
1. Reacting at least one protein sample at basic pH with a boronic acid affinity ligand mass tag,
2. Cleaving the polypeptides with a sequence specific endoprotease,
3. Capturing tagged peptides onto an avidin derivitised solid support; and
4. Analysing the captured tagged peptides by LC-MS-MS.

The sample may be digested with the sequence specific endoprotease before or after reaction of the sample with the affinity ligand mass tag.

Vicinal-diols, in sialic acids for example, can also be converted into carbonyl groups by oxidative cleavage with periodate. Enzymatic oxidation of sugars containing terminal galactose or galactosamine with galactose oxidase can also convert hydroxyl groups in these sugars to carbonyl groups. Complex carbohydrates can also be treated with carbohydrate cleavage enzymes, such as neuramidase, which selectively remove specific sugar modifications leaving behind sugars, which can be oxidised. These carbonyl groups can be tagged allowing proteins bearing such modifications to be detected or isolated. Hydrazide reagents, such as Biocytin hydrazide (Pierce & Warriner Ltd, Chester, UK) will react with carbonyl groups in carbonyl-containing carbohydrate species (E. A. Bayer et al., Anal. Biochem. 170: 271-281, "Biocytin hydrazid—a selective label for sialic acids, galactose, and other sugars in glycoconjugates using avidin biotin technology", 1988). Alternatively a carbonyl group can be tagged with an amine modified biotin, such as Biocytin and EZ-Link™ PEO-Biotin (Pierce & Warriner Ltd, Chester, UK), using reductive alkylation (Means G. E., Methods Enzymol 47: 469-478, "Reductive alkylation of amino groups." 1977; Rayment I., Methods Enzymol 276: 171-179, "Reductive alkylation of lysine residues to alter crystallization properties of proteins." 1997). Proteins bearing vicinal-diol containing carbohydrate modifications in a complex mixture can thus be biotinylated. Biotinylated, hence carbohydrate modified, proteins may then be isolated using an avidinated solid support.

A set of peptide mass tags according to this invention can be synthesised for the analysis of carbohydrate modified peptides that have been oxidised with periodate, as shown in FIG. 6a. FIG. 6a shows a set of two tags derived from methionine. Different isotopically substituted forms of methionine would be used to prepare the two different tags. The total mass of each of the two tags is the same but the N-terminal methionine in each tag differs from the other tag by three Daltons. The alpha amino group of the dipeptide tag has been guanidinated to differentiate the fragmentation product of this amino acid from the fragmentation product of the second methionine residue and to promote protonation at this position in the tag during ionisation in a mass spectrometer. A further embodiment of the second aspect of this invention comprises the steps of:
1. Treating a sample of polypeptides with periodate, so that carbohydrates with vicinal cis-diols on glycopeptides will gain a carbonyl functionality;
2. Labeling this carbonyl functionality with a hydrazide activated peptide mass tag linked to biotin, as shown in FIG. 6a;
3. Digesting the protein sample with a sequence specific endoprotease;

4. Capturing tagged peptides onto an avidin derivitised solid support; and
5. Analysing the biotinylated peptides by LC-MS-MS.

The protein sample may be digested with the sequence specific endoprotease before or after reaction of the sample with the affinity ligand mass tag.

Isolation of Phosphopeptides

Phosphorylation is a ubiquitous reversible post-translational modification that appears in the majority of signaling pathways of almost all organisms as phosphorylation is widely used as a transient signal to mediate changes in the state of individual proteins. It is an important area of research and tools which allow the analysis of the dynamics of phosphorylation are essential to a full understanding of how cells responds to stimuli, which includes the responses of cells to drugs.

Techniques for the analysis of phosphoserine and phosphothreonine containing peptides are well known. One class of such methods is based on a well known reaction for beta-elimination of phosphates. This reaction results in phosphoserine and phosphothreonine forming dehydroalanine and methyldehydroalanine, both of which are Michael acceptors and will react with thiols. This has been used to introduce hydrophobic groups for affinity chromatography (See for example Holmes C. F., FEBS Lett 215(1): 21-24, "A new method for the selective isolation of phosphoserine-containing peptides." 1987). Dithiol linkers have also been used to introduce fluorescein and biotin into phosphoserine and phosphothreonine containing peptides (Fadden P, Haystead T A, Anal Biochem 225(1): 81-8, "Quantitative and selective fluorophore labeling of phosphoserine on peptides and proteins: characterization at the attomole level by capillary electrophoresis and laser-induced fluorescence." 1995; Yoshida O. et al., Nature Biotech 19: 379-382, "Enrichment analysis of phosphorylated proteins as a tool for probing the phosphoproteome", 2001). The method of Yoshida et al. for affinity enrichment of proteins phosphorylated at serine and threonine could be improved by using the maleimide tag shown in FIG. 8 to allow the comparison of multiple samples. This would be particularly useful for the analysis of the dynamics of phosphorylation cascades.

Figure 7:
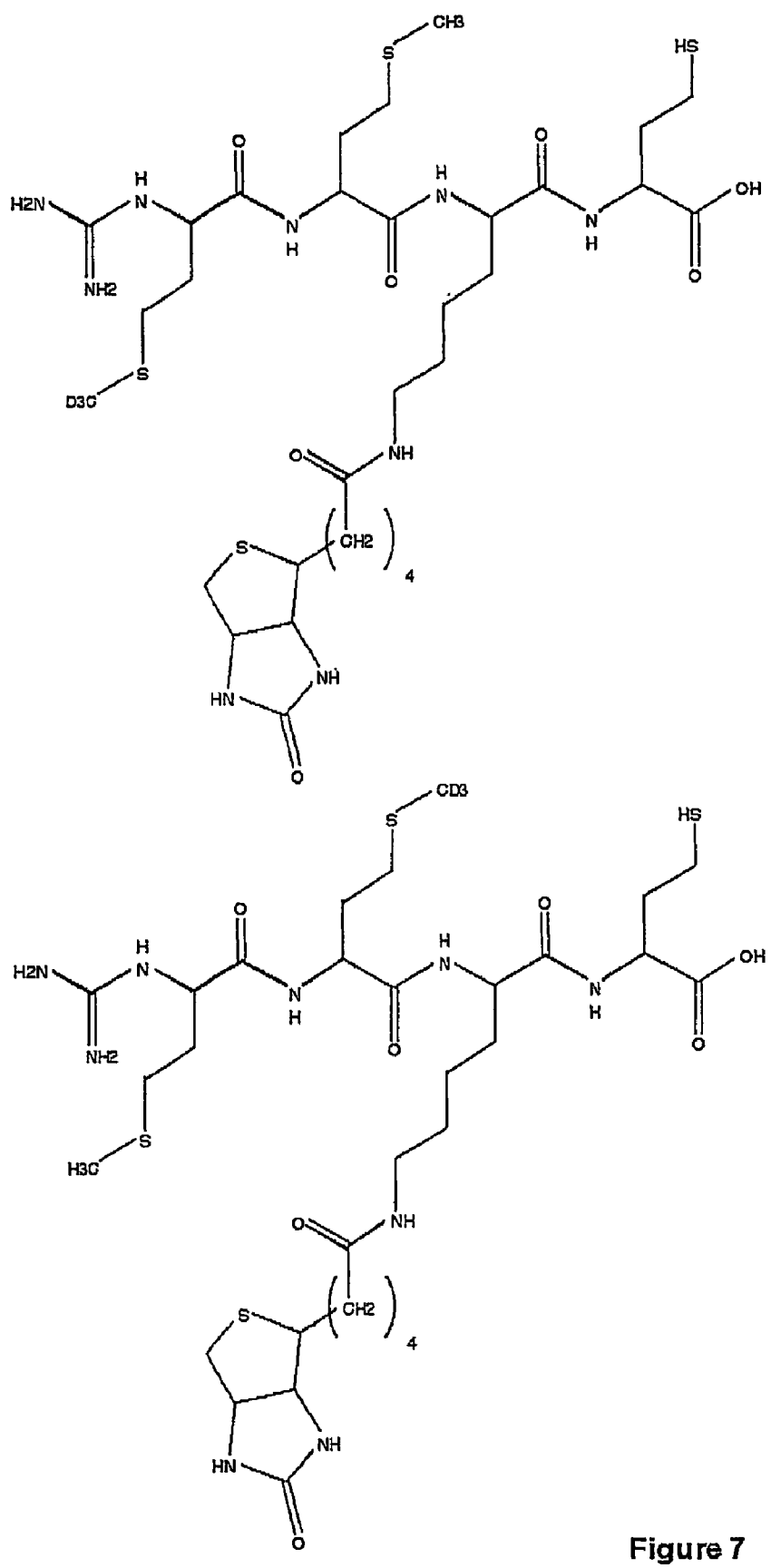
FIG. 7 shows a set of 2 affinity ligand mass tags derived from methionine with a thiol functionality for labeling dehydroalanine and methyldehydroalanine residues.

A tag peptide of the form shown in FIG. 7 would allow direct labeling of beta-eliminated phosphothreonine and phosphoserine residues without a dithiol linker. The tag tetrapeptide of FIG. 7 is derived from methionine. Different isotopically substituted forms of methionine would be used to prepare the two different tags. The total mass of each of the two tags is the same but the N-terminal methionine in each tag differs from the other tag by three Daltons. The alpha amino group of the dipeptide tag has been guanidinated to differentiate the fragmentation product of this amino acid from the fragmentation product of the second methionine residue and natural methionine residues in proteins and to promote protonation at this position in the tag during ionisation in a mass spectrometer. The tag peptide is guanidinated at the N-Terminus to provide enhanced sensitivity and to distinguish the N-terminal residue from the C-terminal residue. The cysteine residue provides a free thiol, which can nucleophilically attack dehydroalanine and methyldehydroalanine. An improved protocol for the beta-elimination based labeling procedure is known. This improved procedure involves barium catalysis. (Byford M. F., Biochem J. 280: 261-261, "Rapid and selective modification of phosphoserine residues catalysed by Ba2+ ions for their detection during peptide microsequencing." 1991) This catalysis makes the reaction 20-fold faster reducing side-reactions to undetectable levels.

The tag peptide shown in FIG. 7 could be easily coupled to dehydroalanine or methyldehydroalanine generated from beta-elimination of phosphates using barium catalysis. Thus in a further embodiment of the second aspect of this invention, peptides phosphorylated at serine and threonine may be analysed in a method comprising the steps of:
1. Treating a sample of polypeptides with barium hydroxide to beta-eliminate phosphate groups from phosphoserine and phosphothreonine;
2. Labeling the resultant dehydroalanine or methyldehydroalanine functionalities with the thiol activated peptide mass tag linked to biotin, as shown in FIG. 7;
3. Digesting the protein sample with a sequence specific endoprotease,
4. Capturing tagged peptides onto an avidin derivitised solid support; and
5. Analysing the biotinylated peptides by LC-MS-MS.

The protein sample may be digested with the sequence specific endoprotease before or after reaction of the sample with the affinity ligand mass tag.

A number of research groups have reported on the production of antibodies, which bind to phosphotyrosine residues in a wide variety of proteins. (see for example A. R. Frackelton et al., Methods Enzymol 201: 79-92, "Generation of monoclonal antibodies against phosphotyrosine and their use for affinity purification of phosphotyrosine-containing proteins.", 1991 and other articles in this issue of Methods Enzymol.). This means that a significant proportion of proteins that have been post-translationally modified by tyrosine phosphorylation may be isolated by affinity chromatography using these antibodies as the affinity column ligand.

These phosphotyrosine binding antibodies can be used in the context of this invention to isolate peptides from proteins containing phosphotyrosine residues. The tyrosine-phosphorylated proteins in a complex mixture may be isolated using anti-phosphotyrosine antibody affinity columns. In a further embodiment of the second aspect of this invention, a protocol for the analysis of a sample of proteins, which contains proteins phosphorylated at tyrosine, comprises the steps of:
1. Treating the sample with a sequence specific cleavage reagent such as Trypsin or Lys-C;
2. Passing the protein sample through affinity columns contain anti-phosphotyrosine antibodies to isolate only phosphotyrosine modified peptides;
3. Labeling the captured phosphopeptides at the free alpha amino group generated by the sequence specific cleavage, using the peptide mass tags of this invention; and
4. Analysing the tagged peptides by LC-MS-MS.

An N-hydroxysuccinimide activated tag could be used to label the free alpha-amino groups.

Immobilised Metal Affinity Chromatography (IMAC) represents a further technique for the isolation of phosphoproteins and phosphopeptides. Phosphates adhere to resins comprising trivalent metal ions particularly to Gallium(III) ions (Posewitch, M. C. and Tempst, P., Anal. Chem., 71: 2883-2892, "Immobilized Gallium (III) Affinity Chromatography of Phosphopeptides", 1999). This technique is advantageous as it can isolate both serine/threonine phosphorylated and tyrosine phosphorylated peptides and proteins simultaneously.

IMAC can therefore also be used in the context of this invention for the analysis of samples of phosphorylated proteins. In a further embodiment of the second aspect of this invention, a protocol for the analysis of a sample of proteins, which contains phosphorylated proteins, comprises the steps of:

1. Treating the sample with a sequence specific cleavage reagent such as Trypsin or Lys-C;
2. Passing the protein sample through an affinity column comprising immobilised metal ions to isolate only phosphorylated peptides;
3. Labeling the captured phosphopeptides at the free alpha amino group generated by the sequence specific cleavage, using the peptide mass tags of this invention; and
4. Analysing the tagged peptides by LC-MS-MS.

An N-hydroxysuccinimide activated tag could be used to label the free alpha-amino groups.

In an alternative embodiment of the second aspect of this invention, a sample of phosphorylated proteins may be analysed by isolating phosphorylated proteins followed by analysis of the N or C terminal peptides of the phosphoproteins. Techniques for the isolation of terminal peptides are disclosed in a number of patent applications, e.g. WO98/32876, WO 00/20870 and EP 01304975.4. A protocol for the analysis of a sample of proteins, which contains phosphorylated proteins, would comprise the steps of:
1. Passing the protein sample through an affinity column comprising immobilised metal ions to isolate only phosphorylated proteins;
2. Isolating C and/or N terminal peptides from the captured phosphorylated proteins;
3. Labeling the captured terminal peptides, using the peptide mass tags of this invention; and
4. Analysing the tagged peptides by LC-MS-MS.

EXAMPLES

Example 1

Syntheses of X-Metd$^3$-Met-Gly-OH (A) and of X-Met-Metd$^3$-Gly-OH (B)

Figure 10:
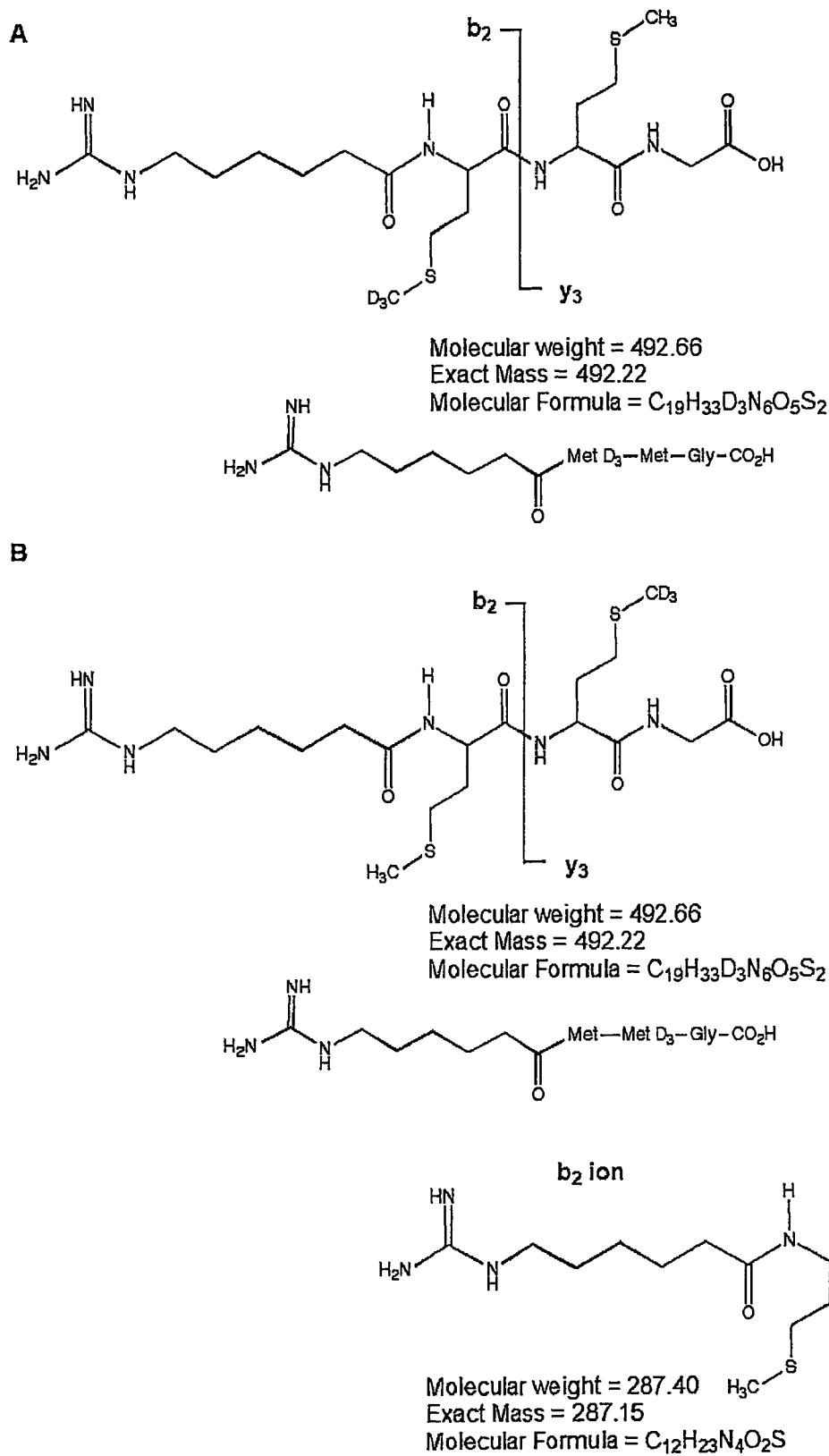
FIG. 10 shows a pair of example peptides derived from different isotopic forms of methionine synthesised to demonstrate the features of this invention.

A pair of peptides were synthesised using conventional automated synthesis techniques to illustrate the features of this invention (both starting from commercially available Fmoc-Gly-Trt-PS resin from Rapp Polymere, Germany). The two peptides A and B are shown in FIG. 10 and will be referred to as the two Met-Met-Gly (D3) peptides.

Deuterated methionine (Metd$^3$) is available from ISOTEC Inc, Mamisburg, Ohio, USA. The Fmoc reagent for use in a peptide synthesiser must, however, be synthesised manually from the unprotected deuterated methionine.

Synthesis of N-(9-Fluorenylmethoxycarbonyl)-L-methionine-methyl-d3 (Fmoc-Metd$^3$)

Figure 9A:
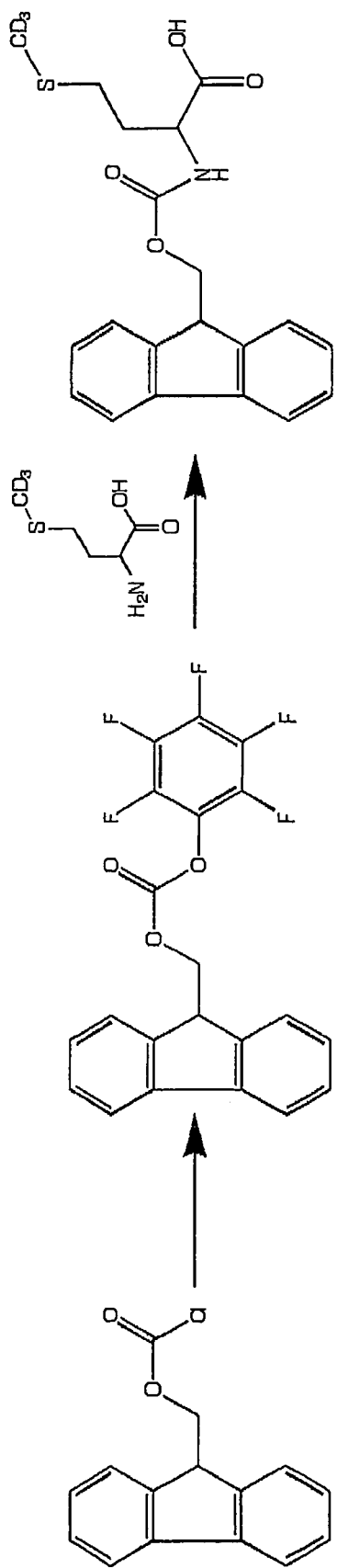
FIG. 9a shows a synthetic pathway for the preparation of an FMOC protected, deuterated methionine residue

The synthesis of Fmoc-Metd$^3$ (shown in FIG. 9a) was carried out in two steps.

1. Synthesis of 9-Fluorenylmethyl-pentafluorphenyl carbonate 8.4 mL (60 mmol) triethylamine were added at 0° C. to a mixture of 11 g (60 mmol) Pentafluorophenol and 15.5 g (60 mmol) chloroformic acid (9-fluorenylmethyl) ester in 100 mL dry ether. After 2 hours reaction, 20 mL cold water was poured to the solution. The organic layer was washed twice with water, dried. After evapouration of the solvent, the obtained product was crystallized from heptane. Yield: 16.4 g (67%)

2. Synthesis of N-(9-Fluorenylmethoxycarbonyl)-L-methionine-methyl-d3

2.2 g (14.5 mmol) L-methionine-methyl-d3 (Metd$^3$) was suspended in 50 mL acetone. 2.5 g (29 mmol) sodium hydrogencarbonate and 60 mL water and then 5.7 g (14 mmol) 9-Fluorenyhnethyl-pentafluorphenyl carbonate were added to the stirred suspension. After 48 hours reaction, the pH of the clear solution was altered to pH 3 and the organic layer was extracted by ethylacetate. After drying the extracted organic layer, the ethylacetate was evapourated and the product was precipitated by addition of heptane. That procedure (dilution with ethylacetate and precipitation by hexane) was repeated twice before obtaining the pure product, Fmoc-Metd$^3$. (Yield: 5.0 g (92%); Fp: 126-128° C.; $[a]_D^{20}$=−30°, c=1, DMF)

The reaction sequences of the peptide synthesiser for the preparation of the two peptides shown in FIG. 10 are listed below.

Peptide Sequence (A)
Swelling of 50 mg of Fmoc-Gly-Trt-PS resin for 5 min in 2 ml of dimethylformamide (DMF);
Removal of the Fmoc group with piperidine in DMF following standard protocols;
Dissolving of 49 mg (0.32 mmol) of 1-hydroxybenzotriazole (HOBt) in 800 µl DMF;
Addition of 120 mg (0.32 mmol) Fmoc-Met to the HOBt solution; this solution was added to the resin and incubated for 3 min;
50 µl (0.32 mmol) of diisopropylcarbodiimide (DIC) was then added; coupling time (0.4M activated amino acid)
Removal of the Fmoc group with piperidine in DMF following standard protocols.
Dissolving of 49 mg (0.32 mmol) HOBt in 800 µl DMF;
Adding to 120 mg (0.32 mmol) Fmoc-Metd$^3$; this solution was added to the resin and incubated for 3 min;
50 µl (0.32 mmol) DIC was then added; coupling time (0.4M activated amino acid)
Removal of the Fmoc group with piperidine in DMF following standard protocols;
150 mg (0.32 mmol) "Boc$_2$X-OSu" were dissolved in 800 µl DMF and this solution was added to the resin;
53 µl of Diisopropylethylamine (DIPEA) were then added to the resin, and the coupling was left to proceed for 3 hours (0.4 M activated species);
After washing the resin the desired substance was cleaved from the resin with 1 ml TFA containing 2.5% H$_2$O, Et$_3$SiH and thioanisole each within 1 h;
Adding of 30 ml water to TFA solution after filtration, removing of all solvent by lyophilisation.
A white powder of peptide sequence (A) resulted.

Peptide Sequence (B)
Swelling of 50 mg resin 5 min in 2 ml DMF;
Removal of the Fmoc group with piperidine in DMF following standard protocols;
Dissolving of 49 mg (0.32 mmol) HOBt in 800 µl DMF;
Adding to 120 mg (0.32 mmol) Fmoc-Metd$^3$; this solution was added to the resin and incubated for 3 min;
50 µl (0.32 mmol) DIC was added; coupling time (0.4 M activated amino acid)
Removal of the Fmoc group with piperidine in DMF following standard protocols;
Dissolving of 49 mg (0.32 mmol) HOBt in 800 µl DMF;
Adding to 120 mg (0.32 mmol) Fmoc-Met; this solution was added to the resin and incubated for 3 min;
50 µl (0.32 mmol) DIC was added; coupling time (0.4 M activated amino acid)
Removal of the Fmoc group with piperidine in DMF following standard protocols;
150 mg (0.32 mmol) "Boc$_2$X-OSu" were dissolved in 800 µl DMF and this solution was added to the resin;

53 µl DIPEA were added, 3 h coupling time (0.4 M activated species)

After washing the resin the desired substance was cleaved from the resin with 1 ml TFA containing 2.5% H₂O, Et₃SiH and thioanisole each within 1 h;

Adding of 30 ml water to TFA solution after filtration, and removal of all solvent by lyophilisation.

A light yellow powder of peptide sequence (B) resulted.

HPLC

After cleavage, ca. 80% pure product was obtained for each peptide. The products were then purified by HPLC.

MS

Figure 11:
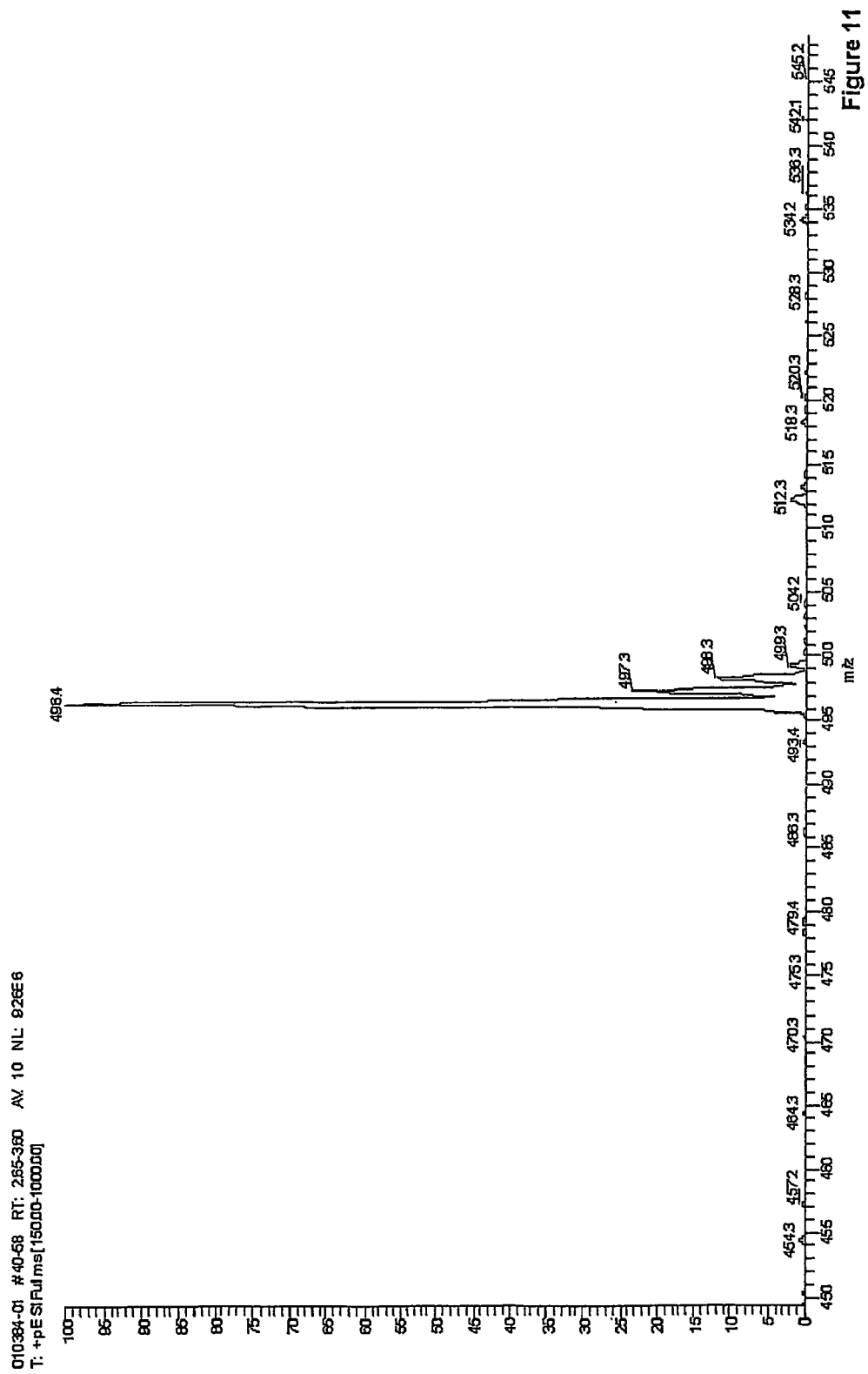
FIG. 11 shows an electrospray mass spectrum of a mixture of the two peptides shown in FIG. 10.

The identity of the peptides A and B was confirmed by mass spectrometry. A mass-to-charge ratio of 496 was observed as the main peak in both MALDI and ESI mass spectra for both products, which fits the calculated mass of both peptides. A mass spectrum from the analysis of a mixture of peptides A and B by ESI mass spectrometry is shown in FIG. 11. It can be seen that the two peptides have mass spectra that overlap almost exactly, which is as expected.

MS/MS

Figure 12A:
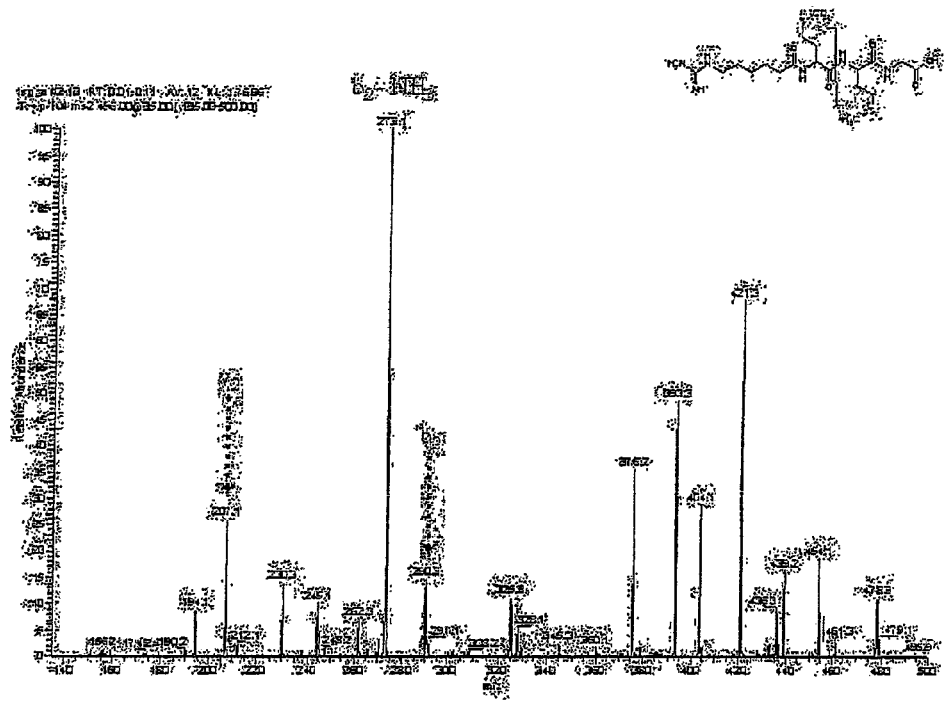
FIGS. 12a and 12b show an electrospray spectrum of the fragmentation of each of the two peptides shown in FIG. 10.
Figure 12B:
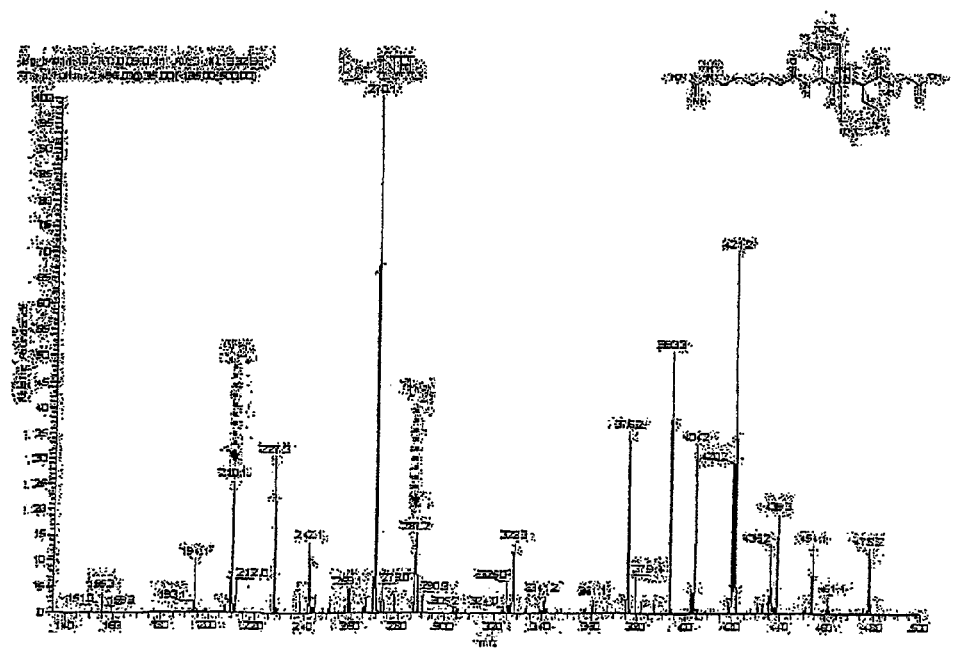
Figure 13:
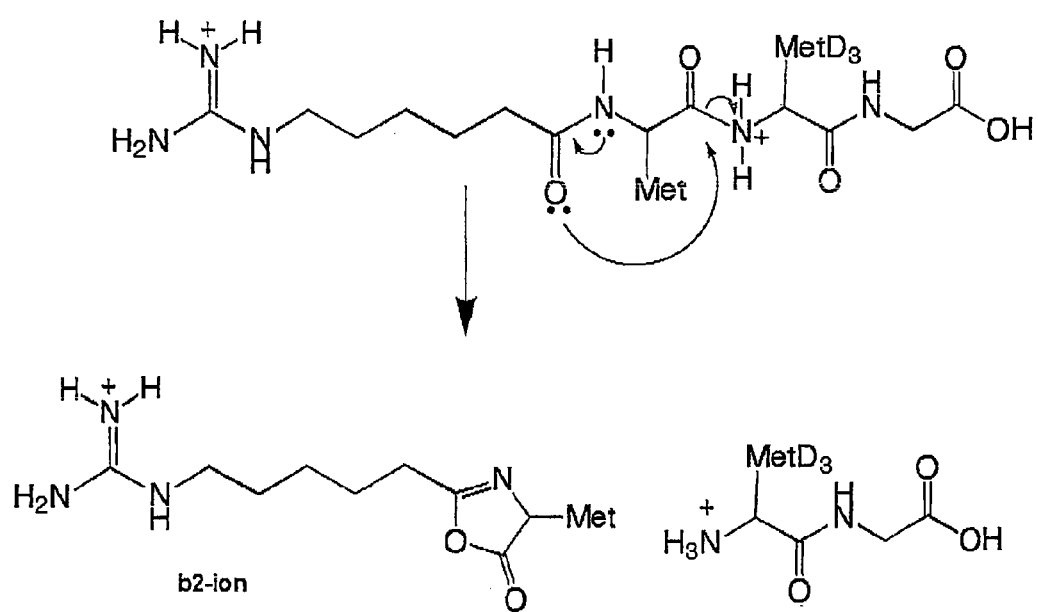
FIG. 13 shows a hypothetical fragmentation mechanism that is likely to account for the spectra shown in FIGS. 12 and 14.
Figure 14:
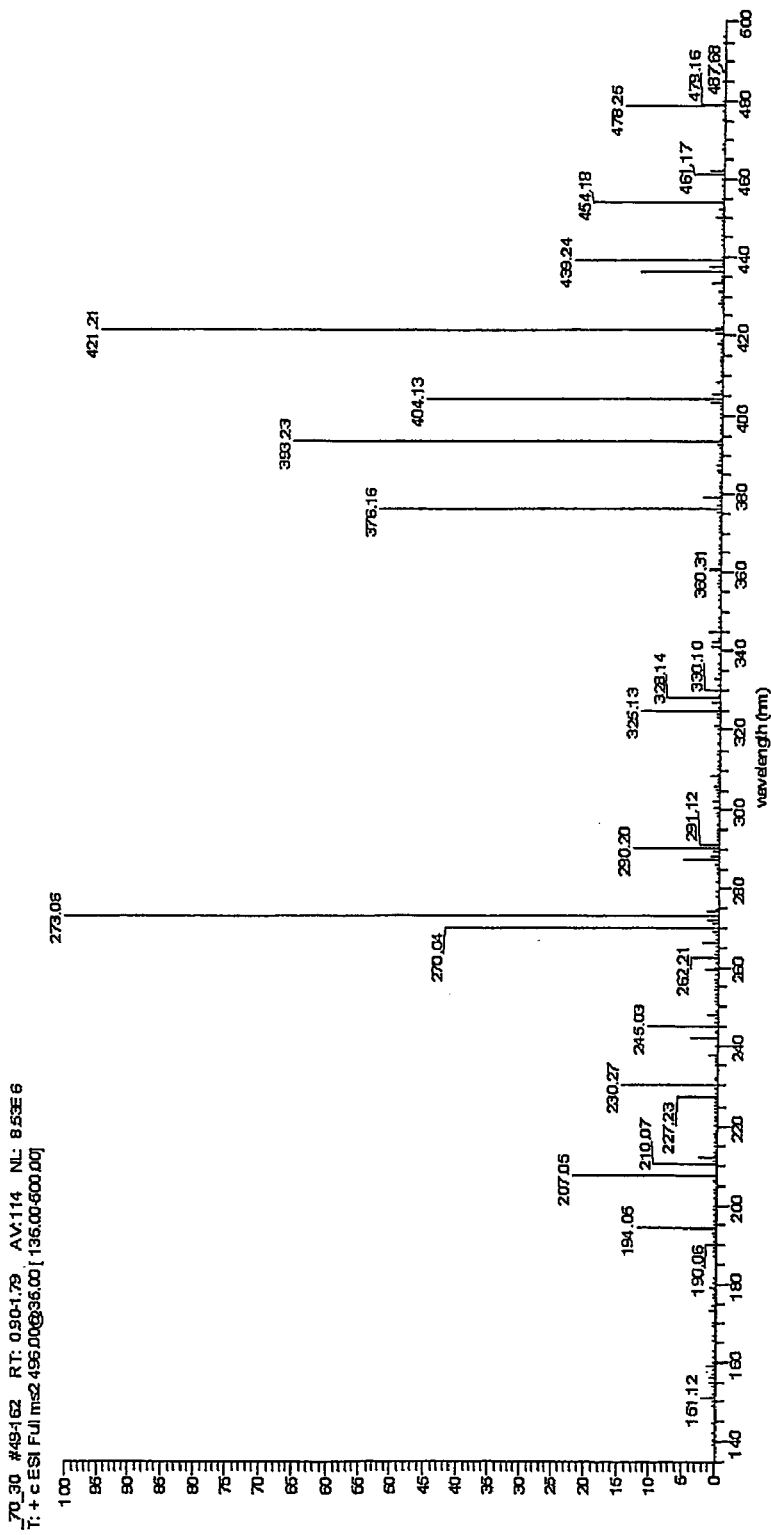
FIG. 14 shows an electrospray spectrum of the fragmentation of a 70:30 mixture of the two peptides shown in FIG. 10.
Figure 15:
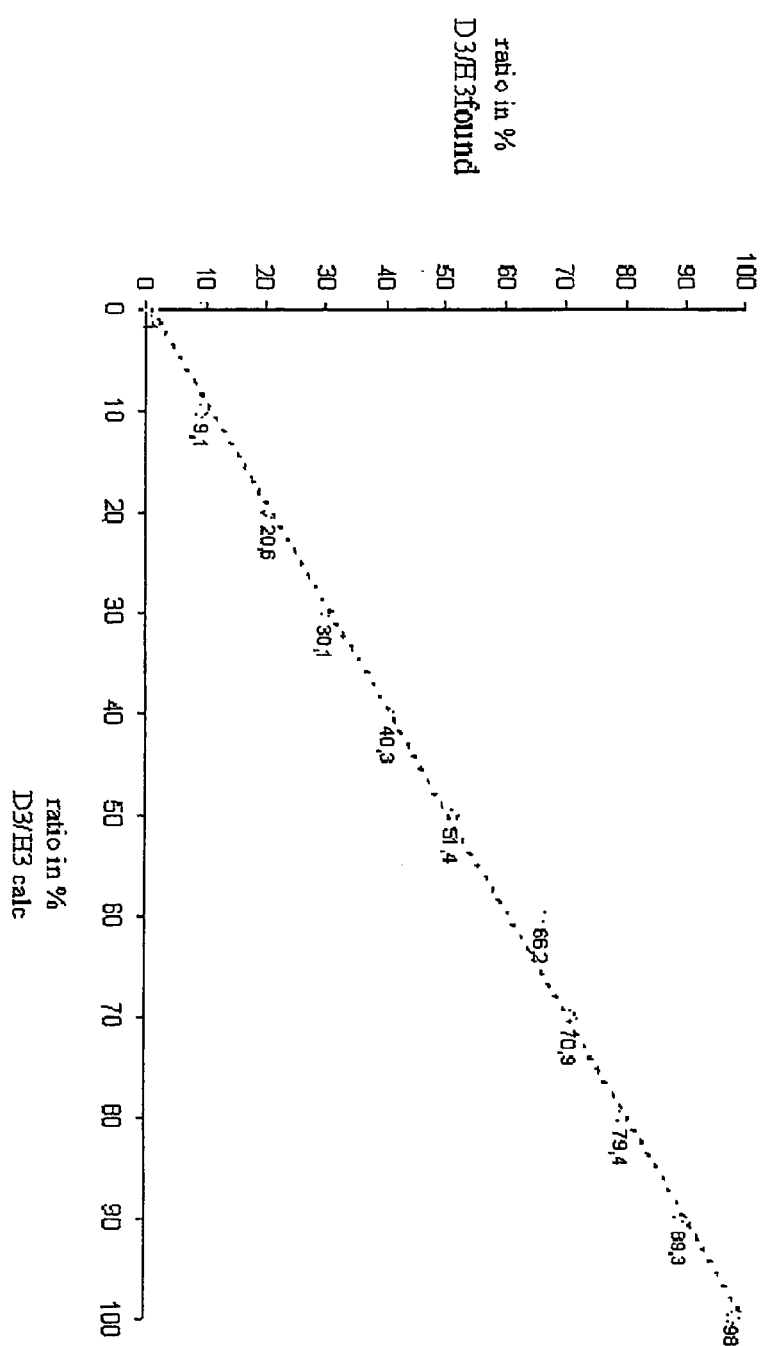
FIG. 15 shows a graph displaying the expected ratios of peptides A and B (FIG. 10) against observed ratios of peptides A and B found in a series of ESI-MS/MS analyses of mixtures of A an B.

FIG. 13 shows the proposed fragmentation reaction mechanism for the products of collision induced dissociation of the model peptides A and B shown in FIG. 10. FIG. 12 shows a pair of ESI MS/MS spectra generated by an LCQ ion trap mass spectrometer from Finnigan MAT. The ESI MS/MS spectra show the fragmentation products of peptides A and B. The desired 2-fragment ion (see FIG. 10) has a high intensity for both substances (273 after loss of ammonia for A and 270 after loss of ammonia for B). FIG. 14 shows and ESI-MS/MS spectrum of the fragmentation products from the analysis of a mixture of peptides A and B. A and B were present in the mixture in a ratio of 70:30 respectively. This ratio can be seen in the intensities of the b2-fragment ion peaks at m/z 273 and 270 for peptides A and B respectively. This spectrum shows that the tags can reveal the ratio of their associated peptides when pairs of samples are compared. FIG. 15 shows a linear regression curve for a series of ESI-MS/MS experiments with peptides A and B. The graph shows a plot of the ratio of A to B in the mixture against the observed intensities of the b2-fragment ions from ESI-MS/MS analysis of the mixtures. The graph shows that there is a good correspondence between the expected and observed ratios.

Example 2

Figure 9B:
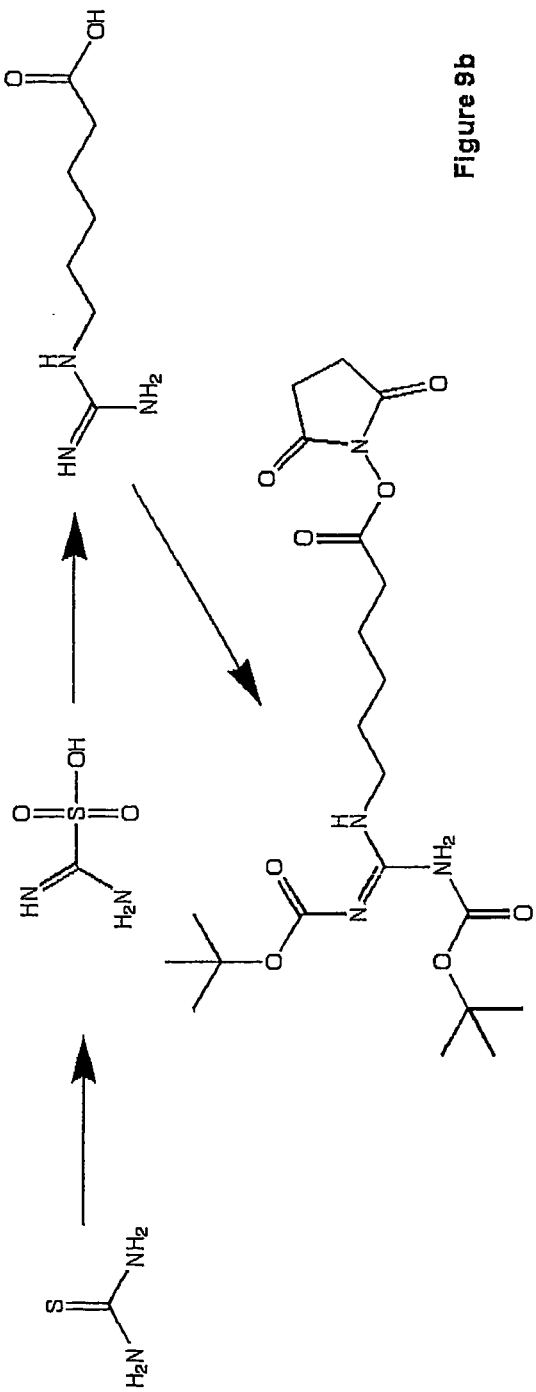
FIG. 9b shows a synthetic pathway for the preparation of a reactive linker that can act as a sensitivity enhancer.

6-[Bis(tert-butyl-oxycarbonyl) guanidino]-hexanoic acid-N-hydroxysuccinimidester The synthesis of the guanidino-active ester linker shown in FIG. 9b was carried out in 3 stages shown below.

1. Synthesis of amino-iminomethane sulphonic acid 50 mL acetic anhydride and 2 drops of conc. sulphuric acid were added to 45 g (397 mmol) 30% aqueous hydrogen peroxide under ice cooling. After 30 minutes, 100 mL (1157 mmol) acetic anhydride was added to the solution at 10-12° C. once again The reaction mixture was stirred overnight and reached the room temperature in that time. After adding 150 mL methanol, the solution made from 10 g (131 mmol) thiourea in 500 mL methanol was dropped slowly into the reaction at 15-20° C. The reaction was stirred at RT for 48 hours. After filtration, the solution was condensed to 60 mL. The obtained product was filtered and washed with ethanol and purified by crystallisation from acetic acid (ca. 1 L). Yield: 6.0 g (37%).

2. Synthesis of 6-Guanidinohexanoic acid 6.5 g (50 mmol) 6-aminohexanoic acid and 6.9 g (50 mmol) sodium carbonate were dissolved in 50 mL water. 6.2 g (50 mmol) amino-iminomethane sulphonic acid was added under stirring to the solution. After 20 hours, the product was filtered and washed with acetic acid, methanol and then ether. Yield: 6.6 g (76%).

3. Synthesis of 6-[Bis (tert-butyl-oxycarbonyl) guanidino]-hexanoic acid-N-hydroxy succinimide ester 9.5 g (55 mmol) 6-Guanidinohexanoic acid and 55 g (270 mmol) N,O-Bistrimethylsilylacetamide were stirred in 100 mL dichloromethane and heated under refluxing until a clear solution was obtained (the reaction was left for approximately 10 hours). 46 g (210 mmol) Di-tert-butyl pyrocarbonate was added to the solution at RT and the reaction mixture was heated under refluxing for 3 hours after having been stirred at RT for 18 hours (overnight). The solution was then cooled to RT and washed with a 10% citric acid solution and a sodium chloride solution. After evapouration of the solvent, the pyrocarbonate was distilled at 80-90° C. under vacuum. The viscous liquid obtained (30 g) was dissolved in 100 ml dichloromethane with 8.6 g (75 mmol) N-Hydroxysuccinimide. 15.5 g (75 mmol) dicyclohexylcarbodiimide (DCC) was added in portions to the reaction mixture with stirring at RT. After 17 hours, the urea was removed by filtration. The solution was washed with a 10% citric acid solution and after removing the solvent, the product was purified by chromatography (silica gel, solvent: dichloromethane/ethylacetate). The product was then crystallized from diisopropylether. Yield: 6.0 g (19%). Rf: 0.77 (dichloromethane/ethylacetate: 3/1). Fp: 108-109° C.

Example 3

Experimental Protocols

Figure 18A:
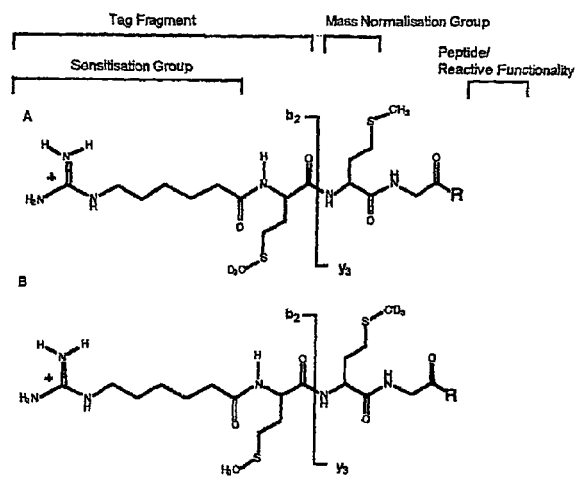
FIGS. 18a and 18b show the structures of two versions of the TMT markers, the tag fragment which results from the markers is shown in FIG. 18c.
Figure 18B:
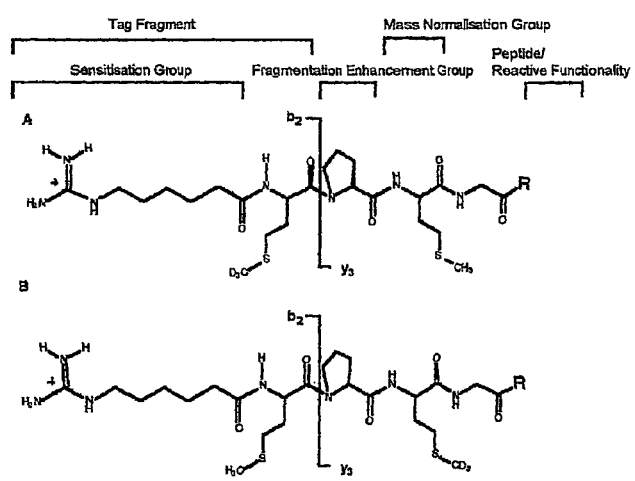

Two pairs of TMT reagents are shown in FIGS. 18a and 18b. The reagents are peptide tags according to this invention comprising one 'tag' amino acid linked to a sensitisation group ([1], [2], [3]), which is a guanidino-functionality, one 'mass normalisation' amino acid and in the second pair of tags, a cleavage enhancement group, which is proline in this case ([4]). These tags are designed so that on analysis by collision-induced dissociation (CID), the tag fragment is released to give rise to an ion with a specific mass-to-charge ratio. The current accepted model of peptide scission during CID requires protonation of the peptide backbone followed by nucleophilic attack of the carbonyl moiety of the protonated amide by the next N-terminal carbonyl residue in the peptide chain to form a relatively stable oxazolone leading to scission of the amide bond ([5]). The sensitisation enhancer is linked to the N-terminal methionine residue by an amide bond but cleavage does not take place at this amide as there is no amide correctly positioned to allow cyclisation and cleavage at this position so cleavage can only take place between the two methionine residues. This means that the N-terminal methionine is distinguished from the second methionine by the mass of the guanidino sensitisation group. Thus each pair of tags allows a pair of peptides to be distinguished by MS/MS analysis. Each tag can also bear a reactive functionality. In the figure, the reactive functionality, R, is not specified but could be an N-hydroxysuccinimide ester, which allows for the specific labeling of amino-groups. Clearly this reactive functionality can be easily varied to allow different biological nucleophiles to be labeled. In addition, the tag design can be readily modified to accommodate an affinity ligand such as biotin. Furthermore, it should be clear that more than two tags can be generated allowing for comparison of additional samples or for the introduction of labeled standards.

imide ester (NHS-ester) as described above and added to deprotected alpha-amino groups of synthetic peptides by conventional methods during automated peptide synthesis.

TABLE 7

| | | Generation 1 | | Generation 2 | |
|---|---|---|---|---|---|
| Peptide sequences | | $M_i$ | Ion at m/z (z) | $M_i$ | Ion at m/z (z) |
| 1A | TMT-GVATVSLPR | 1319.7 | 660.9 (2+) | 1415.7 | 708.9 (2+) |
| 1B | TMT-GVATVSLPR | 1319.7 | 660.9 (2+) | 1415.7 | 708.9 (2+) |
| 2A | TMT-GLGEHNIDVLEGNEQFINAAK | 2688.31 | 897.1 (3+) | 2784.3 | 928.8 (3+) |
| 2B | TMT-GLGEHNIDVLEGNEQFINAAK | 2688.31 | 897.1 (3+) | 2784.3 | 928.8 (3+) |
| 3A | TMT-GNKPGVYTK | 1383.7 | 462.2 (3+) | 1479.7 | 494.3 (3+) |
| 3B | TMT-GNKPGVYTK | 1383.7 | 462.2 (3+) | 1479.7 | 494.3 (3+) |
| 4A | TMT-GDPAALKRARNTEAARRSRAR KLQRMKQGGC | 3874.6 | 969.7 (4+) | 3970.6 | 993.7 (4+) |
| 4B | TMT-GDPAALKRARNTEAARRSRAR KLQRMKQGGC | 3874.6 | 969.7 (4+) | 3970.6 | 993.7 (4+) |

In the following examples, peptides, listed in Table 7, have been synthesised as if they have been completely labeled on the alpha amino group with the above tags, i.e. the tag was 'pre-incorporated' during the synthesis to test the performance of the tags independently of the labeling reactions, so that in the following examples the 'R' group shown in FIGS. 18a and 18b is the peptide sequence to which the tag is attached. The tagged peptides were analysed by ESI-MS/MS and LC-ESI-MS/MS.

Figure 18C:
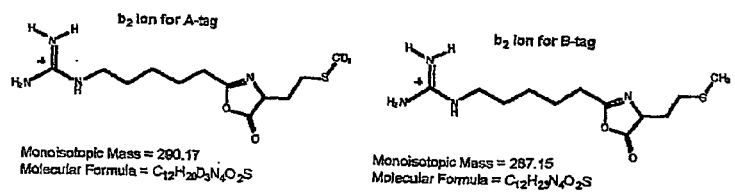

FIGS. 18a and 18b show the structures of two versions of the TMT markers. The tags are modular comprising different functional components that correspond to individual synthetic components in the automated synthesis of these reagents. Each tag comprises a sensitisation group and a mass differentiated group that together comprise the 'tag fragment' that is actually detected. The tag fragment is linked to a mass normalisation group that ensures that each tag in a pair of tags share the same overall mass and atomic composition. The first and second generation tags are distinguished by the presence of an additional fragmentation enhancing group, proline, in the second generation tag. The tags will additionally comprise a reactive functionality (R) to enable the tag to be coupled to any peptide but in the present experiments, R is one of a number of peptide sequences. The proposed tag fragment that results from the markers is shown in FIG. 18c based on current theories on backbone protonation dependent mechanisms of fragmentation ([5]).

Syntheses of TMT Labeled Peptides

The peptides shown in Table 7 were synthesised using conventional automated Fmoc synthesis techniques (both starting from commercially available Fmoc-Gly-Trt-PS resin from Rapp Polymere, Germany). Deuterated methionine (Metd$^3$) is available from ISOTEC Inc, Miamisburg, Ohio, USA. An Fmoc-Metd$^3$ reagent for use in a peptide synthesiser was synthesised manually from the unprotected deuterated methionine as described above. The guanidino 'sensitisation' enhancement group was synthesized as an N-hydroxysuccin- Table 7: Abundance ratio experiments were performed with the peptides listed above. HPLC experiments were performed with the first three peptide sequences listed above. Pairs of synthetic peptides were prepared with either the first or second TMT pre-incorporated into the peptide sequence at the N-terminus. Sequences, mono-isotopic molecular mass and mass-to-charge ratios of predominant ion species are listed for each tag.

MS/MS Analysis of TMT-Labeled Peptides

Analyses were performed by liquid chromatography mass spectrometry using either a Finnigan LCQ Deca with a Finnigan Surveyor HPLC System (Column: 50×2.1 mm, 5 μm HyPURITY™ Elite C18) or a QTOF 2 from Micromass Ltd, Manchester, UK with a Cap-LC HPLC system from LEAP Technologies (Column: PepMap C18 HPLC column from Dionex with a 75 μm inner diameter was used; the resin had a 3 μm particle size, 100 A pore size).

Ion abundance ratios were determined by summation and averaging of a number of spectra of an eluting peptide pair followed by determination of the ratios of the peak intensities for the tag fragments.

Example 3a

Comparison of $1^{st}$ and $2^{nd}$ generation TMT tags

To demonstrate the advantages of a tag designed with a fragmentation enhancing group two different TMT designs were explored. The tags differ by the inclusion of proline in the $2^{nd}$ generation tags (FIGS. 18a and 18b). Proline is known to enhance cleavage of the amide bond on its N-terminal side ([4]).

Initial experiments on the fragmentation of the $1^{st}$ generation of TMT in a Micromass QTOF 2 instrument showed that the intensity of the TMT fragments was very dependant on the amino acid sequence of the peptide and at low collision energies the tag fragments did not accurately reflect the abundances of the tagged peptides. As shown in FIG. 1c the expected tag fragments have an m/z of 287 or 290 but, in the first generation tags, a second pair of ions with mass-to-charge ratios of 270 or 273 is observed. These fragments are thought to result from the loss of ammonia from the expected tag fragments. An example of a typical CID spectrum for a peptide labeled with the first generation tags is shown in FIG. 19. At lower collision energies the intensities of these two fragment classes varied with the sequence of the attached peptide but at higher CID energies the 270/273 fragments are observed almost exclusively. At these higher collision energies, the 270/273 tag fragments did accurately reflect the abundances of the peptide pairs. Additional experiments using a Finnigan LCQ ion trap mass spectrometer have shown the same fragmentation pattern as the QTOF for the first generation TMT units. The observed ammonia loss occurs in both LCQ and QTOF experiments. These instruments differ in the manner in which CID is carried out (selective activation and fragmentation of only the parent ion in the LCQ versus serial fragmentation of all ions in QTOF). Since the loss of $NH_3$ takes place in both instruments, this suggests that the loss of $NH_3$ may take place directly from the parent peptide ion, rather than as a result of subsequent collisions of the expected fragment ion and is an intrinsic feature of this tag structure. In both instruments the appearance of the 270/273 fragment is favoured by higher collision energies. This meant that to get consistent behaviour from this tag analysis had to take place at high collision energies.

Although CID is more selective in the LCQ, it is unfortunately limited in its use with TMTs as it is not possible to detect small CID fragmentation products of larger precursors with this type of instrument. In the QTOF instrument, however, at the higher energies of collision, consecutive fragmentations were problematic. In the Q-TOF, the series of b- or y-ion fragments that provide sequence information are further fragmented to give smaller species so that no sequence information could be obtained from the peptide. As a result of the need for high energy CID to guarantee the release of the tag fragments and to obtain accurate quantification, the first generation TMT units can only be reliably used for the purposes of quantification without peptide identification in the QTOF. This will also be true of other serial MS/MS instruments.

Figure 19A:
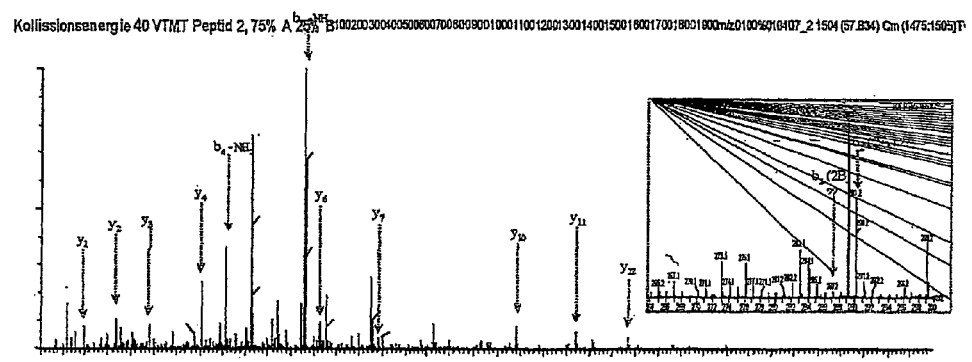
FIGS. 19a and 19b show typical CID spectra for a peptide labeled with the first generation TMT at collision energies of 40V (FIG. 19a) and 70V (FIG. 19b)
Figure 19B:
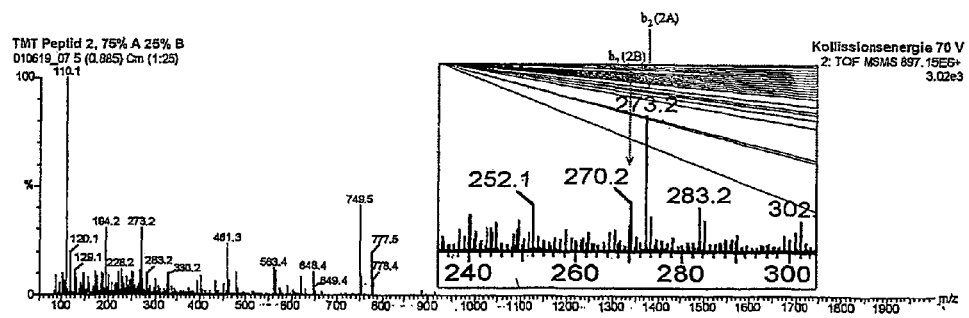

FIGS. 19a and 19b show typical CID spectra for a peptide labeled with the first generation TMT at collision energies of 40V (FIG. 19a) and 70V (FIG. 19b). In 19a weak peaks in both of the 270/273 and 287/290 regions can be seen at 40V, but they do not accurately represent the abundances of the tagged peptides. Some sequence specific y-series ions can be observed though at this accelerating potential. In 19b the peaks corresponding to the tag fragment can be seen clearly at m/z 270 and 273 for the first generation TMT at a collision energy of 70V. At this collision energy the intensities of these peaks accurately represent the relative abundances of each peptide (see inset for zoom of the tag region in FIG. 19b) but no sequence data can be determined.

These results lead to the development of a $2^{nd}$ generation TMT, which has a proline residue in the TMT unit to enhance the fragmentation. To quantify the effect of the proline in the second generation tags a 50:50 mixture of a peptide labeled with the first and second generation tags respectively was analysed by MS/MS. The two resultant peptides, with the sequences Guanidinocaproyl-Met(D3)-Met-GLGEHNIDV-LEGNEQFINAAK and Guanidinocaproyl-Met(D3)-Pro-Met-GLGEHNIDVLEGNEQFINAAK, had ions corresponding to the $[M+3H]^{3+}$ species at mass-to-charge ratios of approximately 897 and 929 for the first and second generation tags respectively. To get the same collision conditions for both precursors, the peptides were first mixed and then analysed in a QTOF instrument with the quadrupole set to alternately select ions with m/z around 897 or 929. Each selected ion was subjected to CID at increasing collision energies.

At collision energies of 20V or less no fragmentation at all was observed for either type of TMT. At a collision energy of 30V-35V it is possible to see the expected TMT fragment ions at m/z of 290 in the CID spectrum for the peptide with the second generation tag but no fragment ions m/z of 273 can be seen in the spectrum for the peptide with the first generation tag at the same energy, see FIG. 20, although a weak fragment at m/z of 290 can be seen. The tag fragment for the peptide containing the first generation TMT is not observed until a collision energy of 70V is used (data not shown). Smaller peptides labeled with the first generation TMT gave rise to the tag fragment at lower energies but high collision energies were required to release the tag fragment from larger peptides. The size dependence of the peptide on the energy needed to release the tag fragment was much smaller for the second generation TMT. Comparison of the CID spectra from peptides labeled with TMTs containing proline with peptides labeled with TMTs without proline shows clearly that the introduction of the proline amino acid as a fragmentation enhancer leads to fragmentation in favour of the expected TMT tag fragment without resorting to very high collision energies. At these lower energies the abundance ratios also of the TMT fragment ions, from the proline containing TMTs, accurately reflect the ratios of the concentrations of the tagged peptides. In addition, the identification of the peptide via its b and y series can also be performed at these lower collision energies.

FIGS. 20a 20b and 20c show MS and MS/MS spectra for triply charged ions of the peptide 2 (see Table 7) labeled with the first and second generation TMTs. The peptides were analysed in a QTOF II instrument. FIG. 20a shows the MS-mode TOF spectrum of the peptide mixture. For CID analysis the first quadrupole was set to alternately select ions with m/z around 897 or 929. The CID spectrum at 35V for Guanidinocaproyl-Met(D3)-Met-GLGEHNIDVLEGNEQFINAAK is shown in FIG. 20b and the CID spectrum at 35V of Guanidinocaproyl-Met(D3)-Pro-Met-GLGEHNIDVLEGNEQFI-NAAK is shown in FIG. 20c. The presence of the expected tag fragment at m/z of 273 is not detected for the first generation TMT in FIG. 20b but the expected fragment at 290 is clearly observed at 35V for the second generation TMT in FIG. 20c.

The improved behaviour of the second generation TMT can be seen in FIG. 21 which shows a typical CID spectrum of a peptide labeled with these tags. The tag fragments revealing the abundance ratios are easily seen at the expected m/z values of 287 and 290. In addition it is possible to see both b-series and y-series ions allowing the sequence of the peptide to be determined. CID was performed at a relatively low collision energy of 40V. The peaks at m/z 287 and 290 for the second generation TMT at 40V represent the relative abundances of each peptide (see inset with zoom of the relevant region of the mass spectrum).

FIG. 22 clearly shows that the charge state of the TMT tagged peptide does not affect the appearance of the tag fragments in the CID spectra of the labeled peptides. In this example a peptide labeled with a first generation TMT is shown but the same result is found for the second generation tags. This is advantageous as it means that scanning of the spectrum can take place without complex adjustments of the scanning software to compensate for the charge state of each peptide. In other isotope tagging procedures, such as ICAT, the charge state alters the mass difference between each tagged ion pair, such that for doubly charged ions the mass difference is halved, for triply charged ions the mass difference is a third of that for the singly charged ions, etc. Software to scan for peptide pairs using conventional isotope labeling techniques, like ICAT, must therefore compensate for these sorts of problems by allowing for the different possible mass differences or by ignoring certain classes of ion, which either increases the chance of erroneous identification of peptide pairs or misses out on potential ion pairs that could offer useful information.

In FIG. 22, comparison of spectra for peptide 4 from Table 7 where CID has been performed on the $[M+4H]^{4+}$ (bottom spectrum) and $[M+5H]^{5+}$ (top spectrum) species. The peptide above contains the first generation TMT. The 4+ ion has an m/z of 969.3 while the 5+ ion has an m/z of 775.6. The tag fragment ion appears at the expected mass-to-charge ratio of 273 in both spectra indicating that only one charge localises to the tag fragment.

FIG. 23 shows data for expected and observed ratios of peptides from ESI-MS/MS analyses of the 4 peptides listed in Table 7. Peptides with both first and second generation TMTs incorporated into them were analysed. Abundance ratios were determined by analysing the peak maxima at the d3 (A) and d0 (B) of the tag fragment ion peaks after peak normalization at 290 and 287 for TMT2. Measurements were made in a QTOF instrument. The table inset to FIG. 23 shows expected and observed ratios the b-ion fragments from the MS/MS analysis of eluting TMT labeled peptides. It can be seen that both generations of TMT provide accurate representation of abundance ratios of the peptides in the mixtures and that the tags show linear behaviour over the entire range of peptide ratios tested.

Example 3b

Demonstration of identical chromatographic behaviour of TMT tags in LC-MS

A mixture of four pairs of synthetic peptides were synthesised with the second generation TMT units pre-incorporated at the N-terminus of each peptide. The peptide pairs were all analysed together. Each peptide pair was prepared at a different ratio. The sequences, theoretical mono-isotopic masses, the doubly charged ion masses are shown in Table 7. The peptides were loaded onto a C-18 reverse phase HPLC column and separated. The purpose of this experiment was to demonstrate the exact co-elution of corresponding pairs of peptides with different TMT tags without any other complications. The ratios of the peptide pairs were expected and found to be consistent over the entire elution time for each peptide pair and so a further object of this experiment was to show that quantification of the peptide pairs could be performed with simultaneous sequence determination and that it would be possible to scan for other peptides without waiting for the complete elution of the peptide. Complete elution of peptide pairs is necessary for accurate quantification using the ICAT strategy and other peptide analysis techniques using conventional isotope labeling. This greatly restricts the throughput of these approaches.

FIG. 24 shows the co-elution of each peptide pair, peptides A and B for each peptide from Table 7, clearly seen in the C18-reverse phase HPLC traces. For each peptide the ion currents at m/z 287 and 290 are recorded corresponding to the tag fragments from each of the TMTs. The bottom trace for each peptide is the total ion current. The elution profiles of 3 peptides monitored at each of the mass-to-charge ratios of the $b_2$ ions from the tag fragments are shown. It can be clearly seen that the peptide pairs elute as a single fraction. In MS/MS mode, monitoring of the tag fragment ions produces virtually identical results in each case. For each peptide pair the observed ratios matched the expected ratios to a reasonable degree.

Since the tagged peptides exactly co-elute, the ratios of the peptide pairs are conserved throughout the elution profile, which means that it is not necessary to integrate the total ion current for the eluting ions to determine the relative abundance of each peptide pair.

Example 3c

Analysis of the sensitivity and robustness of the TMT technology

To provide an effective improvement over conventional isotope labeling, the TMT technology must be at least as sensitive as other isotope labeling methods and must have a broadly similar dynamic range. In addition, the properties of the tags must be consistent over the whole expected dynamic range of the samples to be analysed. Finally, the ability of these tags to overcome noise in the mass spectrometer needed to be demonstrated. To test the dynamic range of the system and to show that the properties of the TMT tags are consistent over the entire dynamic range, the conservation of peptide ratios was examined at a range of different concentrations of one of the tagged synthetic peptides (peptide 3A and 3B). As can be seen from FIG. 25, a serial dilution of peptides 3A and 3B, mixed in a ratio of 40:60, from 100 pmoles to 100 fmoles, the ratios were reliably conserved with a deviation within 5% in most cases, from the expected ratio. These and other results (not shown) indicate that the tag peptides do not reduce the intrinsic sensitivity with which a peptide is detected in the MS/MS mode, i.e. the analysis of TMT labeled peptides by CID has essentially the same sensitivity as the MS/MS of untagged peptides. The intrinsic sensitivity seems to be instrument specific based on comparisons between the LCQ and QTOF in the analysis of small peptides (the tag fragments from large peptides labeled with TMTs cannot be detected on the LCQ because of the intrinsic limitations on CID with this type of instrument). The sensitivity with which it is possible to determine the sequence of tagged peptides does not seem to be have been significantly changed in any of the peptides tested so far. Meaningful differences in the ratios of the peptides can be detected over the entire range of concentrations tested (FIG. 25).

FIGS. 26a 26b and 26c show the results of a spiking experiment in which peptides pairs 3A and 3B (500 fmol in total, in a ratio of 40:60 respectively) bearing a second generation TMT was mixed with a tryptic digest of Bovine Serum Albumin (2 pmol). FIG. 26a shows the base peak chromatogram from analysis in the MS-mode. During the run, the first five most intensive ions analysed in MS mode were automatically fragmented in the MS/MS mode at 30V. The TMT peptides pairs were investigated and located on the base peak chromatogram. The ratio of the TMT2 fragments was then calculated from the MS/MS spectrum for the mass $[M+3H]^{3+}$ (a zoom of the tag fragments is shown in FIG. 9b and the whole spectrum shown in FIG. 9c) by comparing the intensity of the d0 and d3 TMT fragment mass-to-charge ratios (287 and 290).

In a further experiment, the ability to detect labeled peptides in a background of contaminating peptides was examined. The peptides pairs 3A and 3B bearing a second generation TMT was mixed with a 20-fold excess of a tryptic digest of Bovine Serum Albumin. The peptide mixture was then analysed in an LC-QTOF instrument. The five most intense ions from each elution scan were subjected to CID to identify the peptides. The expected peptides were detected and the region of spectrum corresponding to the tag fragments was analysed to determine the abundance ratio of the detected peptides. Analysis by CID (collision energy of 30V), provides the spectrum shown in FIG. 26c. The ratio of the peptides 3A and 3B was found to be 39.3% to 60.7% respectively, by comparison of the peak intensities at the fragment ion mass-to-charge ratios of 290 (d3 TMT unit) and 287 (d0 TMT unit). The expected ratio was 40% 3A to 60% 3B, thus the peptide ratio was detected with a 1.7% error. The quality of the MS/MS spectrum obtained (FIGS. 26b and 26c) at the low collision energy used, allows a clear identification of the peptide sequence by database searching. This experiment clearly shows that a complex mixture of tryptic peptides does not hinder the analysis of peptide pairs labeled with the $2^{nd}$ generation TMT tags and the TMTs can help to overcome noise in the sample. In addition there do not seem to be any suppression problems—ratios of peptides present in low concentrations can still be determined in the presence of other peptides that are in high concentrations.

References:
1. Brancia, F. L., S. G. Oliver, and S. J. Gaskell, *Improved matrix-assisted laser desorption/ionisation mass spectrometric analysis of tryptic hydrolysates of proteins following guanidination of lysine-containing peptides.* Rapid Commun Mass Spectrom, 2000. 14(21): p. 2070-3.
2. Roth, K. D., et al., *Charge derivatization of peptides for analysis by mass spectrometry.* Mass Spectrom Rev, 1998. 17(4): p. 255-74.
3. Brancia, F. L., et al., *A combination of chemical derivatisation and improved bioinformatic tools optimises protein identification for proteomics.* Electrophoresis, 2001. 22(3): p. 552-9.
4. Schwartz, B. L. and M. M. Bursey, *Some proline substituent effects in the tandem mass spectrum of protonated pentaalanine.* Biol Mass Spectrom, 1992. 21(2): p. 92-6.
5. Schlosser, A. and W. D. Lehmann, *Five-membered ring formation in unimolecular reactions of peptides: a key structural element controlling low-energy collision-induced dissociation of peptides.* J Mass Spectrom, 2000. 35(12): p. 1382-90.
6. Griffin, T. J., et al., *Toward a high-throughput approach to quantitative proteomic analysis: expression-dependent protein identification by mass spectrometry.* J Am Soc Mass Spectrom, 2001. 12(12): p. 1238-1246.
7. Zhou, H., J. D. Watts, and R. Aebersold, *A systematic approach to the analysis of protein phosphorylation.* Nat Biotechnol, 2001. 19(4): p. 375-8.
8. Oda, Y., T. Nagasu, and B. T. Chait, *Enrichment analysis of phosphorylated proteins as a tool for probing the phosphoproteome.* Nat Biotechnol, 2001. 19(4): p. 379-82.
9. Ficarro, S. B., et al., *Phosphoproteome analysis by mass spectrometry and its application to Saccharomyces cerevisiae.* Nat Biotechnol, 2002. 20(3): p. 301-5.

The invention claimed is:
1. A set of two or more mass labels, each mass label in the set comprising a mass marker moiety attached via a cleavable linker having at least one amide bond to a mass normalisation moiety, the mass marker moiety being fragmentation resistant, wherein each mass normalisation moiety ensures that each mass label in the set has the same aggregate mass as determined by mass spectrometry, and wherein, each mass marker moiety has a mass different from that of all other mass marker moieties as determined by mass spectrometry, and wherein all of the mass labels in the set are distinguishable from each other by mass spectrometry, and wherein the mass marker moiety comprises an amino acid and the mass normalisation moiety comprises an amino acid.

2. A set of mass labels according to claim 1, in which each mass marker moiety in the set has the same structural core, and each mass normalisation moiety in the set has the same structural core that may be the same or different from the structural core of the mass marker moieties, and wherein each mass label in the set comprises one or more mass adjuster moieties, the mass adjuster moieties being attached to or situated within the structural core of the mass marker moiety and/or the structural core of the mass normalisation moiety, such that every mass marker moiety in the set comprises a different number of mass adjuster moieties and every mass label in the set has the same number of mass adjuster moieties.

3. A set of mass labels according to claim 2, each mass label in the set having the following structure:

M(A)y-L-X(A)z wherein M is a mass normalisation moiety comprising an amino acid, X is a mass marker moiety comprising an amino acid, A is a mass adjuster moiety, L is a cleavable linker comprising the amide bond, y and z are integers of 0 or greater, and y+z is an integer of 1 or greater.

4. A set of mass labels according to claim 2, wherein the mass adjuster moiety is selected from:
(a) an isotopic substituent situated within the structural core of the mass marker moiety and/or within the structural core of the mass normalisation moiety, and
(b) substituent atoms or groups attached to the structural core of the mass marker moiety and/or attached to the structural core of the mass normalisation moiety.

5. A set of mass labels according to claim 4, wherein the mass adjuster moiety is selected from a halogen atom substituent, a methyl group substituent, and $^2$H or $^{13}$C isotopic substituents.

6. A set of mass labels according to claim 5, wherein the mass adjuster moiety is a fluorine atom substituent.

7. A set of mass labels according to claim 1, wherein the cleavable linker attaching the mass marker moiety to the mass normalisation moiety is a linker cleavable by collision induced dissociation.

8. A set of mass labels according to claim 1, wherein the cleavable linker comprises proline and/or aspartic acid.

9. A set of mass labels according to claim 1, wherein the mass normalisation moiety comprises a fragmentation resistant group.

10. A set of mass labels according to claim 1, wherein the mass marker moiety comprises a sensitivity enhancing group.

11. A set of mass labels according to claim 1, wherein the mass marker moiety or the mass normalisation moiety comprises a reactive functionality.

12. A set of mass labels according to claim 1, wherein each mass label in the set comprises an affinity capture ligand.

13. A set of mass labels according to claim 1, further comprising a set of two or more analytes, each analyte in the set being different and being attached to a unique mass label or a unique combination of mass labels, from the set of mass labels.

14. A set of mass labels according to claim 13, wherein one or more analytes in the set is a standard analyte having a known mass, or known chromatographic properties.

15. A set of mass labels according to claim 1, further comprising a set of two or more probes, each probe in the set being different and being attached to a unique mass label or a unique combination of mass labels, from the set of mass labels.

16. A set of mass labels according to claim 13, wherein each analyte is attached to a unique combination of mass labels, each combination being distinguished by the presence and absence of each mass label in the set of mass labels and/or the quantity of each mass label attached to the analyte.

17. A set of mass labels according to claim 13, wherein each analyte comprises a biomolecule.

18. A set of mass labels according to claim 17, wherein the biomolecule is selected from a DNA, an RNA, an oligonucleotide, a nucleic acid base, a protein and/or an amino acid.

19. A set of probes according to claim 15, wherein each probe is attached to a unique combination of mass labels, each combination being distinguished by the presence and absence of each mass label in the set of mass labels and/or the quantity of each mass label attached to the probe.

20. A set of probes according to claim 15, wherein each probe comprises a biomolecule.

21. The set of probes according to claim 10, wherein the sensitivity enhancing group is a pre ionized group.

22. The set of probes according to claim 12, wherein the affinity capture ligand is biotin.

* * * * *